US007751873B2

(12) United States Patent
de Voir

(10) Patent No.: US 7,751,873 B2
(45) Date of Patent: Jul. 6, 2010

(54) WAVELET BASED FEATURE EXTRACTION AND DIMENSION REDUCTION FOR THE CLASSIFICATION OF HUMAN CARDIAC ELECTROGRAM DEPOLARIZATION WAVEFORMS

(75) Inventor: Christopher S. de Voir, Tigard, OR (US)

(73) Assignee: Biotronik CRM Patent AG, Baar (CH)

( * ) Notice: Subject to any disclaimer, the term of this patent is extended or adjusted under 35 U.S.C. 154(b) by 422 days.

(21) Appl. No.: 11/933,924

(22) Filed: Nov. 1, 2007

(65) Prior Publication Data
US 2008/0109041 A1 May 8, 2008

Related U.S. Application Data

(60) Provisional application No. 60/864,861, filed on Nov. 8, 2006.

(51) Int. Cl.
*A61N 1/365* (2006.01)
(52) U.S. Cl. ............................................ 600/509; 607/2
(58) Field of Classification Search ............... 607/1–17; 600/509–512; 382/128
See application file for complete search history.

(56) References Cited

U.S. PATENT DOCUMENTS

| 5,439,483 A | 8/1995 | Duong-Van |
| 5,638,823 A | 6/1997 | Akay et al. |
| 6,135,966 A | 10/2000 | Ko |
| 6,677,892 B1 | 6/2003 | Schomburg |
| 7,397,936 B2 * | 7/2008 | Periaswamy ................. 382/128 |
| 2004/0111121 A1 * | 6/2004 | Brown et al. .................... 607/5 |
| 2005/0071303 A1 | 3/2005 | de Voir et al. |

OTHER PUBLICATIONS

"Analysis of the Electrocardiogram by the Lifting Scheme"; R. Sai, M. Ben Messaoud, A. Kachouri and F. Sellami; Control, Communications and Signal Processing; Sep. 27, 2004.*
"Electrocardiogram signal de-noising using lifting-based discrete wavelet transform"; E. Ercelebi; Computers in Biology and Medicine; 34 (2004) 479-493.*

* cited by examiner

*Primary Examiner*—Carl H Layno
*Assistant Examiner*—Paula J Stice
(74) *Attorney, Agent, or Firm*—ARC IP Law, PC; Joseph J. Mayo

(57) ABSTRACT

A depolarization waveform classifier based on the Modified lifting line wavelet Transform is described. Overcomes problems in existing rate-based event classifiers. A task for pacemaker/defibrillators is the accurate identification of rhythm categories so correct electrotherapy can be administered. Because some rhythms cause rapid dangerous drop in cardiac output, it's desirable to categorize depolarization waveforms on a beat-to-beat basis to accomplish rhythm classification as rapidly as possible. Although rate based methods of event categorization have served well in implanted devices, these methods suffer in sensitivity and specificity when atrial/ventricular rates are similar. Human experts differentiate rhythms by morphological features of strip chart electrocardiograms. The wavelet transform approximates human expert analysis function because it correlates distinct morphological features at multiple scales. The accuracy of implanted rhythm determination can then be improved by using human-appreciable time domain features enhanced by time scale decomposition of depolarization waveforms.

20 Claims, 49 Drawing Sheets

FIG. 5  Two rhythms with similar (non-unique) rates cannot be distinguished when only rate-based information is present FIG. 6. Cardiac blood flows in the direction of the arrows (Schaldach, 1992, p. 2)

FIG. 7. Natural pacemaker and conduction system (Schaldach, 1992, p. 5)

The IEGM results from ion flow across the cell membrane and the resulting transmembrane potential. (Schaldach, p. 7)

FIG. 9  Action potentials vary with tissue type (Netter & Yonkman, 1978, p. 49)

FIG. 10  Cardiac myocyte interior cross-section (Klabunde, 2004)

FIG. 11   IEGM deflection, (Ellenbogen, Kay, & Wilkoff, 2000, p. 69)

The orientation axis through the electrodes relative to the direction of the excitation wavefront affects the amplitude of the IEGM (Ellenbogen, Kay, & Wilkoff, 2000, p. 69).

FIG. 13  Resultant vector from two components (Netter & Yonkman, 1978, p. 52)

FIG. 14  Frontal leads (Barold, Stroobandt, & Sinnaeve, 2004, p. 8)

FIG. 15  Intra-cardiac electrogram of normal sinus rhythm

FIG. 16  Bipolar lead contact elements (Biotronik, 2001)

A comparison of simultaneous recordings shows the bipolar event has a well-defined onset, and the unipolar event does not.

The IEGM is converted to threshold crossing event by the input stage of an implantable device (Ellenbogen, Kay, & Wilkoff, 2000, p. 87).

The frequency content of IEGM features for threshold based event detection is concentrated in specific regions of the pass band (Ellenbogen, Kay, & Wilkoff, 2000, p. 73).

The original IEGM (wideband) is filtered (narrowband) to reduce aliasing and false detection of events at the threshold comparator.

FIG. 21  Conversion of IEGM to event markers

Despite adaptive thresholds and complex timing windows, pseudo-events are indistinguishable from real events when morphology is excluded.

Depolarization of the heart through an aberrant conduction path causes the changed morphology of the ventricular (e), and atrial (r) events.

Centering event time samples on the of peak amplitude reveals the morphological differences of normal and abnormal events.

The wavelet scalogram shows two examples of the hierarchal generation of the wavelet coefficients from a single data window.

Processing efficiency can be improved through a cascade equivalency.

The separability of two conceptual distributions corresponds to the ROC AUC, whose most discriminating threshold corresponds to the ROC vertex.

FIG. 28  Peak alignment of events from two different categories

For three different methods to compute the wavelet transform of one IEGM event, the number of multiply-add operations varies by wavelet filter order.

FIG. 30  Wavelet transforms coefficients of two IEGM events

IEGM observations are transformed into wavelet coefficients and reduced to a single discriminating WTC using true class data.

FIG. 32 LWT energy costs can be reduced by not processing all the sub-bands

Normalized evaluation accuracy means (95% LCL) organized by sub-band shows concentration of accuracy within the acceptance criterion.

Selecting LWT coefficients by either AUC maximum or confirmation accuracy maximum resulted in mean evaluation accuracies ≥95%.

Distribution of selected LWT coefficients by AUC and confirmation accuracy maximums resulted in energy savings of 27% and 21%.

Fig. 36 Event Processing Diagram

FIG. 37 Sliding and scaling allows resolution of all points of $f$.

FIG. 38  Impulse response of discrete time lifting line wavelet transform filters FIG. 39  Magnitude and phase response of low and high pass WT blocks Dataflow diagram of analysis levels Scaling spans the signal values FIG. 42  Even samples predicting odd samples

Fig. 43 Flow diagram of the splitting function

Splitting redistributes even and odd values, for operations on 'smooth' (white box) and 'detail' (gray box) values, respectively.

FIG. 45  The predict function

FIG. 46  Predict leaves the residual in place of the detail

Fig. 47  The update function

Update preserves the mean by adjusting smooth values

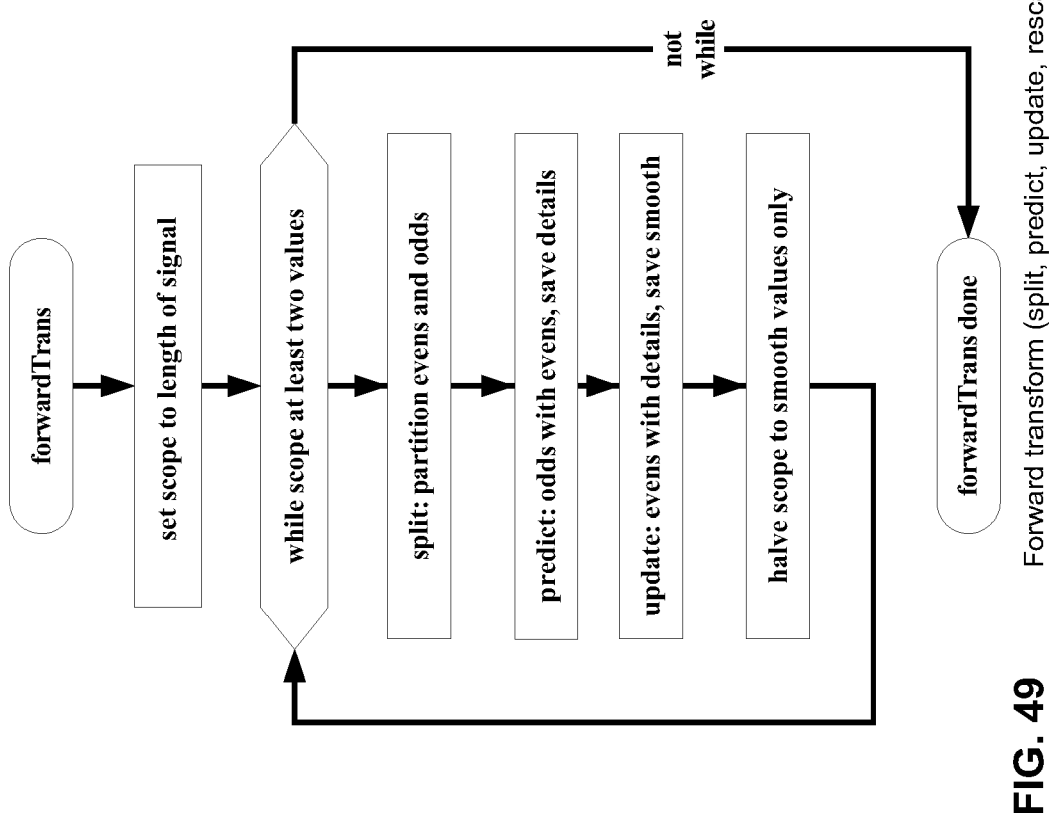
FIG. 49  Forward transform (split, predict, update, rescale)

WAVELET BASED FEATURE EXTRACTION AND DIMENSION REDUCTION FOR THE CLASSIFICATION OF HUMAN CARDIAC ELECTROGRAM DEPOLARIZATION WAVEFORMS

This application claims benefit of U.S. Provisional Patent Application 60/864,861, filed 8 Nov. 2006, the specification of which is hereby incorporated herein by reference.

BACKGROUND OF THE INVENTION

Field of the Invention

The invention relates to a heart monitoring device or a cardio-therapy device providing a heart monitoring feature such as an implantable heart stimulator. Implantable heart stimulators include cardiac pacemakers, cardioverters/defibrillators and the like. The invention further refers to a method of cardiac waveform classification.

A primary task of an implanted cardiotherapy device is the classification of waveforms indicating the electrical activity of the human heart. More particular a task for a pacemaker or implantable defibrillator is the accurate identification of rhythm categories so that the correct electrotherapy can be administered. Because some rhythms cause a rapid dangerous drop in cardiac output, it is necessary to categorize depolarization waveforms on a beat-to-beat basis to accomplish rhythm classification as rapidly as possible.

The basis of intra-cardiac electrogram classifiers in presently implanted devices is comparing the signal amplitude to a threshold and comparing the frequency of threshold crossings to a rate limit.

This method has two main deficiencies:
(1) it is insensitive to the shape (morphological) information indicating the conductive path of a depolarization, and
(2) it is not robust to pseudo-events.

Further prior art solutions include wavelet transformation for waveform analysis and event detection, see, e.g. U.S. Pat. Nos. 6,577,892, 6,135,966, 5,638,823 or 5,439,483.

Prior art solutions analyze the cardiac electrogram (CEGM) using the Haar Wavelet Transform (HWT) and use the Probabilistic Neural Network (see, e.g. US 2005/0071303) or statistical tests equivalent to the rank correlation or binary similarity to perform event classification.

There are several drawbacks to these methods:
(1) The prior art requires frequent hands-on supervision by the clinician of the training phase and retraining phases,
(2) At sampling rates typical for CEGM in implanted medical devices, features spanning only two samples will not be resolved by the Haar wavelet transform if they fall on the odd sample resulting in compromised discrimination between, for example, normal sinus beats and retrograde atrial beats,
(3) The Probabilistic Neural Network requires mathematics that is presently not feasible in implantable medical devices,
(4) rank correlation and binary similarity are coarse categorical statistics with poor specificity.

BRIEF SUMMARY OF THE INVENTION

It is an object of the invention to provide a solution to overcome the aforementioned limitations.

According to the invention, an event waveform classification based on the features generated by the Line Wavelet Transform is proposed.

According to the present invention, a depolarization waveform classifier is based on the Modified lifting line wavelet Transform, Receiver Operating Characteristic, and Kernel Discriminant.

It overcomes problems in existing rate-based event classifiers; namely,
(1) they are insensitive to the conduction path of the heart rhythm and
(2) they are not robust to pseudo-events. Still, the invention is suitable for present limited-resolution platforms that provide an input stream of anti-alias pre-filtered, quantized, threshold-based event detection devices.

The invention is based on the insight that, although rate based methods of event categorization have served well in implanted devices, these methods suffer in sensitivity and specificity when atrial, and ventricular rates are similar. Human experts differentiate rhythms by viewing morphological features on strip-chart like display of electrocardiograms. The wavelet transform is a simple approximation of this human expert analysis function because it correlates distinct morphological features at multiple scales. The accuracy of implanted rhythm determination can then be improved by using human-appreciable time domain features found on multiple time scales.

According to preferred embodiments of the invention, the performance of the Wavelet Transform based classifier has been improved (over prior art) in a number of novel ways that reduce the code space, memory footprint, and current cost to the implant.

Preferably, upon indications of events in the patient's cardiac electrogram (CEGM), the wavelet transform samples the data stream to generate features for reference, confirmation, and evaluation on an ongoing basis. Additional inputs, such as, cardiac motional impedance, cardiac interval, and accelerometer can be combined to modify the confidence that the CEGM event was cardio-dynamically effective. The receiver operating characteristic curve can be used to rank the discriminating power of features accomplishing a reduction to only those that are necessary.

The event classifier has been improved by this invention over prior art in a number of novel ways that reduce the computational costs while maintaining accuracy. The kernel discriminant has replaced the probabilistic neural network (of prior art) and simplifications make it feasible for an implantable medical device. Still, the evaluation accuracy is greater than or equal to 95% on a cohort of 78 IEGM recordings.

The present invention provides for an improved wavelet based feature extraction method and new approaches of dimension reduction for the classification of human cardiac electrogram depolarization waveforms. The method and device discriminates cardiac event types accurately while employing numerous simplifications to enable its implementation within an implantable medical device. The preferred embodiment shows this feature in the context of cardiac rhythm therapy devices.

Prior art solutions also monitor the intra-thoracic impedance (Z) as a proxy for cardiac demand, (autonomic tone due to oxygen/barometric feedback). According to the present invention, impedance measurement may serve as a proxy for cardio-dynamics indicating the depolarization event effectiveness on a beat-to-beat basis. This online secondary indicator is used to modify the confidence of the primary indicator of morphological discrimination between, for example, normal ventricular and a ventricular premature beat with incomplete filling from the atria.

In addition to measuring a proxy for cardio-dynamics, preferred embodiments of the present invention make several improvements on prior art:
(1) By measuring one or more attributes of cardio-dynamics via impedance or intra-cardiac pressure, the present invention is capable of bootstrapping differentiating reference definitions (prototypes) of normal and cardio-dynamically sub-optimal events because online evidence corroborates the contractile response to depolarization. Optimal and sub-optimal heart beats influence cardio-dynamics, thus permitting the binning of all classes of heart beats by cardiac function. Thus, the present invention does not require supervision but is capable of providing to the clinician information at any time from the point of implant,
(2) The present invention applies novel modifications to the Line Wavelet Transform (mLWT) to analyze the CEGM at reduced computational complexity. Unlike the HWT, the mLWT always spans a feature of the CEGM. Besides these two wavelet transforms, however, all others require floating-point calculations to implement,
(3) The present invention employs a novel approach for the attrition and weighting of features for the classifier: (a) the Receiver Operating Characteristic analysis of the WT coefficients and other features produces a single value for each feature that can be used to rank them by classification accuracy, (b) the Kernel Discriminant can be reduced in several ways to allow it to be implemented on an implantable medical device. This leverages the decorrelation of WT coefficients to nullify feature cross-variance reducing the eigenvalue problem of obtaining the Rayleigh quotient to inverting the variances along the diagonal of the Mahalanobis matrix. This method is the least required to be robust to within class variances and still discriminate between classes. Employing these methods with features pruned to <5 computed coefficients resulted in classification accuracies in the high 90s, because the kernel discriminant assumes equal weighting among the features, the ROC analysis method capable of ranking features is required.
(4) The present invention also introduces the Serial Wavelet Forward Transform (SWFT) as a further novel modification of the HWT and the LWT to reduce both the footprint of implementing the a wavelet transform in code space and memory allowing a 1-D streaming input and N desired streaming outputs, such that, classification is complete by the time the depolarization event is over. The wavelet transform is thus optimized so that only the necessary structure to handle streaming input is implemented and does not calculate or allocate memory for values that were never going to be used or are no longer in use.

The invention accepts inputs of concurrent signal streams available in the implantable medical device, as shown in the Event Processing Diagram in FIG. 36. CEGM input is sampled for depolarization events both for indications of an event and to supply samples for decomposition by the wavelet transform. The receiver operating characteristic serves as a feature ranking and reduction layer. Only a select few are passed on to the kernel discriminant for reference definition and event classification.

The simplified wavelet transform (WT) decomposes the CEGM event so that the relative energy associated with a morphological feature is represented in values called coefficients. The modified WT has a number of improvements; note that there are no floating-point calculations involved.

The FIR filter equivalents of the HWT and LWT wavelet smoothing functions are shown in Table 10.

FIG. 30 displays the result of the wavelet transform. A normal sinus and atrial retrograde event can be seen in the upper half of the figure, clearly different to the human eye. In the lower half of the figure, the coefficient values also show that there is some difference between the two events, but not so clearly to the eye. Even if one could perceive the difference in wavelet coefficient values, which few produce the highest accuracy in classification? To answer this question, the Receiver Operating Characteristic is used. This is shown in FIG. 27, where the separability of distributions for a single wavelet transform coefficient corresponds to the area under the ROC curve in the right hand side of the figure. The threshold that best discriminates between two classes of event corresponds to the circle.

As several events are sampled, a distribution of features emerges as represented by the Category Separation curves shown on the left hand side of the figure above. The receiver operating characteristics displayed on the right hand side of the figure, display the relative error from sliding the category separating the threshold across the ADC values. As can be seen by the upper half of the figure, features that poorly separate categories have a smaller area under the ROC curve. The resulting optimal threshold (circle) is farther from a perfect classifier. This feature would be pruned from the discriminant classifier. Features represented by the lower half of the figure are gathered into a tuplet that defines the kernel discriminant. When reference definition is complete, event classification proceeds by decomposing and evaluating only the features in the selected tuplet.

The intra-cardiac electrogram (IEGM) is the waveform indicating the heart electrical activity and provides the implantable therapeutic device with information from which to infer the occurrence of normal and abnormal cardiac events. Perhaps the reader has tied one end of a length of rope to a doorknob and snapped the other end so that a wave travels down the rope. When a depolarization event occurs, a wave of depolarization passes through the 3-dimensional structure of the cardiac tissue similarly. The implanted device can retrieve only a one-dimensional view of this 3-D event as though looking at the pulse going by on the rope described above through a narrow slit. To extend this metaphor slightly, the different sensing configurations of the implanted device will be controlled by the aperture and polarization of this slit.

Justification of Work

Presently, the state of the art for timing-only based event classifications has a highly variable diagnostic accuracy rate of 20% to 90%. Inappropriate therapy may occur in rate-based discriminators of supraventricular tachycardia from ventricular tachycardia. In the existing IEGM event classification systems, definitive morphological classification is absent. Current rhythm classification is so sensitive to ventricular tachycardia, that unnecessary defibrillation of supraventricular tachycardia occurs from 72% to 89% of the time. This unnecessary defibrillation is acceptable to physicians, though not without a small risk of triggering a genuine lethal arrhythmia. Because of memory limitations and processing limitations due to battery capacity of the device, signal recordings of true and false negatives are generally not available for off-line analysis. Therefore, the true incidence of inappropriate classification treatment of timing-only-based methods is unknown.

FIG. 5 illustrates the fundamental weakness of rate-based rhythm classifiers. In the two cases, there is one atrial event for every ventricular event. Two rhythms with similar (non-unique) rates cannot be distinguished when only rate-based information is present.

One rhythm is tolerable (supraventricular tachycardia), while the other is potentially lethal (ventricular tachycardia).

This can be verified by the event markers (those indications of device-based sensing threshold crossings in each chamber shown by the trace along the zero amplitude line going upward for atrial sensed events and downward for ventricular). These two rhythms are occurring at 173 beats per minute for the supraventricular tachycardia and 200 beats per minute for the ventricular tachycardia. However, these rates are not unique enough to distinguish the two rhythms. Only the discernable difference between the two atrial morphologies can reveal the difference between the two rhythms, one of which is potentially lethal.

These devices cannot discriminate between a tolerable or intolerable rhythm of the same rate originating from two different foci in the heart (Bennett, 2002, p. 82). Modern pacemakers (IPG) do not discriminate between normal (antegrade) and abnormal (retrograde) conduction if the rates are similar (Kuck, Cappato, & Siebels, 1996, p. 31). Due to the absence of morphological discrimination, pacemakers and implantable cardio defibrillators (ICD) must reduce or eliminate sensing in two main ways. First these devices attenuate through filtering real-world electromagnetic interference, such as, 60 Hz, 50 Hz, $$\frac{50}{3}$$

Hz power line noise ("EN 45502-2-1," 2004), or skeletal muscle artifact. Second, implants also blank sensing during intra-cardiac interference, such as, artifacts of pacing, afterpotential on the contact elements, far-field sensing in another chamber, or repolarization of the tissue (T-waves).

A drawback is that signals of interest are also undersensed, causing missed detections and the potential for false arrhythmia classifications. Thus, the system must be adjusted, balancing the two main tradeoffs of detections of actual events versus suppression other spurious signal data. For example, the amplitude threshold must be set to a value that accounts for some variation in peak value. Because pacing in these devices produces voltages up to 1000 times the intrinsic signal, the input amplifiers must be blanked in both chambers after pacing until the artifact and afterpotential dissipate from the contact elements. Since the electrical field from one chamber can be sensed remotely from the other chamber, a far-field protection time window discounts events seen during this time to prevent false detection of atrial depolarizations. After the ventricle depolarizes (R-wave), it must repolarize (T-wave) for the next heartbeat. This repolarization is sometimes high enough in amplitude to trip the comparator even after low pass filtering. Using the domain knowledge, these devices also have device refractory periods that parallel the tissue refractory period. In this case, events occurring too soon after the last event must be false because the time expected for the tissue to repolarize has not elapsed.

Because the AV node allows two-way conduction, atrial abnormal events can be generated from ventricular paces. If the atrial abnormal events were then tracked to the ventricle again, Pacemaker Mediated Tachycardia (PMT) results. A Post-Ventricular Atrial Refractory Period (PVARP) prevents the pacemaker from tracking any events that occur during PVARP with a following ventricular pace. Improper adjustment of the above parameters results in oversensing or undersensing, resulting in too many or too few rate-based arrhythmia classifications, respectively. Although present technology is a workable system, the few time critical windows mentioned above are among hundreds that require adjustment, workarounds for side effects, and are fixed in the device by the physician for six months. Morphological classification does not require these refractory windows and thus could reduce system complexity.

It is the purpose of this disclosure to show the feasibility of the implant discriminating two classes of events with 95% accuracy on an IEGM test suite. Morphology-based classification can accurately detect and discriminate many types of events. The multiresolution properties of the wavelet transform resembles the way perception is achieved by humans, in that the visual cortex decomposes stimuli into spatial frequency bands that are approximately octaves (Theodoridis and Koutroumbas, 2003, p. 255).

To discern various classes of events, significant features must be extracted from the IEGM signal. The simplest feature set would be a complete copy of each type of event (number of features equals number of samples) as in Correlation Waveform Analysis. A novel modification of the discrete time linear wavelet (Jensen & La Cour-Harbo, 2001, p. 23) will be used in this work to determine if a subset of the resulting coefficients of the transform can achieve successful discrimination. Although pattern or morphological recognition methods are not new to IEGM classification, a comparison with methods other than wavelet-based classification is not within the scope of this work. Instead, this work will discuss considerations of, modifications to, and demonstrate results of the wavelet transform for feature generation for IEGM classification not found elsewhere.

Rate based methods are the state of the art for rhythm classification due to the constraint of limited processing ability in battery powered implantable devices. This constraint is continually relaxed so that, for example, the computational capabilities of implants include, as of the time of this writing, 8-bit microprocessors. In addition, subthreshold IC design allows low current operation and reduces the drain on the battery capacity of the implant. Improvements in battery technology provide increased energy density per unit volume, also extending device lifetime before replacement. This would seem to make an advanced feature such as morphological classification feasible in the near future.

The object of the invention and further objects are in particular achieved by: a monitoring device for monitoring and evaluation of a physiological signal such as a cardiac electrogram to detect physiological events and/or discriminate physiological events from each other by way of comparison to prototype events, the monitoring device comprises a signal preprocessing stage having an input for a digitized physiological signal being a digital representation of a time course of a physiological signal, the preprocessing stage comprising an event-detector that is adapted to determine a fiducial point for at least one segment of the physiological signal by detecting reoccurring characteristic features within the physiological signal such as R-waves or p-waves, the monitoring device further comprises a wavelet coefficient generation stage that is adapted to perform a modified lifting line wavelet transformation to thus generate wavelet transformation coefficients as features of the digitized physiological signal, a feature evaluation stage that is adapted to perform a reduction of features of the digitized physiological signal by selecting those wavelet transformation coefficients that have been determined to be most characteristic for discriminating a prototype event from a regular event by means of a receiver operation characteristics curve analysis a feature threshold memory comprising a threshold value for each selected feature of a prototype event, the threshold value being determined by means of the receiver operation characteristics curve analysis and a comparator stage connected to the threshold memory and being adapted to compare the selected features of an actual digitized physiological signal to corresponding threshold values for a prototype event and to assign the actual digitized physiological signal to the prototype event if each or a majority of the selected features of the actual digitized physiological signal is within the threshold defined by a corresponding one of the stored threshold values.

It should be noted, that according to the invention the characteristic features of the digitized physiological signal are the wavelet (detail) coefficients resulting from a modified line wavelet transformation of this signal.

Instead of the lifting line wavelet transformation any other discrete wavelet transformation could be used at the expense of more computational power required. Non-obvious improvements to the line wavelet algorithm are disclosed in the detailed disclosure hereinafter and refer to the starting on index and to the boundary treatment.

A further improvement resulting from the invention is given by the fact, that the wavelet transformation can be aborted if all significant, most characteristic features as defined by the receiver operation characteristics analysis already are determined when calculating the wavelet (detail) coefficients for a first or a number of first scaling (smoothing) coefficients.

Preferably, the wavelet coefficient generation stage is adapted to perform the lifting line wavelet transformation based on a high pass detail filter and a corresponding low path smoothing filter to thus obtain wavelet detail and scale coefficients, respectively.

Further, the wavelet coefficient generation stage may be adapted to perform the lifting line wavelet transformation recursively the thus obtain further wavelet detail coefficients for a next scale based on scale coefficients determined while determining detail coefficients for a previous scale. This recursive procedure can be aborted as soon as all characteristic feature required for prototype event assignment are determined.

In a further preferred embodiment, the processing stage has at least one further input for further input values, such as an accelerometer value or cardiac impedance values.

In such embodiment, the processing stage can be adapted to generate a feature vector from the wavelet coefficients produced by the wavelet coefficient generation stage and the further input values for further processing by the feature evaluation stage, see, e.g. FIG. 36.

The feature evaluation stage preferably is adapted to perform feature evaluation in relation to a fiducial point of each signal segment to be evaluated.

For determining the threshold values for feature comparison according to the invention it is preferred that the monitoring device comprises a threshold determination stage comprising a receiver operation characteristics analyzer that is adapted to process features (wavelet coefficients) of a regular event and a prototype event that are time aligned with each other based on the fiducial point to thus determine the most characteristic features and to further determine and store a threshold value for each of the most characteristic features in the threshold memory. The threshold determination stage is not needed for online feature analysis but for initial setup of the monitoring device. Therefore, the receiver operation characteristics analyzer can be implemented in an independent device that only temporarily is connected to the other parts of the monitoring device.

In order to be able to discriminate between more than one pair of event (e.g. regular event and supraventricular tachycardia event) the threshold memory may comprise more than one set of threshold values wherein each the of threshold values best separates each of the features of a particular event into categories, such as regular or prototype, and wherein the comparator stage is adapted to compare the selected features of an actual digitized physiological signal to corresponding threshold values for each prototype event separately. According to this embodiment, event discrimination always is to be carried out event by event.

To be able to discriminate using a plurality of features simultaneously (as opposed to X-out-of-Y) or to discriminate between a plurality of events simultaneously, the comparator stage may comprise a kernel discriminant analyzer adapted to perform a kernel discriminant analysis on the selected features of an actual digitized physiological signal to assign the selected features of an actual digitized physiological signal to one of a plurality of prototype events used to determine a kernel discriminant for discrimination between the prototype events.

The object of the invention also is achieved by a heart therapy system comprising an implantable heart stimulator and an external device, wherein
the implantable heart stimulator comprises a signal sensing stage and
a signal preprocessing stage having an input for a digitized physiological signal being a digital representation of a time course of a physiological signal, the input being connected to the sensing stage,
the preprocessing stage comprising an event-detector that is adapted to determine a fiducial point for at least one segment of the physiological signal by detecting reoccurring characteristic features within the physiological signal such as R-waves or p-waves
the external device comprises:
a wavelet coefficient generation stage that is adapted to perform a lifting line wavelet transformation to thus generate wavelet transformation coefficients as features of the digitized physiological signal,
a feature evaluation stage that is adapted to perform a reduction of features of the digitized physiological signal by selecting those wavelet transformation coefficients that have been determined to be most characteristic for discriminating a prototype event from a regular event by means of a receiver operation characteristics curve analysis
a feature threshold memory comprising a threshold value for each selected feature of a prototype event, the threshold value being determined by means of the receiver operation characteristics curve analysis and
a comparator stage connected to the threshold memory and being adapted to compare the selected features of an actual digitized physiological signal to corresponding threshold values for a prototype event and to assign the actual digitized physiological signal to the prototype event if each or a majority of the selected features of the actual digitized physiological signal is within the threshold defined by a corresponding one of the stored threshold values.

In such heart therapy system an implantable heart stimulator preferably comprises a signal sensing stage,
a signal preprocessing stage having an input for a digitized physiological signal being a digital representation of a time course of a physiological signal, the input being connected to the sensing stage, the preprocessing stage comprising an event-detector that is adapted to determine a fiducial point for at least one segment of the physiological signal by detecting reoccurring characteristic features within the physiological signal such as R-waves or p-waves and an event detecting stage comprising a wavelet coefficient generation stage that is adapted to perform a modified lifting line wavelet transformation relative to a fiducial point of a respective segment of the physiological signal to thus generate wavelet transformation coefficients as features of the digitized physiological signal, a feature evaluation stage that is adapted to perform a reduction of features of the digitized physiological signal by selecting those wavelet transformation coefficients that have been determined to be most characteristic for discriminating a prototype event from a regular event by means of a receiver operation characteristics curve analysis a feature threshold memory comprising a threshold value for each selected feature of a prototype event, the threshold value being determined by means of the receiver operation characteristics curve analysis and a comparator stage connected to the threshold memory and being adapted to compare the selected features of an actual digitized physiological signal to corresponding threshold values for a prototype event and to assign the actual digitized physiological signal to the prototype event if each or a majority of the selected features of the actual digitized physiological signal is within the threshold defined by a corresponding one of the stored threshold values whereas an external device comprises a threshold determination stage comprising a receiver operation characteristics analyzer that is adapted to process features (wavelet coefficients) of a regular event and a prototype event that are time aligned with each other based on the fiducial point to thus determine the most characteristic features and to further determine and a threshold value for each of the most characteristic features to be in the threshold memory of the implantable heart stimulator.

The information concerning a fiducial point in a segment of the physiological signal generated by the preprocessing stage can be fed a an input signal to the wavelet coefficient generation stage.

The wavelet coefficient generation stage preferably is adapted to perform a line wavelet transformation that is modified in order to save processing effort. The modifications include a Serial Wavelet Forward Transform that implements only the portion of the modified lifting line wavelet transformation that is necessary to produce the few coefficients needed. Further modification include starting on index and the boundary treatment as is disclosed in further detail later herein.

The features that characterize a signal segment and that are used for comparison with prototype events include a selected number of wavelet transform coefficients and may preferably further include a heart rate value generated by the device and/or an output signal of an accelerometer corresponding to the signal segment to be categorized.

Further features to be considered and processed by the device include: Cardiac impedance that provides corroboration of cardio-dynamically regular and prototype events. This online secondary indicator fan be used to modify the confidence of the primary indicator of morphological discrimination between, for example, normal ventricular and a ventricular premature beat with incomplete filling from the atria.

Preferably, discrimination among more than two feature is performed by means of a kernel discriminant. The kernel discriminant preferably is optimized for use in a medical implant having limited resources. Therefore, the kernel discriminant preferably is improved by feeding it a select few features pre-ranked by the receiver operation characteristics analyzer.

The sensing stage preferably comprises a band path filter having a pass band between 5 Hz and 100 Hz. Further, the sensing stage preferably is adapted to be connected or is connected to a bipolar electrode lead.

The object of the invention also is achieved by a heart stimulator that comprises a signal sensing stage and a monitoring device as disclosed above, wherein the input of the preprocessing stage is connected to the sensing stage. The heart stimulator can be an implantable pacemaker and/or an implantable cardioverter/defibrillator.

Further, the object of the invention is achieved by a method for monitoring and evaluation of a periodic or quasi-periodic signal such as a cardiac electrogram to detect physiological events and/or discriminate physiological events from each other by way of comparison to prototype events. The method comprises the steps of:

signal preprocessing to determine a fiducial point for at least one segment of the physiological signal by detecting reoccurring characteristic features within the physiological signal such as R-waves or p-waves, wavelet coefficient generation by means of a modified lifting line wavelet transformation to thus generate wavelet transformation coefficients feature evaluation including reduction of features of the digitized physiological signal based on the wavelet transformation coefficients by means of receiver operation characteristics curve analysis to determine a reduced set of most characteristic wavelet coefficients and feature comparison to compare the reduced set of wavelet coefficients to one or more stored reduced sets of wavelet coefficients, each stored reduced set of wavelet coefficients corresponds to a prototype event.

Further advantageous details can be taken from the following extensive disclosure.

Main Results

This disclosure shows the application of the line wavelet transform to IEGM classification using methods from different fields: the biosignal source from the medical implant industry, the wavelet transform from digital signal processing, and receiver operating characteristic curve from statistics.

There are many rhythm classes, but each can be reduced to successive events originating from a normal or abnormal focus of cardiac tissue. In most rhythms, except fibrillation, the shape information identifying the focus usually changes slowly if at all. Therefore, when the IEGM enters a new rate category, it is sufficient to identify the event shape to determine its origin and therefore the rhythm class.

Table 1 shows the important rhythms to identify and their component events (rate and shape). Complex timing algorithms are capable of distinguishing between these rhythm classes much of the time. However, when atrial and ventricular rates are not significantly different, the last three rhythms are poorly differentiated. Notice in the table that the rate categories are elevated for all three. Morphological (shape) analysis, on the other hand, definitively categorizes these rhythms by identifying the focus of component events. Presently, shape analysis is still done off-line by inspection and is not real time. Presently, in the implant, rhythm classification occurs when some rate-based x out of y criterion is satisfied, for example, 3 fast event intervals out the last 8. This work demonstrates the feasibility of providing such an implanted rhythm classification system with categorizations of events based on morphological features indicating origin and pathway resulting in improved accuracy.

The results for proofing the disclosed concept were obtained by off-line analysis of pre-recorded data in a computer-based model of an implantable device. The work performed demonstrates that a quantized version of the wavelet transform (WT) can produce features capable of accurately classifying salient events in the human intra-cardiac electrogram. A method of classifier-independent feature selection is used in this work to demonstrate efficacy. The work shows that the wavelet transform coefficients (WTC) can be reduced in number (to a single coefficient) and still achieve high accuracy for organized rhythms.

BRIEF DESCRIPTION OF THE DRAWINGS

The above and other aspects, features and advantages of the present invention will be more apparent from the following more particular description thereof, presented in conjunction with the following drawings wherein:

FIG. 37 shows the sliding and scaling allows resolution of all points of.

FIG. 49 shows the forward transform (split, predict, update, rescale).

Figure 1:
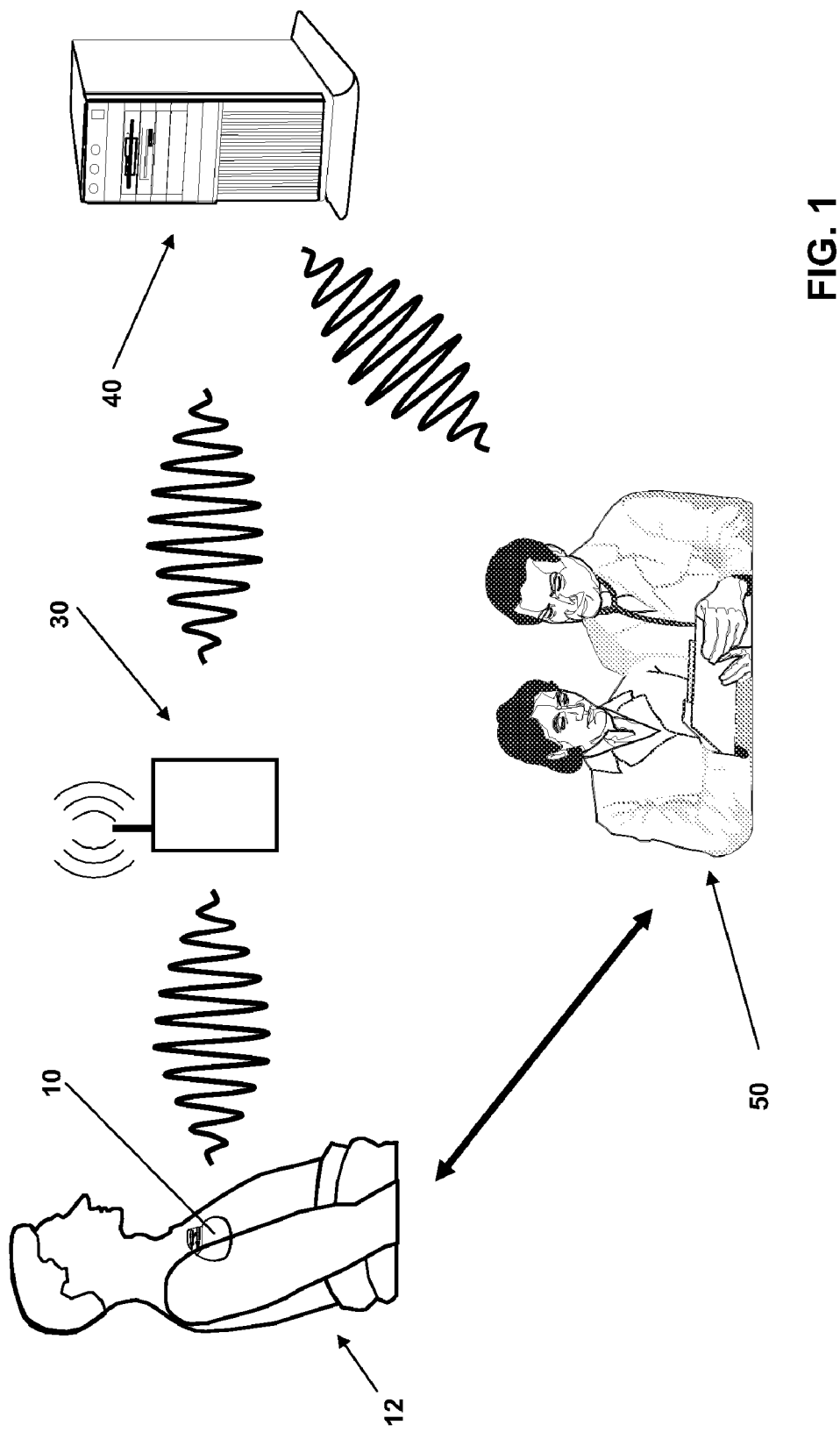
FIG. 1 shows a typical therapy environment including an implantable medical device, an external device and a service center.

The disclosure also refers to the following tables:

Table 1. Key rhythms to classify in an implantable pacemaker or defibrillator can be characterized by rate, but are more accurately discriminated by shape.

Table 2. Terms regarding lead tip polarity in pacing and sensing (Dorland, 2003).

Table 3. Complexities of the three most basic wavelets make clear the rapidly increasing computational complexity.

Table 4. Definition of parameters used in the generation of the ROC curve.

Table 5. The peak magnitude is aligned in the buffer.

Table 6. LWT Processing cost is estimated on a microprocessor and a DSP.

Table 7. Patient data summary by event discrimination task.

Table 8. The assessment methodology.

Table 9. Mean evaluation accuracies for the event categories by WTC sub bands.

Table 10. FIR filter equivalent of the HWT and LWT wavelet smoothing functions

In the disclosure, the following abbreviations and symbols are used:

ADC: Analog-to-digital converter.
AUC: Area under receiver operating characteristic curve.
BP: Band pass (filter).
DSP: Digital Signal Processor.
HP: High pass (filter).
ICD: Implantable cardioverter defibrillator.
IEGM: Intracardiac electrogram.
IPG: Implantable pulse generator, a pacemaker.
LCL: Lower confidence limit.
LP: Low pass (filter).
LWT: [Discrete Time Integer Valued] Line Wavelet Transform.
NSR: Normal sinus rhythm, a healthy rhythm.
ROC: Receiver operating characteristic.
§: Section sign.
ST: Sinus Tachycardia: normal acceleration after exertion, no treatment.
SVT: Supraventricular rhythm: non-lethal, treated with pacing not shock.
VT: Ventricular tachycardia, a potentially lethal rhythm.
WT: The wavelet transform.
WTC: Wavelet transform coefficient(s).

DETAILED DESCRIPTION OF THE INVENTION

The following description is of the best mode presently contemplated for carrying out the invention. This description is not to be taken in a limiting sense, but is made merely for the purpose of describing the general principles of the invention. The scope of the invention should be determined with reference to the claims.

Disclosure Organization

This disclosure is organized as follows.

In Chapter 1, an exemplary embodiment of a monitoring device in form of an implantable cardiac pacemaker is described.

In Chapter 2, the coupling in the heart between the electrical excitation and the resulting mechanical event will be explained. A history and basic concepts of IEGMs are given. There is a concise description of how IEGM signals are pre-processed in IPGs and ICDs, and how the results are used by present technology. Various terms used in heart rhythm intervention technology are presented and defined. The difference between time-based and morphology based classification is discussed. This section explains the difference between an normal and abnormal event, and the possible consequences of misclassification.

In Chapter 3, the wavelet transform is described. Orthogonality is explained. How the buffered time samples are processed to become WTC is explained. The limitations of finite resolution, sampling rate, and noise are discussed. In addition, the use of WTC as features for IEGM classification is introduced. This chapter proposes a method of feature evaluation and pruning, that is, the use of the receiver operating characteristic (ROC) curve to evaluate the effectiveness of WTC as features.

In Chapter 4, the lifting version of the line wavelet transform is described. Event detection and time buffering are discussed as methods necessary to process the IEGM before wavelet feature extraction can occur. The methods to adapt the wavelet transform itself to decompose discrete valued IEGMs into features on the target application are presented. In Chapter 5, the results of using wavelet transform coefficients for event discrimination are presented.

Chapter 6 concludes with a discussion of the contributions.

In Chapter 7 a preferred embodiment of the line wavelet transform is disclosed.

Chapter 1

Exemplary Embodiment

The therapy system depicted in FIG. 1 comprises an implantable medical device 10 which is a dual chamber pace maker implanted into a patient 12. The therapy system further comprises an external device 30 and a service center 40. The implantable medical device 10 and the external device 30 allow for a short-range wireless data communication for data exchange between implantable medical device 10 and the external device 30. External device 30 serves as a relay station between the implantable medical device and a central service center 40. Thus, data may be exchanged between the implantable device 10 and the central service center 40. A physician 50 attending a patient thus can access all the data provided by the implantable medical device 10 via the central service center 40.

As will be more apparent from the following description of the implantable medical device 10, the implantable medical device 10 is capable of making up intracardiac electrograms that represent an electrical activity of the myocardium of either a right atrium or a right ventricle of a heart. According to further embodiments not represented in detail within this disclosure the implantable medical device could also be capable of picking up intracardiac electrograms for the left atrium and/or or the left ventricle. Further, the implantable medical device can be made capable of creating a far field electrogram signal from intracardiac electrogram signals picked up via intracardiac electrodes connected to the implantable medical device 10.

Figure 2:
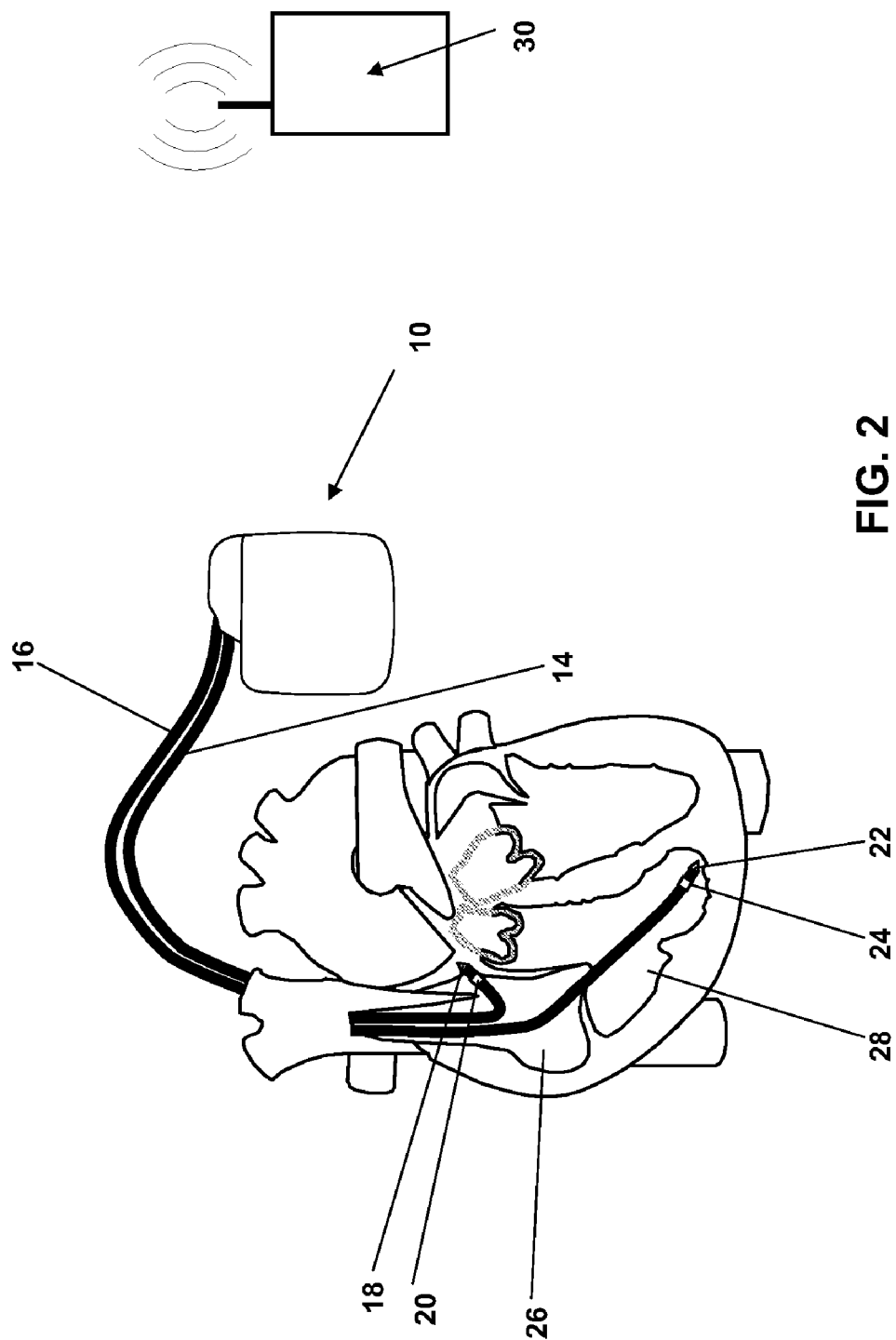
FIG. 2 shows a detailed representation of the implantable medical device by way of an exemplary implantable dual chamber pace maker in conjunction with the external device.
Figure 3:
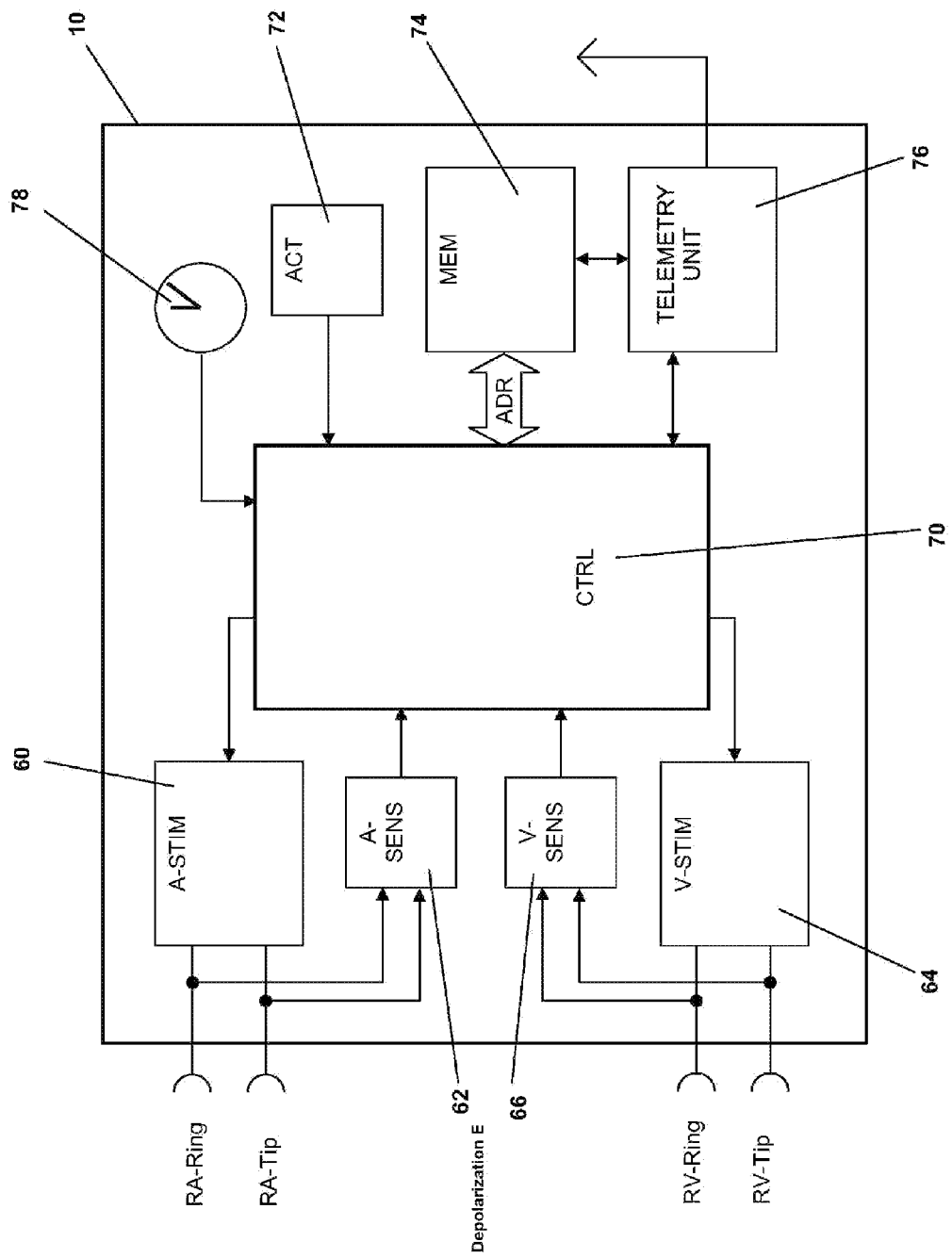
FIG. 3 shows a schematic block diagram of the implantable medical device of FIG. 2.

In order to be capable to pick up electric potentials of the myocardium, the implantable medical device 10 (dual chamber pace maker 10) of FIG. 2 is connected to electrode leads 14 and 16 comprising a stimulation and sensing electrodes 18 and 20 and 22 and 24 respectively. Electrodes 18 and 20 are placed in the right atrium 26 of the heart whereas electrodes 22 and 24 are placed in the right ventricle 28 of the heart.

Atrial electrode lead 14 is connected to an atrial stimulation unit 60 and an atrial sensing unit 62. Ventricular electrode lead 16 is connected to a ventricular stimulation unit 64 and a ventricular sensing unit 66. Both the atrial stimulation unit 60 and the ventricular stimulation unit 64 are adapted to generate atrial or ventricular stimulation pulses, respectively for stimulation the respective heart chamber. The atrial sensing unit 62 and the ventricular sensing unit 66 are adapted to process electric potentials picked up wire a pair of atrial ectrodes 18 and 20 or the pair of ventricular electrodes 22 and 24, respectively. Atrial electrode 18 and atrial electrode 20 is a right atrial ventricular electrode. Similarly, ventricular electrode 22 is a right ventricular tip electrode and electrode 24 is a right ventricular ring electrode.

Atrial stimulation unit 60, atrial sensing unit 62, ventricular stimulation unit 64 and ventricular sensing unit 66 are connected to a control unit 70 of the implantable medical device 10. Control unit 70 is further connected to an activity sensor 72 which for example can be an accelerometer. Further, control unit 70 is connected to a timer 78 providing a time signal. Control unit 70 is also connected to a memory 74 that can serve for storing data such as data representing electrograms or programs controlling control unit 70. Finally, control unit 70 is connected to a telemetry unit 76 that is adapted to allow a wireless data communication between implantable medical device 10 and the external device 30.

Control unit 70 is adapted to process intracardiac electrogram signal as described hereinafter in more detail and as claimed by the claims.

Figure 4:
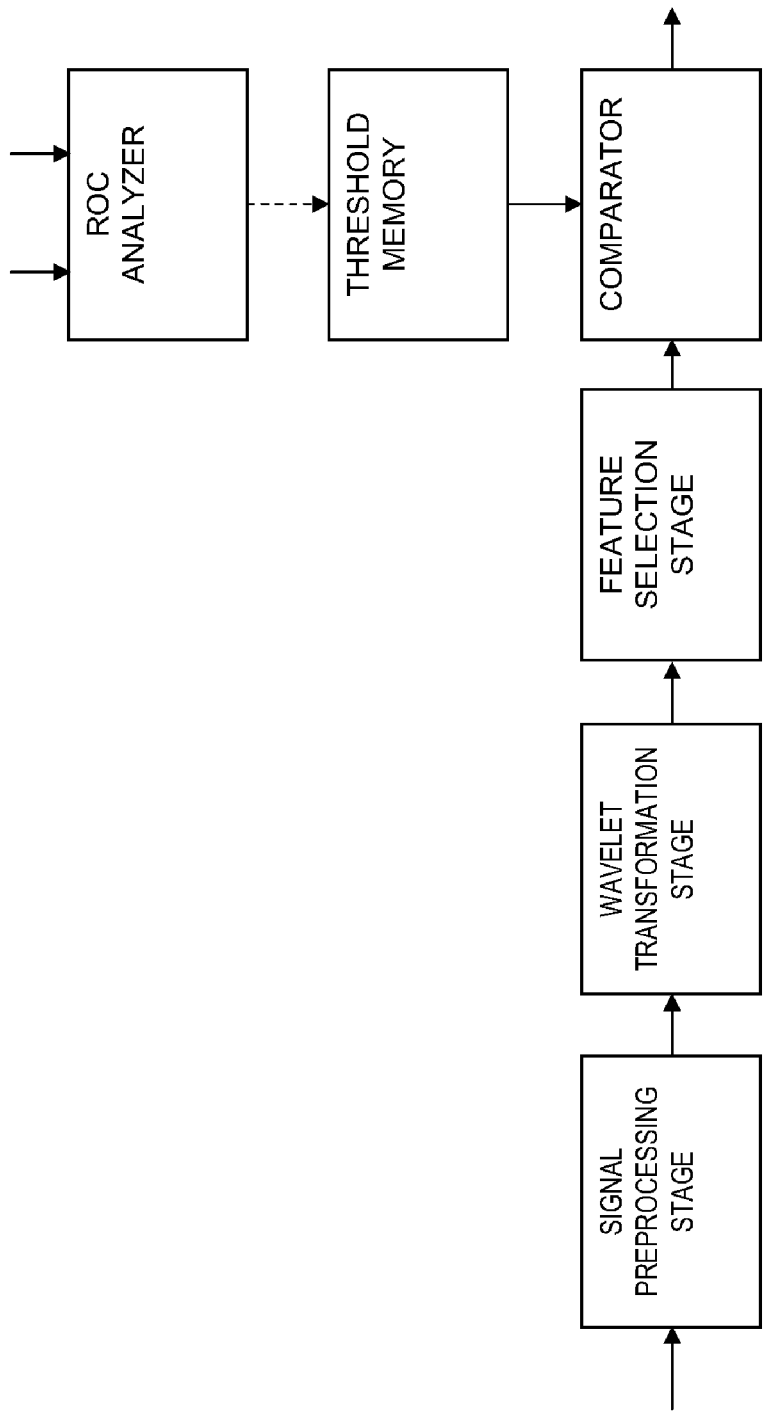
FIG. 4 shows a schematic block diagram of an exemplary embodiment of a monitoring device according to the invention.
Figure 5:
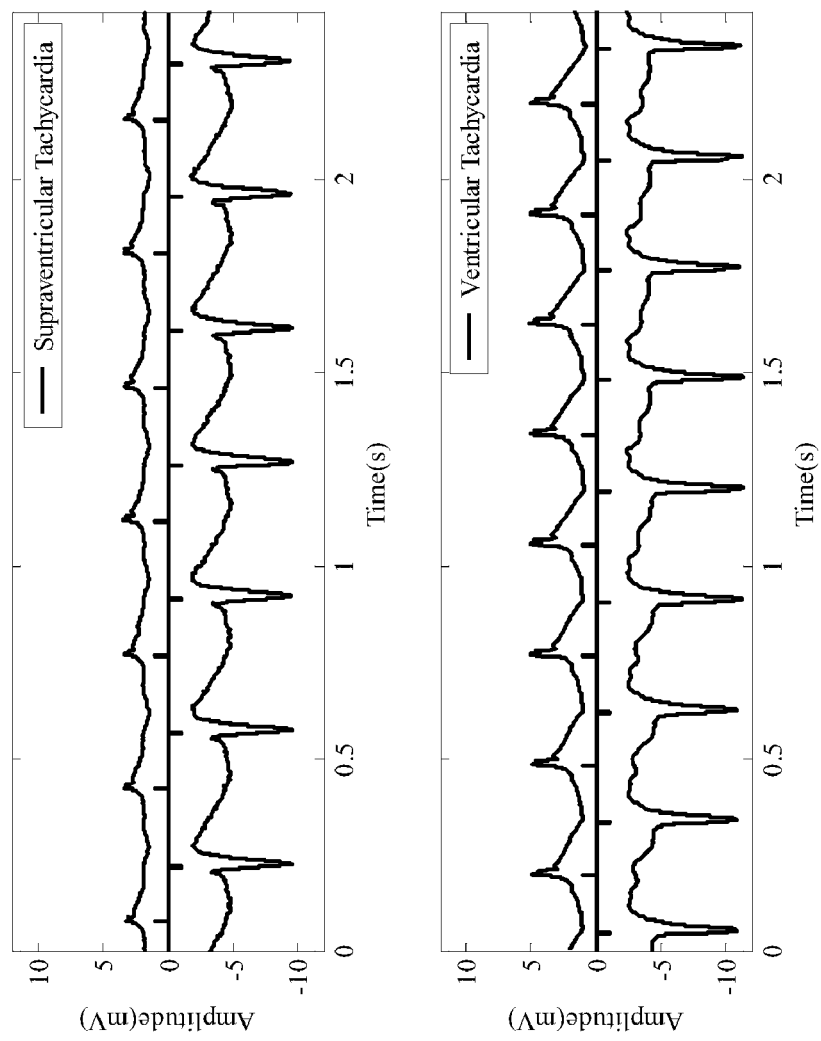
FIG. 5 shows two rhythms with similar (non unique) rates cannot be distinguished when only rate based information is present.

FIG. 4 shows the basic features of the monitoring device that can be implemented within control unit 70 of implantable heart stimulator 10 or that can partly be made a part of the implantable heart stimulator 10 and partly be implemented with the external device 30 or the service center 40. Those parts of the monitoring device that are needed for online-event detection preferably are made part of control unit 70 of the implantable heart stimulator 10. These parts include a signal preprocessing stage, a wavelet transformation stage, a feature selection stage and a comparator that are arranged one after another. The comparator has access to a threshold memory that should also be part of the implantable heart stimulator 10. The signal preprocessing stage may include or be part of the sensing stage such as atrial sensing stage 62 or ventricular sensing stage 66. Signal preprocessing includes detection of R-waves or p-waves. This kind of detection also is called "event detection" in the further disclosure. At this point it should be noted that the term "event detection" has a double meaning in this disclosure. First, it refers to the simple event detection that is detection of R-waves or p-waves for determining fiducial points of the signal. Secondly, event detection can also mean the assignment of a certain signal to a prototype event such as regular event, supraventricular tachycardia and the like. That kind of event detection is performed by means of the wavelet transformation stage and the feature selection stage. The transformation stage generates wavelet coefficients, that are also called detail coefficients for further processing by the feature selection stage. The wavelet transformation stage simultaneously generates scaling or smoothing coefficients that are used for recursive calculation of further detail coefficients. This is illustrated in more detail hereinafter. The feature selection stage only selects those wavelet coefficients that previously have been determined to be the most characteristic ones. The comparator compares these selected wavelet coefficients to threshold values stored in the threshold memory. The threshold values are previously determined by means of a receiver operation characteristics analyses when the most characteristic features are determined.

This kind of receiver operation characteristics analyses is part of an initialization process for setting up the monitoring device. For this purpose, a receiver operation characteristics analyzer (ROC analyzer) is used. This ROC analyzer can be arranged outside the implantable heart stimulator since it is only needed initially or from time to time. The receiver operation characteristics analyzer processes two sets of wavelet coefficients. A first set of wavelet coefficients corresponds to a regular signal whereas a second set of wavelet coefficients corresponds to a particular prototype event signal such as a signal in case of supraventricular tachycardia. The receiver operation characteristics analyzer basically compares the two sets of the wavelet coefficients (or feature vectors) in order to determine those corresponding features (wavelet coefficients) that discriminate the regular event from the prototype event. These are the most characteristic features. For each of the most characteristic features thus selected the receiver operation characteristics analyzer also determines a threshold value. A threshold value serves for categorizing each feature as belonging to a regular event or a prototype event. If all features of an actual signal (that is the wavelet coefficients of an actual signal) can be assigned to a particular prototype event, this prototype event is detected by the monitoring device.

Chapter 2

Background

To understand the role of morphological identification of the IEGM, some background of cardiac anatomy, electrophysiology, and pathology will be presented. The purpose of this chapter is to explain briefly the basic function of the heart and its electrical control mechanism. Variances from these descriptions occur between individuals or within individuals over time, due to normal development or pathologies.

Anatomical Description of the Heart

Figure 6:
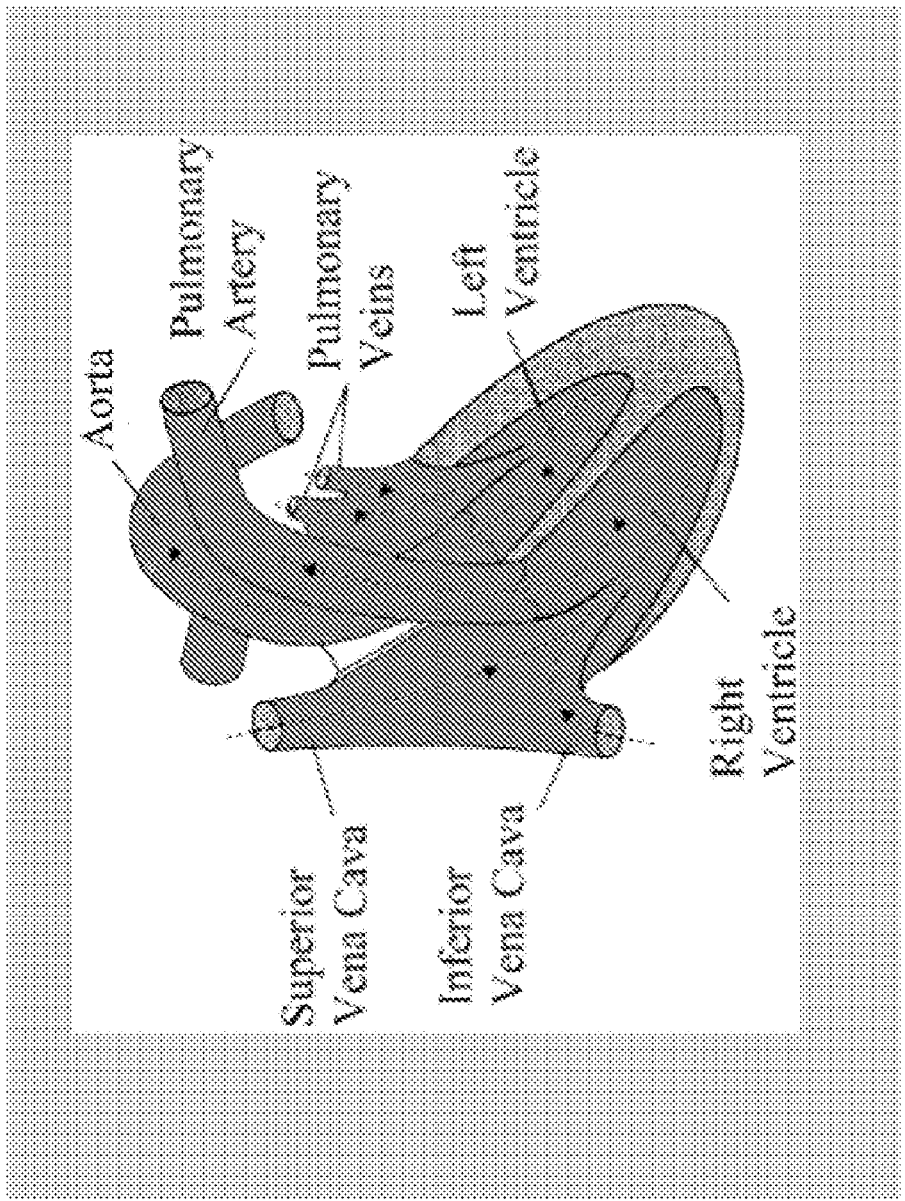
FIG. 6 shows the Cardiac blood flows in the direction of the arrows.

The heart is located in the chest cavity horizontally left between the sternum and the axilla, vertically behind the left pectoral, and anterior. The major axis of the ellipsoid-shaped organ runs from the upper right to lower left thorax. Large vessels connect to upper right end of the heart. FIG. 6 shows a simplified cross-section of the heart in anatomical frontal view. The Vena Cava collects de-oxygenated blood (anatomical right) returning from the body. The pulmonary artery carries oxygen depleted blood to the lungs. The pulmonary veins collect re-oxygenated (anatomical left) blood from the lungs. The aorta supplies re-oxygenated blood to the body.

Blood collection occurs in chambers of contractile tissue or myocardium (gray). The two major cavities are right and left. These larger cavities are further divided into upper (atria) and lower (ventricle) chambers separated by one-way valves. The valves permit flow only in the direction of the arrows. Additional valves at the outlet of the ventricles also permit one-way flow to the lungs and body.

The heart is a pump connected to the vascular system ensuring continuous supply of oxygen and nutrients and the removal of byproducts of metabolism. Oxygen depleted blood from the body collects in the right atrium, and passes through the valve. When blood fills a chamber, it pre-loads (stretches) the tissue building elastic energy for the contraction. Contraction raises the pressure inside the chamber, causing the inflow valve to close. The outflow valve opens when the pressure gradient across the valve is greater than zero. The chamber empties until the pressure equalizes on both sides of the outflow valve, whereupon it closes. Thus, the right ventricle contracts and pushes the blood out through the lungs. Re-oxygenated blood is collected in the left atrium, and passes through the valve. As the left ventricle contracts, it pushes the blood out to the systemic circulation. The vascular system narrows to arteries, arterioles, capillaries where oxygen and nutrients are exchanged for carbon dioxide and metabolic by products (Thubrikar, 1990, p. 1). The vascular system then progressively enlarges from venules to veins returning to the vena cava.

Electrical System of the Heart

Figure 7:
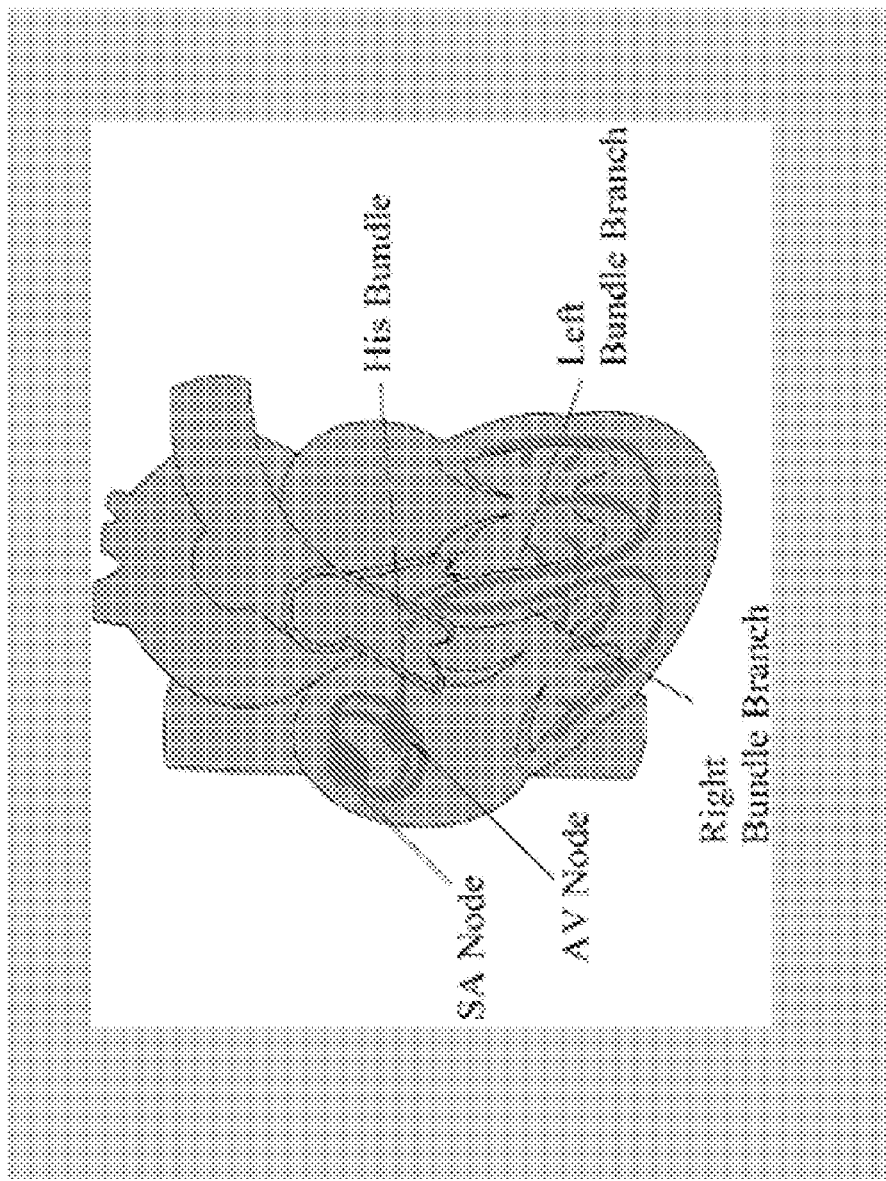
FIG. 7 shows the Natural pacemaker and conduction system.

Under resting conditions, the entire myocardium contracts rhythmically 60-90 beats per minute resulting in the pumping of blood throughout the body. The myocardium is composed of individual cells (myocytes) that contract when stimulated by an electrical signal emanating from the intrinsic pacemaker, the Sino-Atrial node. This signal is generated and conducted by a network of specialized myocytes that are capable of spontaneous contraction. In FIG. 7, the Sino-Atrial node (SA node) and the rest of the conducting system is shown. Normally, excitation for one cardiac cycle begins in the SA node and is conducted by specialized cells (the central root-like structure) to the atrio-ventricular node (AV node). This electrical conduction system splits into two main branches, right and left. From there, the specialized cells form a fine root-like structure reminiscent of a horsetail (shown conceptually) called Purkinje fibers.

Timing Sequence of Electrical Excitation

Figure 8:
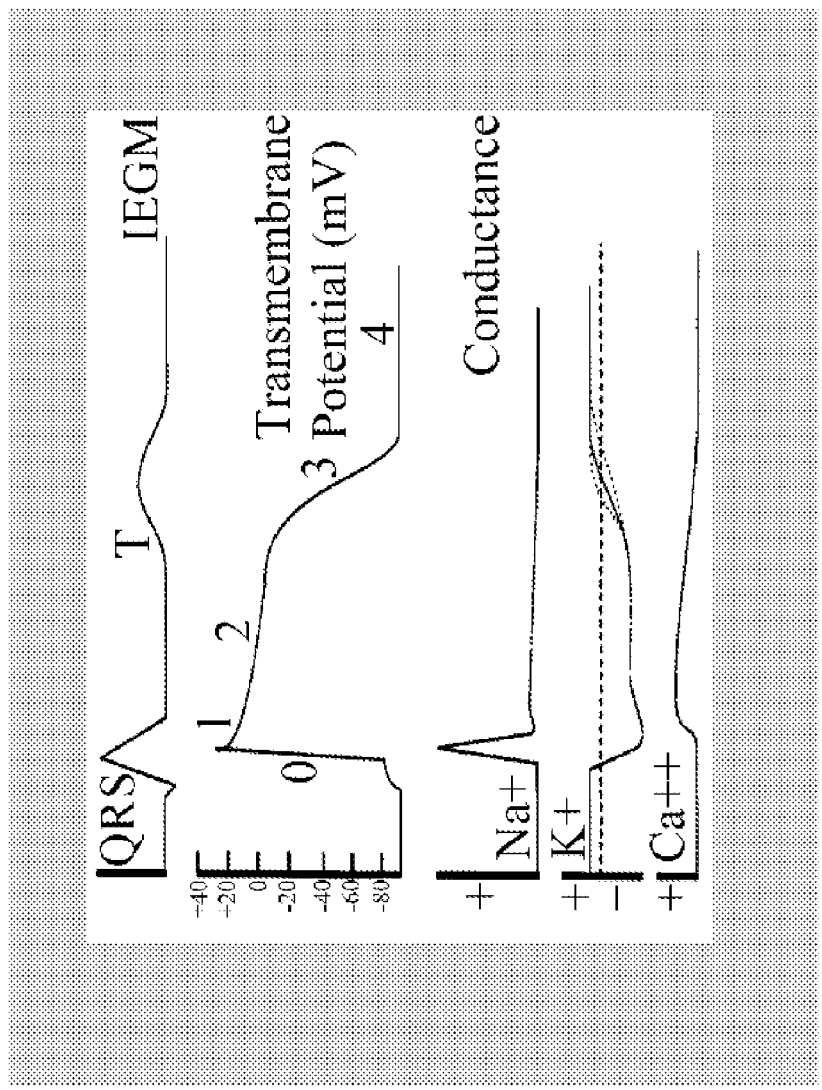
FIG. 8 shows the IEGM results from ion flow across the cell membrane and the resulting transmembrane potential.

All myocytes are electrically excitable; however, the cardiac conduction system is composed of specialized cells that excite at a higher rate than working tissue. The larger mass of cells in the heart will follow the fastest rate available, resulting in synchronized activity, and effective contractions (Chadwick & Goode, 2003, p. 11). FIG. 8 is arranged as follows. The horizontal axis is time and the scale is a single heart cycle. The top trace is the IEGM showing the depolarization event ('QRS') and the repolarization event ('T' for 'T-wave').

The second trace down shows the transmembrane ('action') potential and its phases with the vertical scale in millivolts. The bottom three traces show that cell membrane conductance is the passage of ions through the cell membrane as a function of time during a heart cycle. Here, the vertical scales show relative net concentration of ion from inside the cell with respect to the outside. Prior to excitation, the inside of the myocyte is −90 mV with respect to the outside of the cell. Potassium ($K^+$) passively diffuses out of the cell (Phase 4 of FIG. 8). The net charge across the cell membrane is reversed briefly (depolarization or Phase 0). This occurs in the working myocytes only when stimulated by an external stimulus, such as, a neighboring or specialized cell. The result is the transmembrane potential seen in the figure. The ions sodium ($Na^+$) and calcium ($Ca^{++}$) move into the cell maintaining a positive potential with respect to the outside (Phase 2), and then are pumped back outside of the cell during repolarization (Phase 3) restoring the resting potential.

The cell is refractory (unresponsive) to stimulus during Phases 0-2, and becomes partially refractory by Phase 3. By Phase 4, the cell is fully excitable again. This assures that the mechanical event resulting from depolarization has time to complete before a new depolarization can occur. A band of refractory tissue in the wake of depolarization prevents the wavefront from looping back onto the repolarized (excitable) tissue that follows. In the normal heart, this maintains the overall coordination of working cells by preventing the emergence of re-entrant loops.

Normal Conduction Sequence

Figure 9:
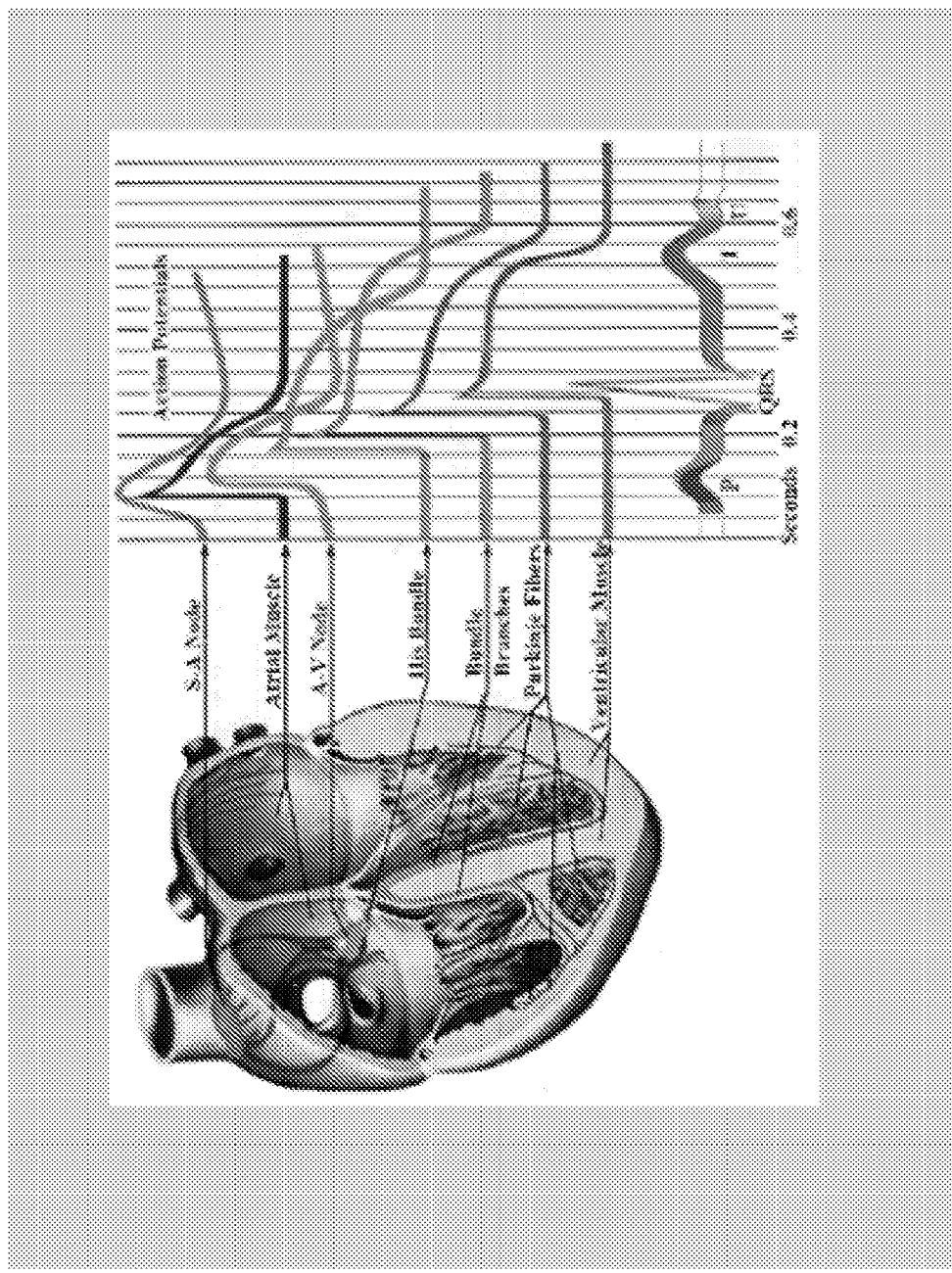
FIG. 9 shows that the action potentials vary with tissue type.

FIG. 9 shows the surface electrocardiogram that results from the superposition of the action potentials generated at various points in the conduction system and working myocardium. The specialized cells capable of spontaneously generating a transmembrane potential are known as autorhythmic. The resting potential of autorhythmic cells is not flat, but leaks sodium slowly into the cell, gradually causing the transmembrane potential to be less negative (small bump before Phase 0). See:

This spontaneous depolarization is the cause of the automaticity of the SA node. When the threshold is reached, the full action potential occurs (sharp upstroke of Phase 0). The rate of this leakage current varies with different parts of the conduction system, the SA node being the fastest, causing the SA node to be the dominant event generator in the heart. In contrast, the resting potential of working myocytes is steady, causing them to wait for an external stimulus. From the top of FIG. 9 down, the signals shown represent the sequence of electrical events that result in a single normal contraction. The superposition of these waveforms results in the IEGM trace at the bottom of the figure. The SA node and working atrial muscle signals aggregate to produce the P-Wave. The AV node acts as a delay element to allow time for the resulting mechanical pumping of the atrium. The Bundles, Fibers, and working ventricular muscle signal add to produce the QRS. The T-wave is the repolarization of the ventricle (the atrial repolarization is obscured by the QRS).

The Coupling of Electrical Excitation and Contraction

Figure 10:
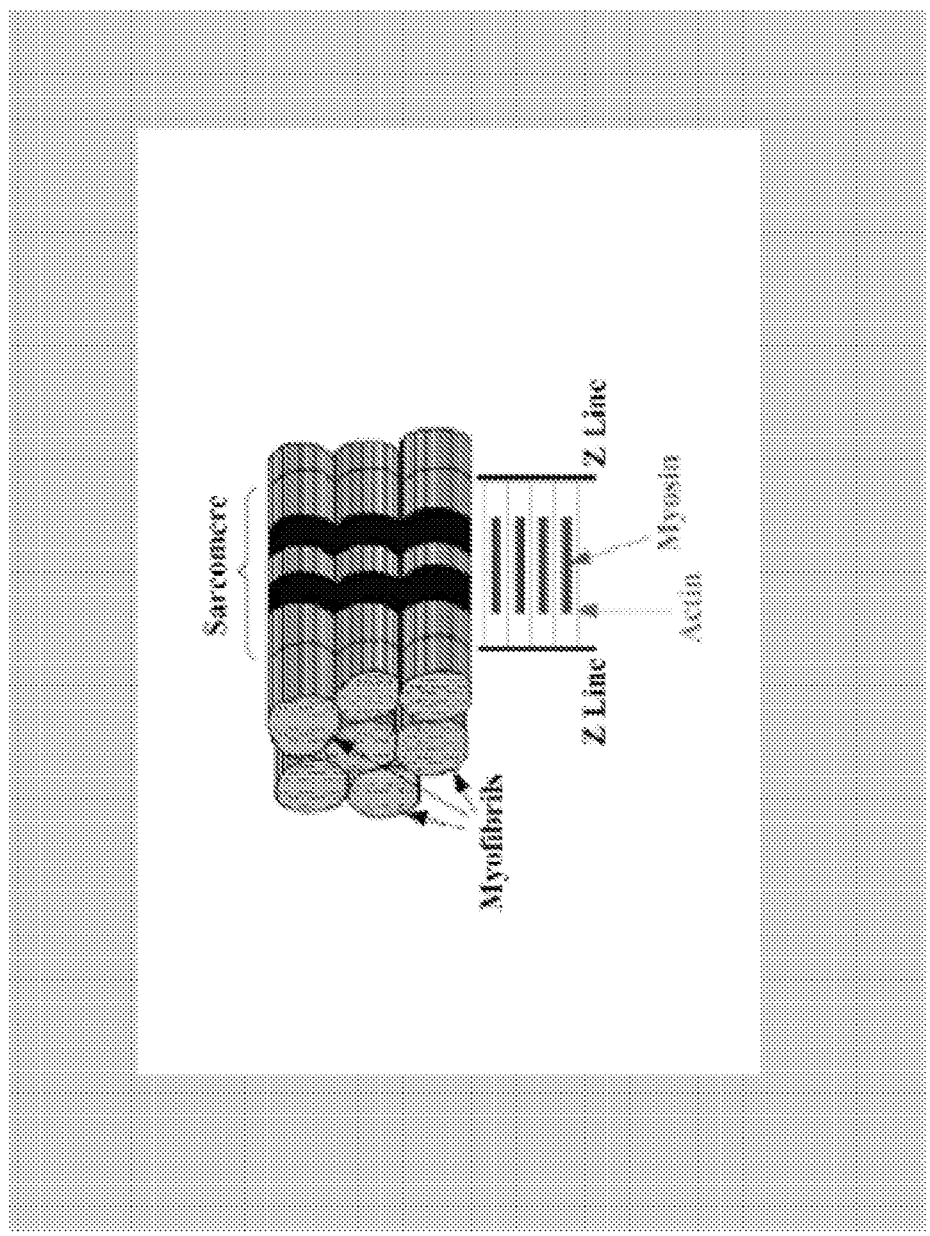
FIG. 10 shows the cardiac myocyte interior cross section.

Electrical excitation causes contraction of a myocyte through the action of calcium ions moving into the cell. When a supra-threshold stimulus reaches a working myocyte, sodium and calcium diffuses into the cell. The electrical stimulus continues along an outer conductive channel (sarcolemma). The interior of these muscle cells contains bundles of myofibrils (see FIG. 10). The muscle fibers are composed of sarcomeres, which are functional contracting units made up interdigitated myosin and actin molecules called myofiliments. The influx of positive ions carries the voltage potential into the cell wall through tubules. When the excitation reaches the sarcoplasmic reticuli, additional stores of $Ca^{++}$ they contain are released onto the sarcomere.

Temporary protein attachments are generated between myosin (axial proteins) and actin (inserted in cell ends). This structure pulls toward the middle of the cell, resulting in a telescopic shortening of its length (Simmons, 1992, p. 211) and achieving the electromechanical coupling. The fibers relax when the cell repolarizes by pumping calcium ions back out of the cell. Under normal conditions, there is a corresponding mechanical event for each electrical depolarization (Cummins, Field, Hazinski, & Babbs, 2004, p. 104).

In this chapter, primarily normal cardiac physiology has been described. However, pacemakers and implantable defibrillators are applied to persons at risk of or having demonstrated insufficient cardiac output. Congenital defects, acquired heart disease, ionic imbalances, or pharmaceutical effects all may lead to aberrations in the regular pattern of electrical conduction (arrhythmias), resulting in decreased performance of the heart as a pump. The heart itself, like all other body tissues, requires its own fresh 'coronary' blood supply. Inadequate pumping causes decreased flow of oxygenated blood to the heart muscle itself. Coronary artery blood flow that is insufficient or blocked results in the reduction of available oxygen due to its continued utilization and the accumulation of acidic byproducts of metabolism. These conditions will cause excitatory instability of the tissue, changing the electrical rhythm. The human body is an incredibly adaptive system, and if these degenerative changes occur gradually enough, the heart tissue will compensate, up to a point. Otherwise, abrupt onset of arrhythmias will result. Slow heart rate arrhythmias (bradycardias) or fast heart rate arrhythmias (tachycardias) can range from no symptoms, debilitation, pain, unconsciousness, or death (Beers & Fletcher, 2003, p. 173).

Sensing of the Excitation Signal by the Implant

Figure 11:
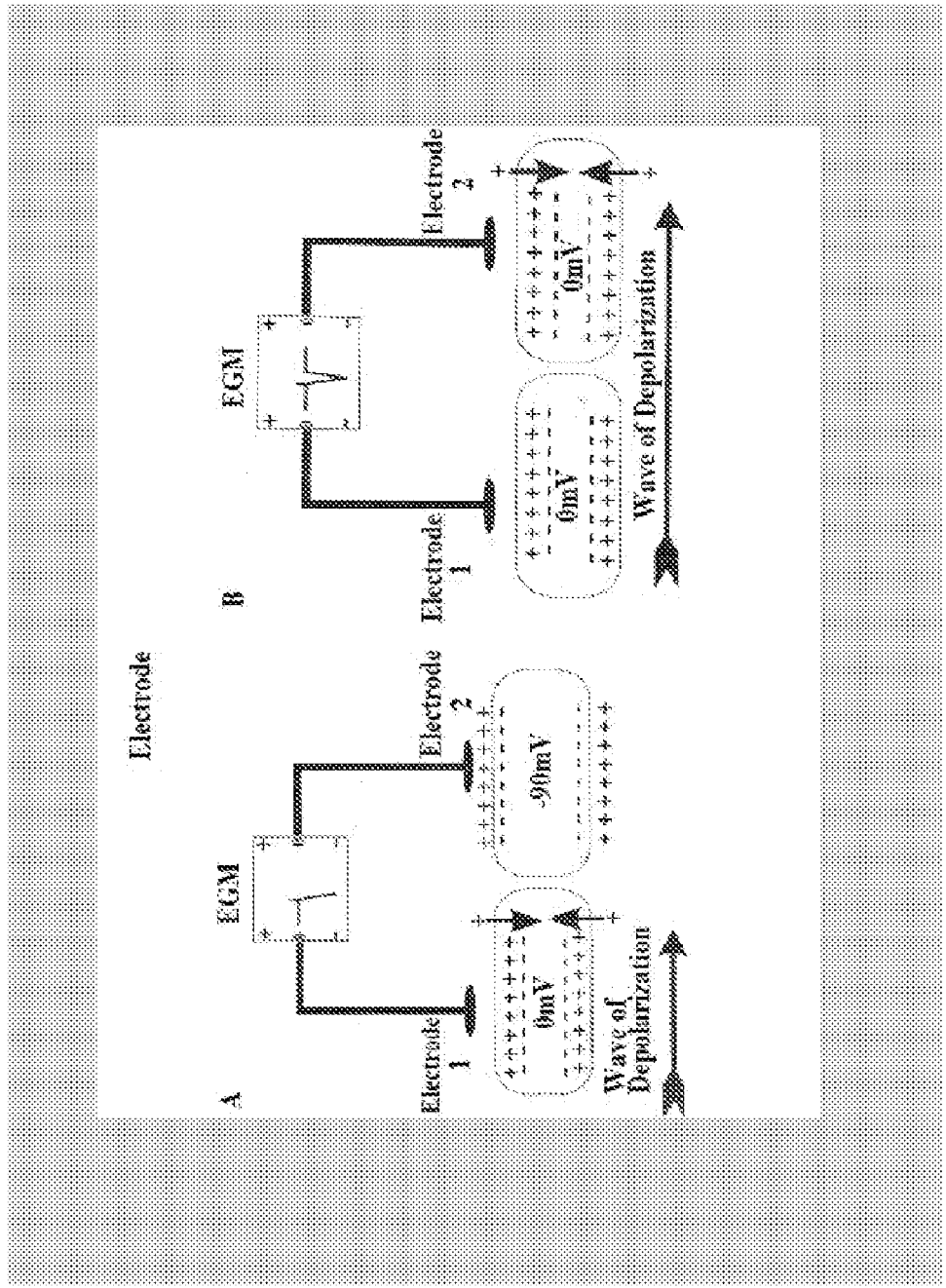
FIG. 11 shows an example of IEGM deflection.

The implantable pacemaker or defibrillator senses excitation signals of the heart subject to the path of the signal through the tissue, the tissue-lead interface, and the input stage filtering of the implant. Timing windows also exclude interfering signals. The net potential difference between the two contact elements of the leads results in a corresponding signal representation in the implant. FIG. 11 shows how the wave of depolarization results in a potential difference across the contact elements. In subfigure A on the left, the transmembrane potential at electrode 1 becomes neutral with the influx of $Na^{++}$, but becomes negative relative to electrode 2.

In the implant, the function that generates the corresponding representation, such as an ADC, produces a ramping output. As the excitation wave passes through the tissue adjacent to electrode 2 (subfigure B on the right), the potential difference between the leads dissipates. The ADC output correspondingly ramps toward zero.

The action potential propagates from one myocyte to the next until it has spread through the entire working tissue of the heart. In the wake of this electrical wavefront sweeping through the heart, a mechanical contraction occurs. The electric wavefront is preceded by positive charges and followed by negative charges.

Figure 12:
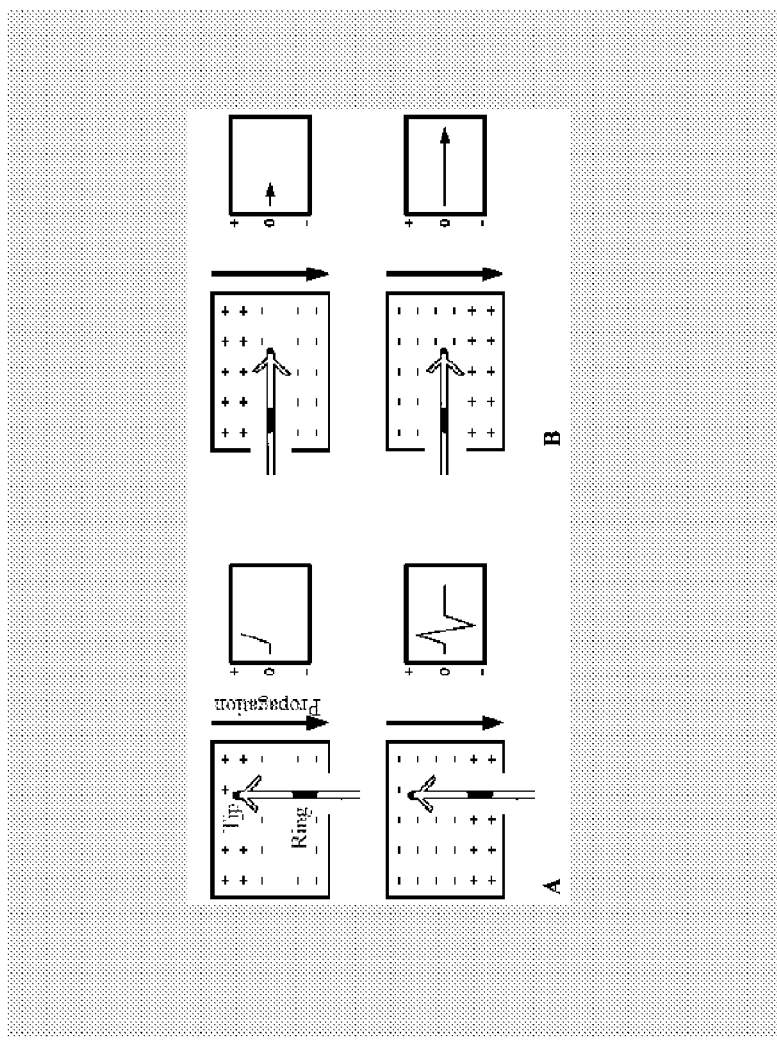
FIG. 12 shows the orientation axis through the electrodes relative to the direction of the excitation wavefront affects the amplitude of the IEGM.

FIG. 12 shows the effect of the orientation of the axis through the electrodes on the resulting polarity and amplitude of the IEGM. The lead is connected to differential amplifier inputs and subsequently discretized in amplitude and time. The orientation of the axis through the electrical contact elements relative to the excitation wavefront scales the amplitude of the resulting signal in the implant.

The electrodes are shown in FIG. 12 are bipolar with 'tip' and 'ring' electrodes determining the scope of observation (box with negative and positive charges). The arrow along side the box indicates the direction of propagation of the excitation wavefront. In sub-figure A, positive charges approach the tip electrode (connected to the non-inverting amplifier input) resulting in a positive upstroke in the ADC output. After the wavefront of net positive charge movement passes the tip and approaches the ring electrode (inverting amplifier input), the ADC output ramps negative. Sub-figure B shows that orientation of the electrode axis perpendicular to the excitation wavefront yields an ADC output of zero. Charge movement at 45° will yield $$\frac{1}{\sqrt{2}}$$

of the corresponding magnitude.

Figure 13:
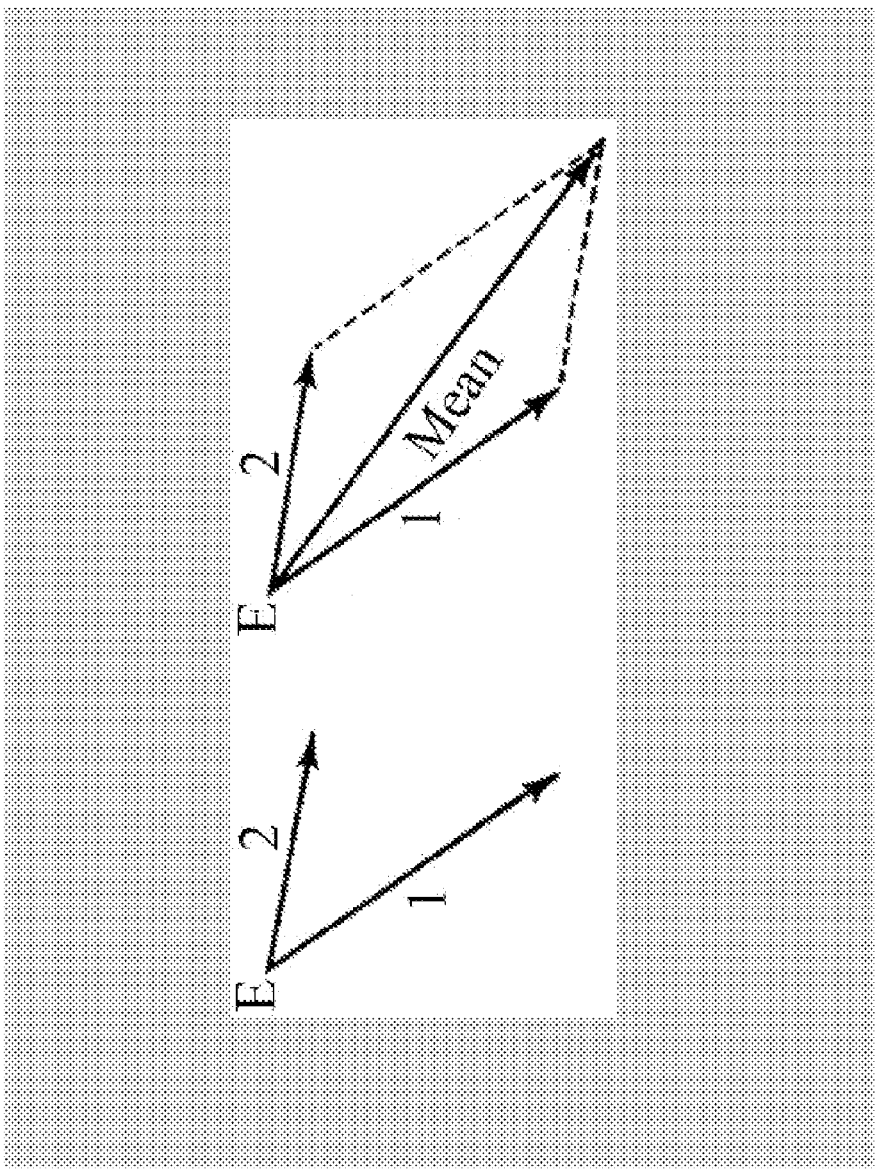
FIG. 13 shows the resultant vector from two components.

The mean vector indicates the average direction of the electrical wavefront and its magnitude as it travels through the myocardium (see FIG. 13). A vector whose length is a measure of voltage at a point in time represents the depolarization voltage. At any instant, a mean vector may be derived from the superposition of the instantaneous vectors of the action potentials of millions of individual cells. The resulting mean instantaneous vector can be decomposed into orthogonal components, where only the parallel component contributes to the signal seen by the implant.

Most of the muscle mass is in the ventricles, and therefore the primary electrical activity occurs during the contraction of the ventricles, which is associated with the ventricular depolarization event (corresponding to the QRS in the IEGM). Because of this, ventricular sensing electrode is typically placed at the apex of the right ventricle (near the head of the mean QRS vector of FIG. 14).

Figure 14:
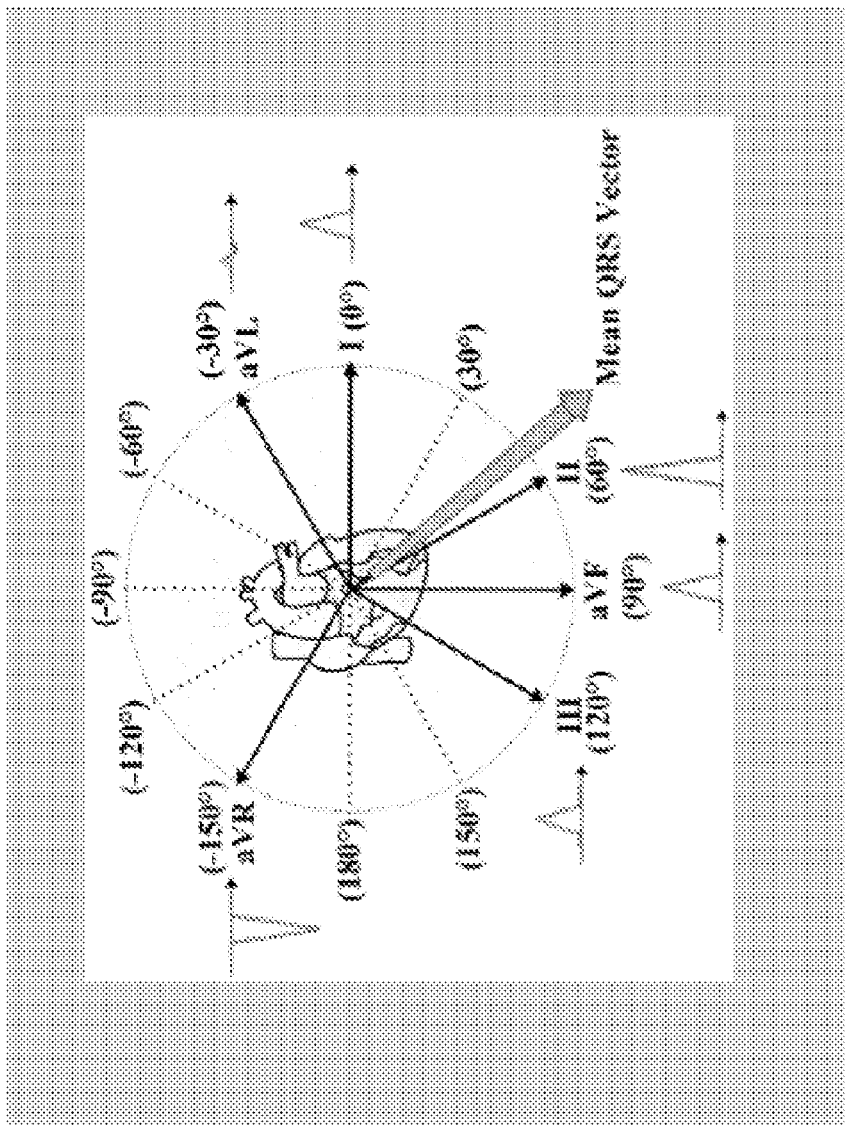
FIG. 14 shows the frontal leads.

FIG. 14 shows the time-averaged vector over entire time of ventricular contraction, viewed from surface frontal leads at various rotations around the frontal plane. The arrows represent reference lines passing the axes of electrical contact elements ('leads') where the positive amplifier input is the arrowhead and the negative amplifier input is the tail. If the axis of a lead lies on the 'II' reference line, the majority of the ventricular depolarization is parallel and toward the positive lead. The resulting amplitude will be a primarily positive output from the quantizer.

Use of the Intra-Cardiac Electrogram

This disclosure addresses the signal taken from electrical contact with the inner surface of a chamber or vessel of the heart, and will be referred to as the intra-cardiac electrogram (IEGM). The electro-mechanical interdependencies and redesign costs of electrodes and input stages make available devices channel-limited. This work will use IEGM signals from present technology without requiring a new sensor.

The IEGM is the signal as seen by an implanted pulse generator (IPG) or implantable cardioverter defibrillator (ICD). The IEGM is the signal input of a contact element touching the heart versus sampled time. The frequency of depolarizations in IEGM yields the heart rate value, and is used by the physician to adjust the IPG in follow-up examinations.

IPGs treat disturbances of the heart. The IPG or ICD uses the IEGM to determine which rhythm disturbance is present, and delivers the corresponding therapy. In a sense, the physician's diagnostic and interventional abilities have been extended by this technology into a remote observation point 3 mm in diameter inside the patient's heart.

Figure 15:
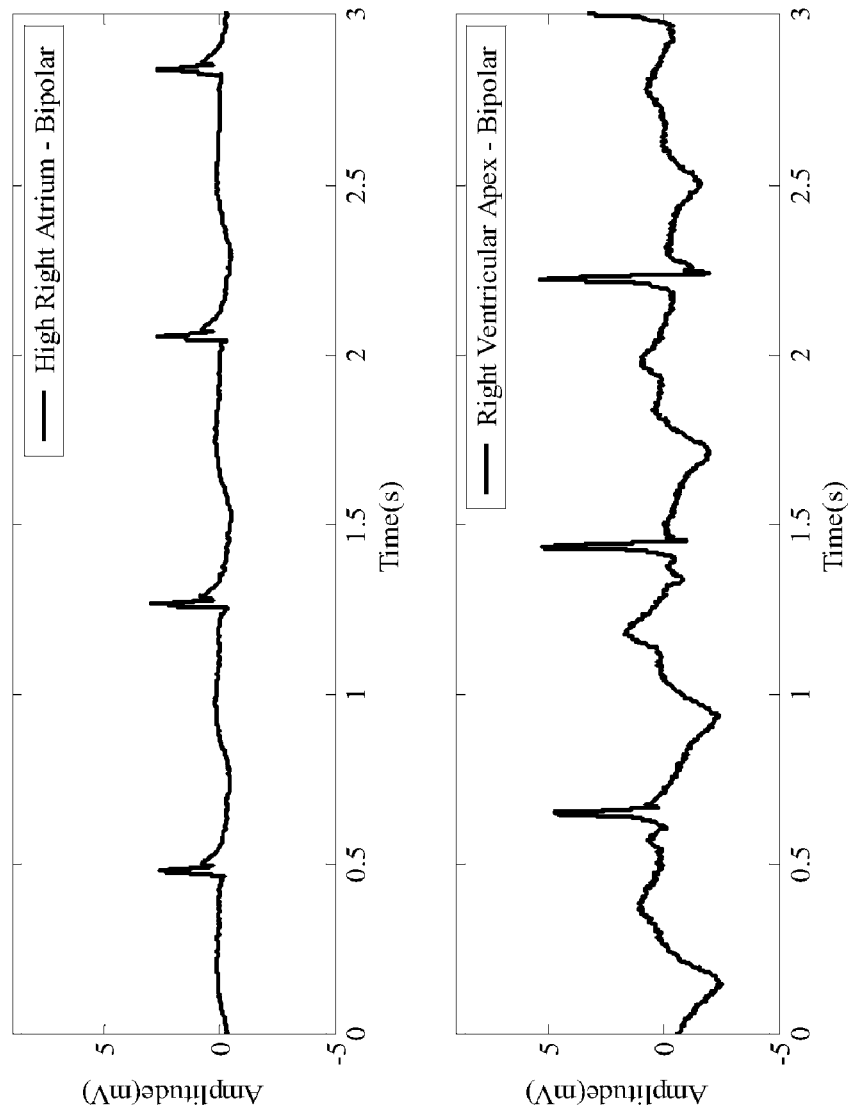
FIG. 15 shows an intra cardiac electrogram of normal sinus rhythm.

Most readers who have seen a display of human heart electrical activity on television or in an actual health care setting, have seen a signal derived from electrical contact with the surface of the skin called an electrocardiogram (ECG, or EKG in Europe). FIG. 15 shows the intra-cardiac electrogram of an intrinsic normal rhythm. This particular recording was performed at a sampling rate of 512 Hz with 16 bits of amplitude quantization. This high-resolution recording serves as a starting point for simulation; the resolution is further degraded by the feasible level in the implementation ADC, for example, 1 Obits.

Figure 16:
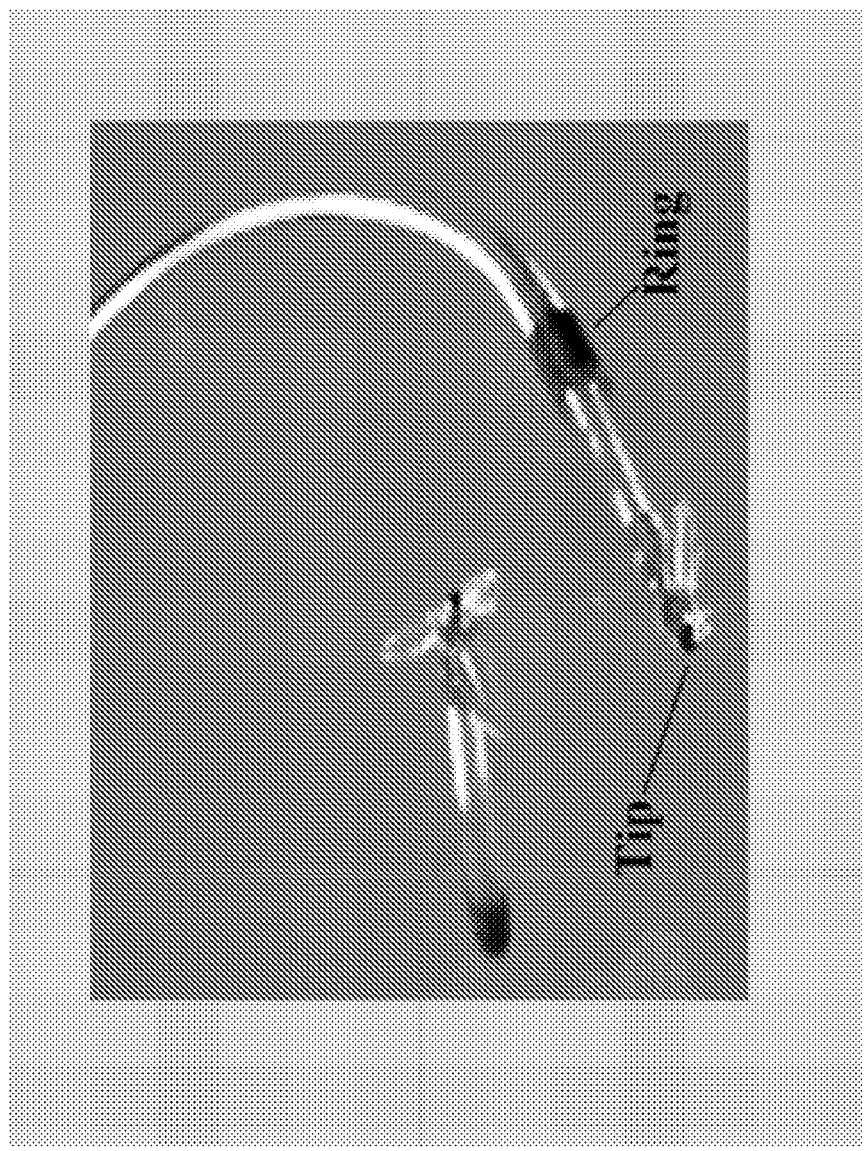
FIG. 16 shows bipolar lead contact elements.

There are two principal configurations of electrical sensing through the positive and negative contacts of the intra-cardiac lead, 'unipolar' and 'bipolar.' In the unipolar method, the signal amplifier has the amplifier signal ground connected to the metallic casing of the implanted device, making the body mass near the case the 'indifferent input.' The amplifier input is connected to a lead with a single electrode at the distal end which is embedded in tissue on the inside surface of a heart chamber. The physical distance between the 'case' (indifferent electrode) and the 'tip' (differential electrode) is about 8" to 10" and creates an electrical axis that spans the breadth of the heart. This results in a signal that receives inputs from an entire heart chamber, with some attenuated super-position of signals from other chambers. In the bipolar lead, the lead has two distal electrical contact elements a 'ring' and a 'tip' that are typically separated by 10 mm to 20 mm (FIGS. 2 and 16). For the bipolar lead, the ring is the indifferent sensing electrode. Table 2 resolves the various terms used for connection points between the tissue and the device for the two functions of pacing and sensing.

(Note: The negative lead of the pulse generator is connected to the tip for tissue stimulus. The non-inverting input of the sense amplifier is connected to the tip. See FIG. 16)

In the bipolar lead such as leads 14 and 16 of FIG. 2, there is less visibility of the aggregate behavior of the heart, due to the lead contacts being so close to each other. The signal sensed by the bipolar lead is a volumetric derivative of the whole heart electrical activity. The voltage potential induced on the bipolar lead by the electric field is smaller in amplitude because the dipole sensitivity attenuates by $1/r^2$ in the near field (where r is the distance between contact elements) and less of the whole heart energy is presented to the input amplifiers. On the other hand, the distance from the lead tip to the case ground in the unipolar lead makes the resulting IEGM amplitude larger because the whole heart mass contributes. The event is seen by the bipolar lead briefly in time only when the electrical wavefront passes nearby. The event at the unipolar lead is longer in time due to propagation through the larger tissue mass.

Figure 17:
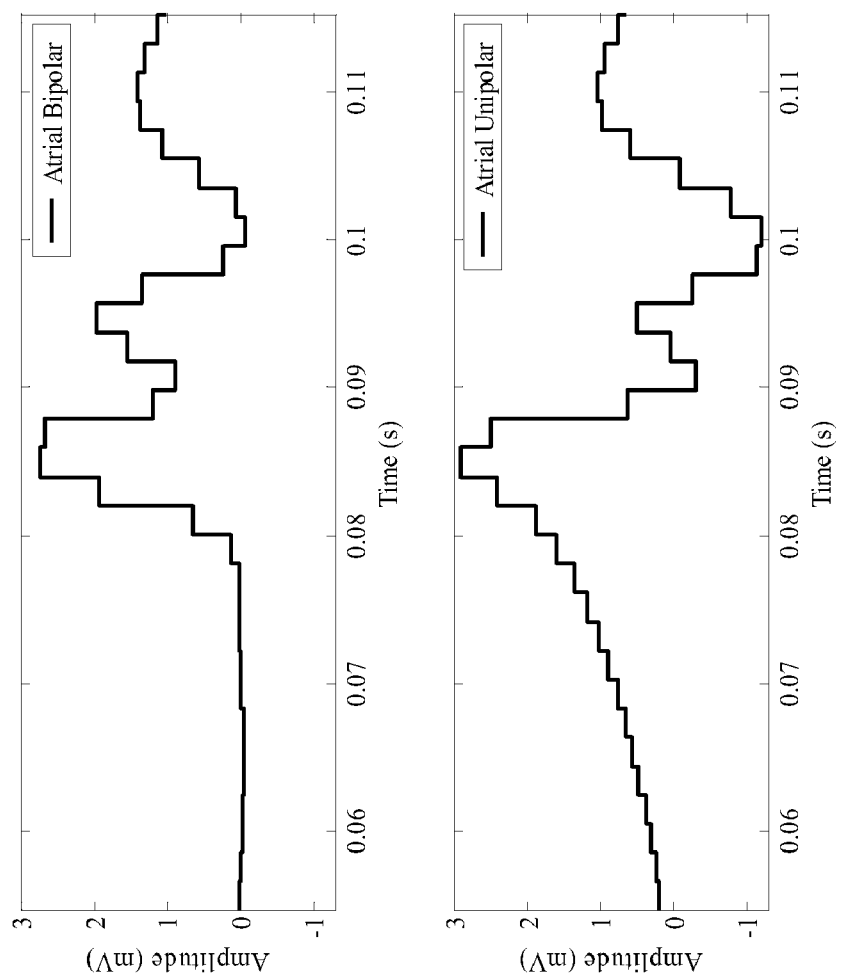
FIG. 17 shows a comparison of simultaneous recordings shows the bipolar event has a well defined onset, and the unipolar event does not.

The wavelet transform can be applied to the unipolar signal, but the bipolar may be more suitable due to the compact support property of the wavelet (Mallat, 1999, p. 6). Consider a recording of the same event simultaneously using bipolar and unipolar leads (see FIG. 17). Preceding the onset of the bipolar event at 0.08 s, there is essentially a zero level on the signal satisfying the left hand boundary assumption used in this work: $x_{t<0}=0$, that is to say, before the event begins, the signal level is 'isoelectric.' In contrast, the start of the unipolar event is difficult to define, as nearly half the samples constitute a ramp. Filtering to sharpen the unipolar onset also distorts the features of the event. For the right hand boundary, there is no advantage to the bipolar signal. In that case, the window is ended after a sufficient number of samples ($2^{integer}$) to capture the event information. In this latter case, a simplified linear boundary assumption was used to handle the right hand edge (§The Predict Function).

Present Pacemaker Input Stage Architecture

Figure 18:
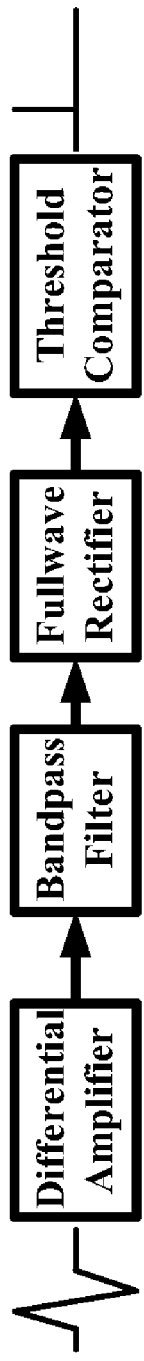
FIG. 18 shows the IEGM is converted to threshold crossing event by the input stage of an implantable device.

FIG. 18 shows a functional block diagram of a sensing unit such as sensing units 62 and 66 of FIG. 2 for present day implantable devices (pacemakers and defibrillators). From left to right, the IEGM is conducted through two electrodes to the input of a differential amplifier to provide a signal capable of crossing the comparator threshold and compensating for filter attenuation. The combined attenuation and amplification reduces the error free dynamic range of signal path. The signal is then band pass filtered both to prevent aliasing with discrete time sampling, and to reduce interference from unwanted events. The signal is full-wave-rectified to allow either positive or negative slopes to trip the comparator threshold. The output is an indicator that a threshold was crossed, and is the only representation used for therapeutic decision making in the device timing circuits. The ADC step is not shown separately as it is usually integrated with the amplification and/or filtering block, for example, in a switched-capacitor filter. The output of any digital filtering performed after ADC should decay to zero in a finite number of samples when an impulse input function, such as a depolarization event, is followed by zero input. Thus, the digital portion of the filter should be free from overflow limit cycles (oscillation at the extrema of dynamic range) and is accomplished by correct magnitude scaling of the input. Additionally, error integration in the LP portion of the band pass can promote granular limit cycles (oscillations due to temporal correlation of quantization effects on least significant bits).

To prevent this, the band pass can be structured as a cascade of first order filter blocks: HP→LP→HP, where the last HP is required to cause the BP filter output to decay to zero (Diniz, Da Silva, & Netto, 2002, p. 334). The passive portion of the band pass filtering is very simple, and attenuates out of band interference before it impinges on the digital filter. Typical sampling frequency is relatively low (512 Hz) allowing the circuits to be designed with lower bandwidths resulting in power consumption savings.

Pre-processing of the IEGM

The event, to be sensed by the device, has induced a voltage across the input terminals of an amplifier through the impedance of a tissue lead interface, and an anti-aliasing filter. At some point, the signal is converted from continuous-valued continuous-time to discrete valued (ADC resolution ranges from 8 bits to 16 bits) and discrete-time sampled at a rate of 512 Hz, thus creating a digital signal representing the physiological signal (IEGM).

Figure 19:
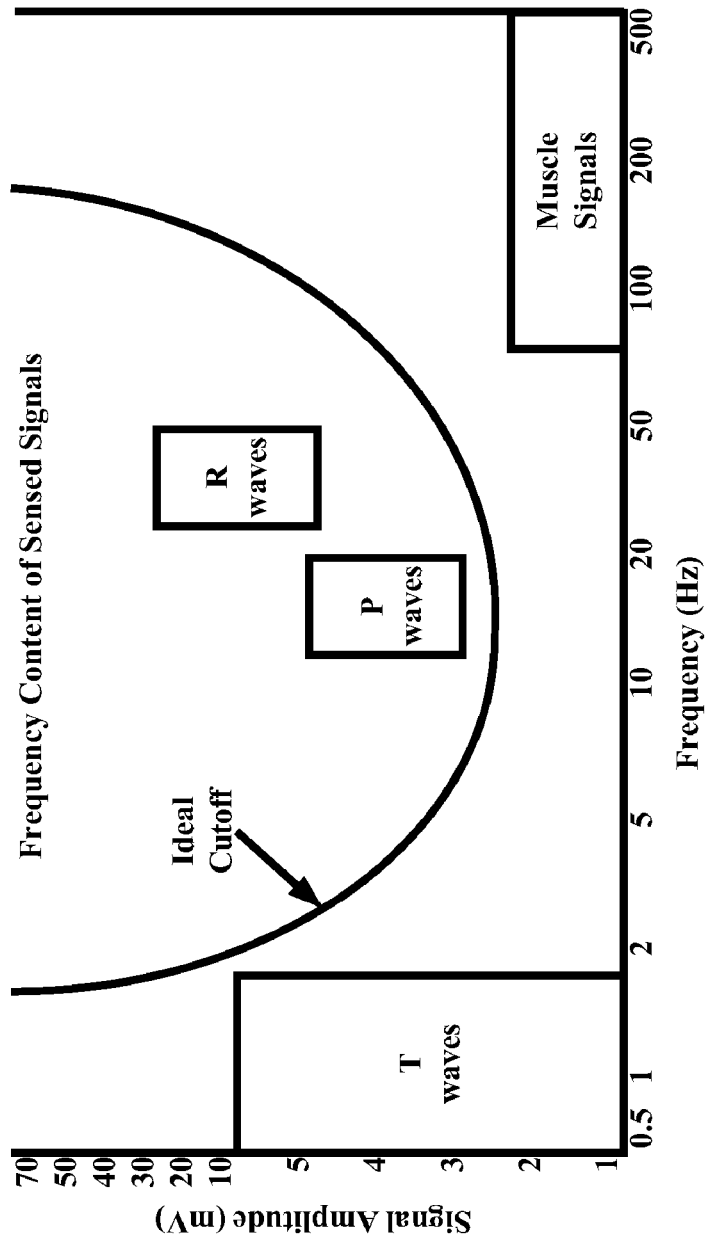
FIG. 19 shows the frequency content of IEGM features for threshold based event detection is concentrated in specific regions of the pass band.

The purpose of fixed filtering beyond anti-aliasing of the input data is to remove DC and very low frequency components from motion, metabolism, autonomic tone, and respiration ("Heart Rate Variability," 1996, p. 1047, table 2), so that the input amplifier and analog-to-digital converter (ADC) are not held in saturation at one of their internal nodes. Possible causes are fixed or induced polarization of the lead tissue interface, or induced by residual charge following a pace pulse applied on the same lead. Motion artifact also induces low frequency content in the signal. In practice, the lower stopband for the threshold-based event detector may be up to 5 Hz to achieve sufficient attenuation in the stop band. As shown in FIG. 19, the primary energy, and therefore the morphological information, of P-waves and R-waves remains inside the pass band. For threshold detection, as opposed to morphological discrimination, the pass band should begin above 5 Hz, since the otherwise legitimate events would not be detected, and the upper end preferably attenuates at 100 Hz. Although, other morphological feature information extends up to ~175 Hz, unwanted muscle signals arise and attenuation in the transition band of a typically used low processing cost first order Butterworth anti-aliasing filter with pass band edge at 100 Hz is only 63% at 175 Hz.

Additionally, if the sampling rate was reduced to 256 Hz, aliasing of any remaining unattenuated signal content at 175 Hz would produce a false image in the pass band used for threshold based event detection. Therefore a sampling rate of 512 Hz is not only convenient (division by two from a 32 kHz crystal), but necessary.

Narrowband Filtering

Figure 20:
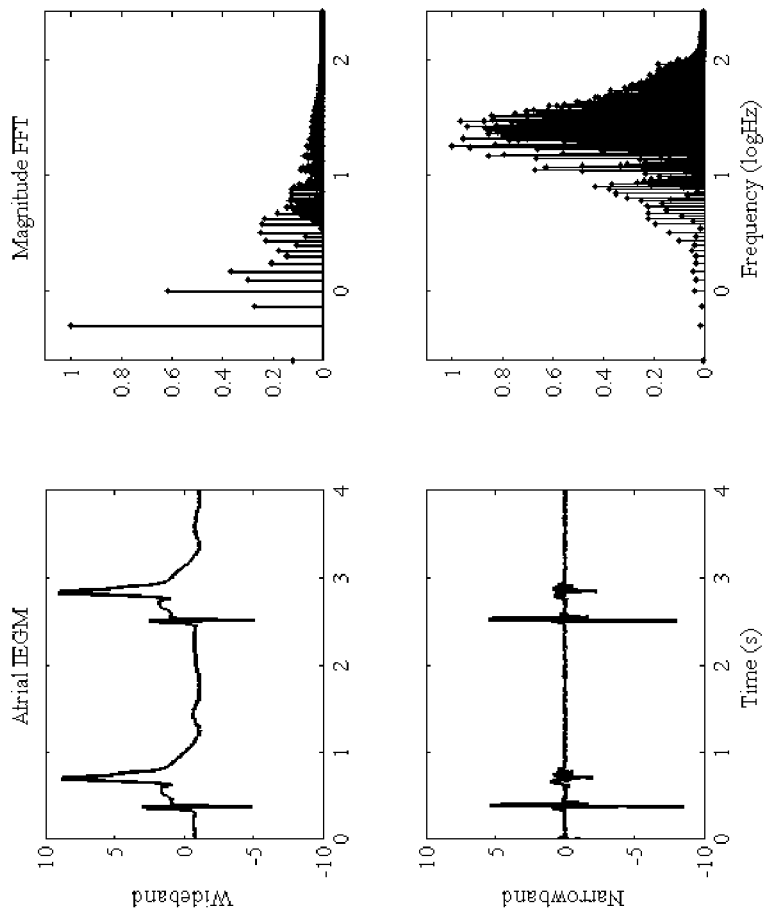
FIG. 20 shows the original IEGM (wideband) is filtered (narrowband) to reduce aliasing and false detection of events at the threshold based sense detector comparator.

While the low pass component of the input filters removes high frequency interference, such as chest muscle activity, it also performs an integration function promoting limit cycles in the digital filter. As there is no basis to assume that the unfiltered signal is asymptotically zero mean, the digital filter could drift to one of the limits and remain there making the system blind to events. In fact, these offsets arise naturally even in zero mean systems due to sampling of a long term process, that is, arbitrary samples of the population are biased. Therefore, the input filter (FIG. 18) also attenuates signal energy at DC and up to ~20 Hz, the latter signal content being produced by respiration and the autonomic nervous system. The narrow band filter certainly encroaches on the morphological information of the P-waves and R-waves, where the intent is to reduce these events to comparator threshold crossings. For example, FIG. 20 shows the 'wideband' (directly from the electrodes) and 'narrowband' (signal fed to threshold comparator) IEGMs (left hand subplots) with their corresponding FFTs (right hand subplots). The example is an atrial IEGM with a large ventricular crosstalk signal following the atrial depolarization event called 'far-field.' The filtering attenuates the far-field signal in an attempt to reduce the occurrence of false detection of this spurious event. The narrowband filter can be seen from the FFT to attenuate signals outside the pass band of ~20 Hz to ~100 Hz. This pass band is optimized for threshold detection, not for the preservation of morphological information.

Event Detection (of the First Kind, that is, Detection of R-waves and p-waves)

IPGs originally paced like metronomes, asynchronously, regardless of any intrinsic rhythm (Hayes, Lloyd, & Friedman, 2000, p. 8). Improvements were made to postpone a scheduled device stimulation (inhibition) after the heart had just successfully depolarized on its own, and for a time after a stimulus (a device refractory period that models the tissue refractory period) to prevent stimulus during the vulnerable part of repolarization. This improvement had two benefits. First, when the heart depolarizes itself successfully in a normal pattern, this is always preferable physiologically. Second, during phase three of repolarization (FIG. 8), the heart tissue is vulnerable, in that a stimulus could trigger the onset of an arrhythmia. Third, since the IPG is a battery-powered device, if it does not send a stimulus when it is not needed, its lifetime before replacement is extended.

Figure 21:
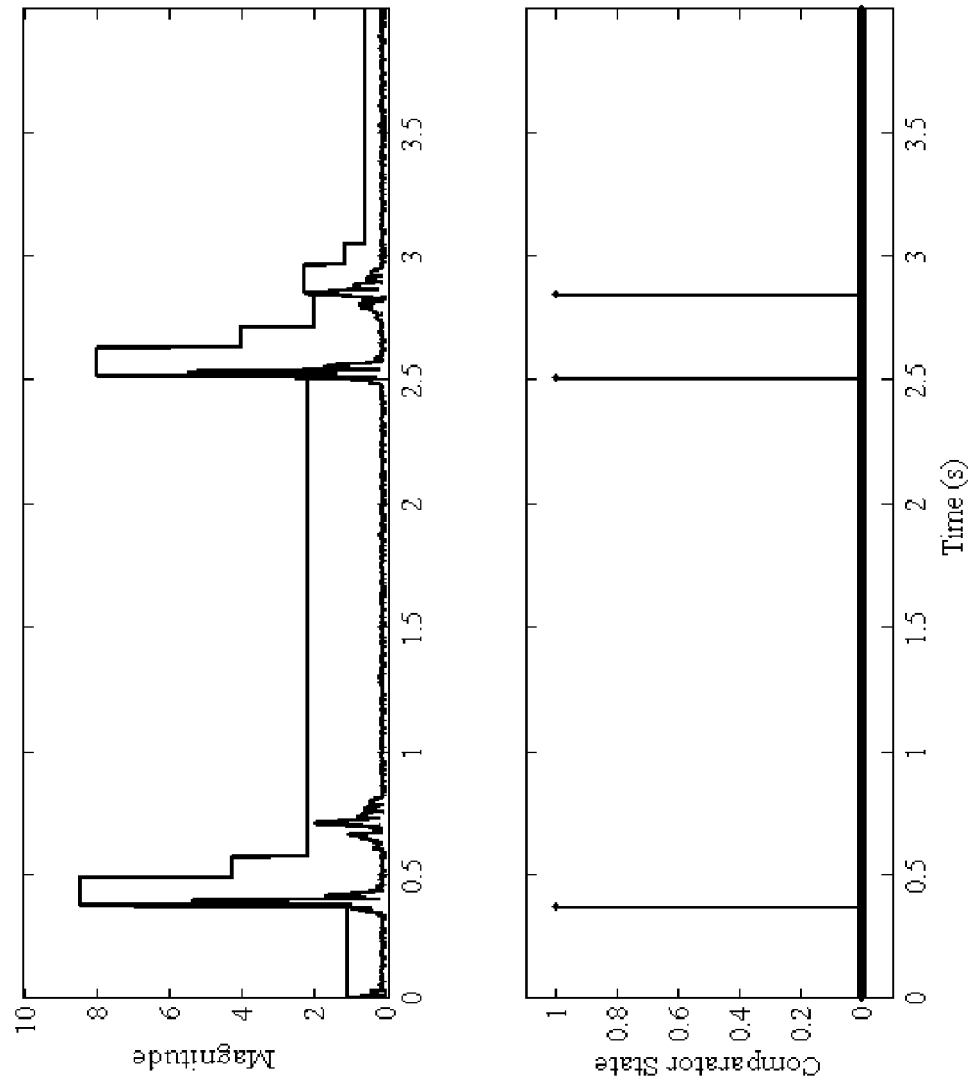
FIG. 21 shows the conversion of IEGM to event markers.

Events must first be detected in time before their classifications can be used to make electro-therapy decisions. The present technology locates the occurrence of an event in time, by the crossing of an absolute voltage threshold, such as, a comparator limit. Alternatively, once the signal has been digitized into a sign-magnitude, interval based systems mark the event when its magnitude component exceeds a limit. There is no relation of this marker to some 'fiducial point' within the event other than that the threshold has been crossed. FIG. 21 shows this information reduction step in action. The narrow-band IEGM from FIG. 20 is passed to the threshold comparator. The upper trace shows the full-wave rectified waveform compared to an adaptive threshold. The threshold has an adaptation period and a detection hold-off period. The adaptation period causes the first far-field event to be ignored, but the second far-field is detected resulting in the appearance of a transient high rate. This high rate could bring the device out of standby and trigger arrhythmia therapy. The hold-off period prevents more than one detection before the first threshold reduction. By the time the signal has been rectified, it is evident there is very little left of the original morphology that would allow distinguishing the two kinds of events, other than magnitude.

Whether the threshold is fixed or adapted from previous events, there is no relationship of the threshold-crossing indicator to any 'fiducial point' occurring within the electrophysiologic event.

IEGMs contain many kinds of events that do not correspond to the primary event of interest, that is, a true depolarization. Despite the threshold method shown in FIG. 21, the figure shows the third detected event is spurious.

Figure 22:
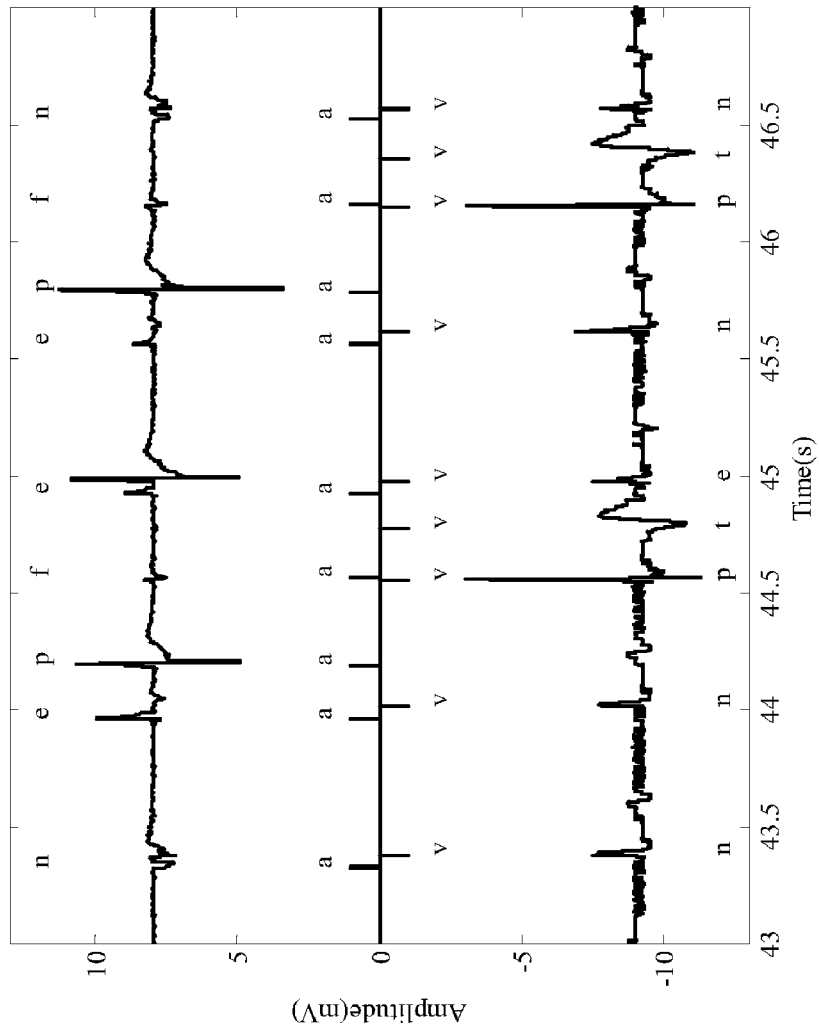
FIG. 22 shows that despite adaptive thresholds and complex timing windows, pseudo events are indistinguishable from real events when morphology is excluded.

FIG. 22 is divided into three main sections demonstrating pseudo-events.

First, the trace in the upper half of the figure is the atrial IEGM (just above it are letters indicating the true identification of the events). Second, the event marker trace along the zero line indicates device-based sensing threshold crossings in each chamber (up or 'a' for atrial, down or 'v' for ventricle). Third, the trace in the lower half of the figure is the ventricular IEGM (just below it are letters indicating the true identification of the events). The true event types are identified by the letters: normal 'n,' extra-systole 'e,' evoked response 'p,' far-field 'f,' and T-wave 't.' In the device the threshold must be sensitive enough to detect a normal event 'n,' such as the one in the ventricle at 43.4 s. Nevertheless, the device then also detects the T-waves in the ventricle channel occurring at 44.7 s and 46.4 s, producing false event detections. The two ventricular paces crosstalk into the atrial channel resulting in false detection of far-field events as senses 'f' at 44.6 s and 46.2 s.

Limitations of Present Day Event Detection Methods

Once past the amplifier and ADC, the detection of intra-cardiac depolarizations in present technology is binary valued, that is, the resulting amplitude inside the device has crossed a comparator threshold or not. When morphology is visible to the physician, different electro-mechanical events have different therapeutic decision choices. When morphology is invisible at the comparator output, only the markers can be used to make therapy decisions by the device.

Alternatively, some event detection methods use the first derivative, which is a shape metric. In this method, the arithmetic differences between adjacent time samples are used. When some number of these differences exceeds a $$\frac{dv}{dt}$$

threshold, an event is considered to have occurred and a marker is issued. Such a system is still equivalent to comparator crossing after high pass filtering. Due to the non-stationary nature of the electrocardiogram, a richly varied morphology results. The consequence is that fixed threshold algorithms do not adapt to changes in the physiologic signal, and over- or under-sensing results in false positive or false negative results.

The depolarization events ordinarily result in a corresponding mechanical contraction of the heart. If markers are frequent, they indicate a higher heart rate, more frequent mechanical events, and higher resulting cardiac output (Hayes, Lloyd, & Friedman, 2000, p. 54), up to a physiologic limit of diminishing returns. Although, with incorrect adjustment of threshold and ventricular refractory period, FIG. 22 demonstrated that this chain of reasoning does not always hold. Human experts characterize normal and abnormal rhythms by using both rate and characteristic shapes. For the implanted device, only device memory allows the storage of a limited resolution IEGM for off-line review by the physician in the follow-up setting. Online analysis methods in implanted devices today use only rate and relations between event markers from the atrium and ventricle, though there is intense interest in the possibility of using shape information (Gillberg and Koyrakh, 2002).

Figure 23:
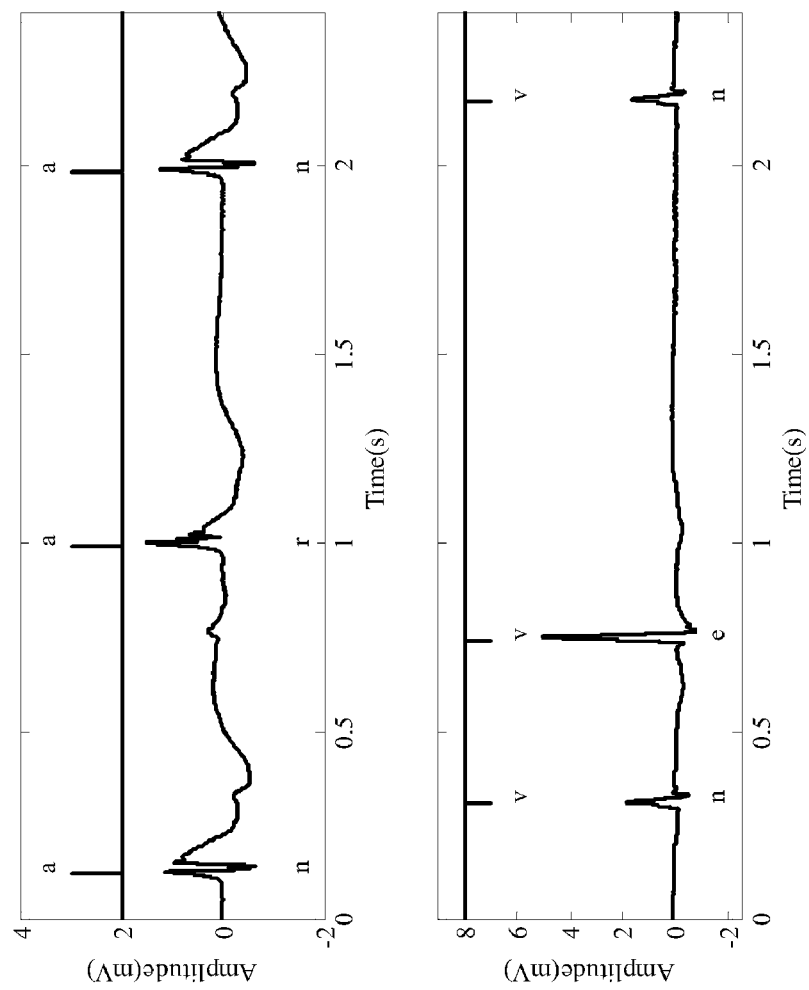
FIG. 23 shows the depolarization of the heart through an aberrant conduction path causes the changed morphology of the ventricular (e), and atrial (r) events.

FIG. 23 has two main parts. The upper subplot has two traces: (1) the upper trace in the top subplot shows event time markers ('a' for atrial), (2) the atrial IEGM (lower trace in the same subplot) shows a normal 'n' event, an abnormal 'r' event, and another normal event. The morphology of the event varies because the conduction path taken through the heart tissue changes the direction the wavefront is traveling as it passes the lead contact elements for the abnormal event. The lower subplot shows the cause of this event. The upper trace again shows the 'v' for ventricular event markers, indistinguishable from each other. The trace in the lower subplot shows the a ventricular normal event 'n,' and ventricular extra-systole 'e,' followed by a ventricular normal event 'n.' Note that 'e' and 'r' are aberrant versions of 'v' and 'a,' respectively.

In summary, a normal rhythm interrupted by a ventricular premature depolarization and the event occurring in the atrial chamber is conducted abnormally. The change in shape for events in both chambers is apparent in this example. The discrimination between these two events has value in therapeutic decision-making.

Accurate Identification of a Fiducial Point

Figure 24:
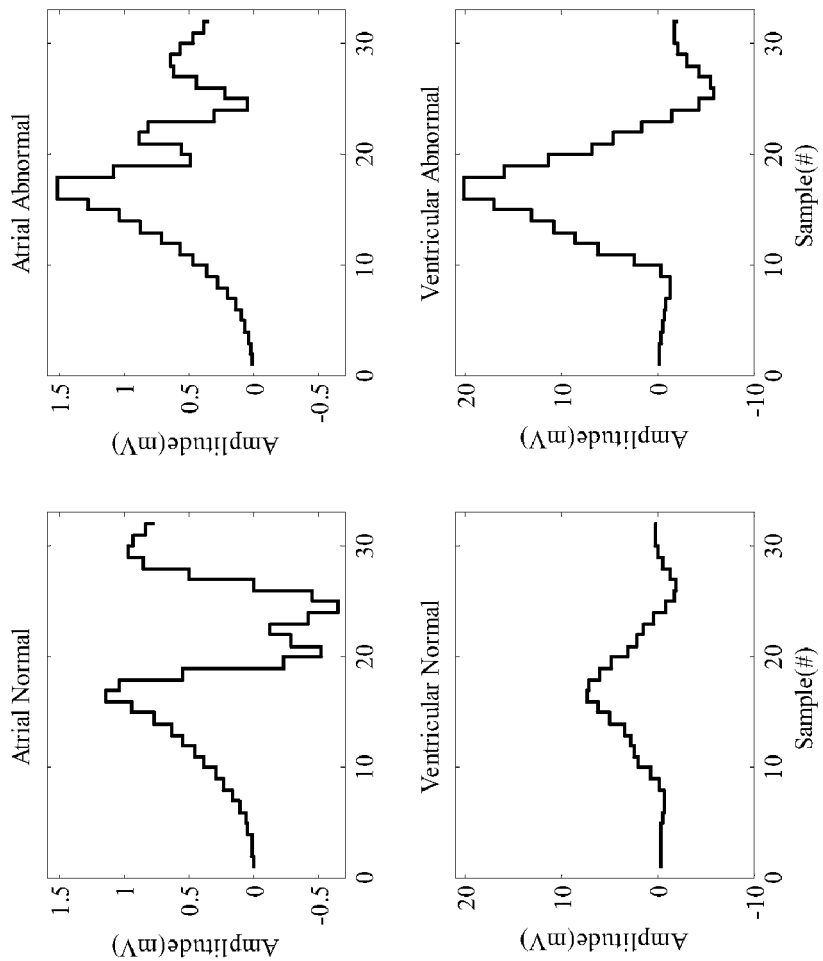
FIG. 24 shows the centering event time samples on the of peak amplitude reveals the morphological differences of normal and abnormal events.

High quality event detection is necessary to accomplish the objective of this work. In the case of morphological classification, features at certain time offsets within the event must be compared to like features at a similar time offset in other events. When time sampled and quantized into discrete amplitude values, the IEGM time series has features that occur with some reliability at certain time offsets within events of interest. Therefore, for morphological classification, it is critical to buffer the time samples of events offset with respect to particular feature (peak) that correlates well from event to event, as shown in FIG. 24. Note the centralized points in the events (sample #15) are the P-wave peak for the atrial event, and the R-wave peak for the ventricular event. It is desired that, the chosen fiducial points for centering the event are computable and repeatable between events. The unequal size steps at different sample numbers in the recording (small step changes near sample #1, larger step changes near sample #16) do not correspond to a non-linearity in the ADC, but to the actual increase in the $2^{nd}$ derivative of the amplitude as the wavefront passes the contact elements. (Note also: The sampling rate in this recording is 512 Hz, but the quantization level is now 14 bits, since bits 15 and 16 have been reserved for calculation overflow in the device that made this particular recording, this to explain any apparent change in quantization level from earlier figures.)

The Basis of Morphological Differences (Event Detection of the Second Kind)

The four events, pictured in FIG. 24, also show normal (antegrade conduction) events on the left and abnormal (retrograde) events on the right. If waveforms differ in this way, this indicates that the wavefront originated from some other focus (event origination point in the tissue) or traveled through the tissue along a different path rather than the usual electrical conduction pathway. The shape differences between the usual and changed wave are known as differences in morphology. The usual method for a health care professional, such as a physician, to make a diagnosis of Normal Heart Rhythm is to examine the shape and frequency of the depolarization event on the strip chart recording.

The input stage of existing devices will discard the shape information of both kinds of events (FIG. 24) and leave only timing markers. It is incumbent upon the physician to program the device so that it bins events into the correct classes. For example, if the event rate (1/event interval) exceeds a physician programmed tachyarrhythmia rate criterion, an implantable defibrillator (ICD) will respond with electrotherapy.

The task to identify whether a heartbeat has occurred is the first rudimentary classification in this kind of system. From this point, devices have continued to improve classification with algorithms that provide more detailed categorizations of events and rhythms. The first important categorization, for instance, is atrial tachycardia versus ventricular tachycardia based on heart rate. Other secondarily important categorizations are sudden onset, and the ratio of event counts between chambers. Classifying individual events leads to correctly identifying the predominant rhythm, and results in the application of appropriate electrical therapy.

While the two depolarization events in the IEGM have noticeable common aspects of smooth linear features, there are also details that differentiate the two. The 'smooth' and 'detail' features within an event can correspond to a series of piece-wise best-fit lines and their residuals, respectively. This last point gives a hint at the analysis method of the linear wavelet transform elucidated later. Further, the features with more discriminating power may be the smaller details. This last point is in contrast to wavelet methods emphasizing data compression that dominate the literature on wavelet transform of the IEGM (Novák, 2000; Steacy, 1998; Zhou, 2004; Zhu, 1998). The goal of compression is to find a transformation of the original signal that optimizes the representation accuracy versus dimension reduction tradeoff (Gutierrez-Osuna, 2000). In Principal Components Analysis (PCA), an example compression method, the covariance matrix is diagonalized and the resulting eigenvalues are ranked by magnitude discarding the remainder whose sum falls below some chosen squared error acceptance criterion. The result is that compression methods favor larger components over details.

The trained human expert, on the other hand, recognizes these subtleties, and visually shifts among time scales to assess the most significant information. The human retina contains neural ganglia tuned to recognize straight lines, and the optical cortex scans for these features at multiple scales (Kandel, Schwartz, & Jessell, 2000, pp. 530-531). In anticipation of the next advancement in this field, the wavelet transform is used herein in a prototype of an automated method that seeks to approach the morphological analysis performed by the human expert.

Chapter 3

Methodology

In this chapter, the justifications for choosing the wavelet transform (WT) for extracting shape information from the IEGM are presented. The wavelet is well suited for the transformation of the depolarization event, because like a wavelet, such an event is limited in energy and duration. Depolarization events are isolated from other events in the IEGM data stream or spans of no information by excluding values outside the observation window. Wavelet decomposition begins by isolating the smallest regions of the event from each other. With the detail coefficients, small significant features can be viewed as if through a keyhole. With the smoothed values, the event is viewed as if from arm's length. A historical perspective on morphological analysis of the IEGM can be gained from the following sources: Throne, Jenkins, & DiCarlo, 1990; Greenhut et al., 1992; Morris, Jenkins, & DiCarlo, 1997; Gold et al., 1999; Theres et al., 2000; Gronefeld et al., 2001; Rojo-Alvarez et al., 2003; Saba et al., 2005.

The Basis Function

Fourier and wavelet methods both use basis functions to accomplish transformation (also known as 'analysis') of time data to a new domain. The basis function (a shape) is used in a correlation operation (Beerends, 2003, p. 66). The Fourier transform uses the sine wave as a basis function and creates a description of the time signal in terms of the weighted sum of sine waves of different frequencies and phases. Though only ~30 wavelets appear in the literature, there is no theoretical limit to the number of wavelet transform basis functions to analyze (decompose) the time signal into a weighted representation (Pachepsky, Radcliffe, & Selim, 2003, p. 166). Of these, the Line Wavelet Transform was selected for this work for reasons given in §Time Scale Correlation of the Wavelet Transform, §Properties of the Line Wavelet Transform, §Suitability of Gaussian Assumption, and §Selecting the Best Basis.

Time Localization Property of the Wavelet Transform

First, some key points of the Fourier transform will help to introduce the analysis function of the Wavelet Transform. The Fourier Transform (FT), in general, does not retain time-offset information, because it integrates the signal with respect to the basis function over all time (Dybowski and Gant, 2001, p. 176). This use of unending sinusoids is called 'infinite support' and is appropriate for stationary signals. To adapt the FT to real signals, the Short Term Fourier Transform (STFT) performs a discrete FT of a limited window centered on each sample using the assumption that the values become zero outside the window, or that the window repeats. When performing the STFT, the smallest resolvable frequency difference $\Delta f$ is fixed by the number of samples L in a window of time $T_L$ as: $\Delta f=1/T_L$ (Orfanidis, 1996, p. 474). Longer time windows have lower time resolution due to averaging. A limited time window causes spectral leakage from two sources: (1) analysis frequencies do not correspond exactly to data frequency components (zero padding can help by interpolating), and (2) edge effects of the finite window (reduced by a data-tapering function at a cost to frequency resolution). The aspect of time information that the STFT retains is the time offset of each sequential STFT window (Northrop, 2002, p. 42). By changing the overlap of successive windows from 0% to 50%, the effective time resolution is changed from $T_L$ to $T_L/2$. Window size and shape can be optimized, but once it is fixed it establishes a lower bound C on the product of variance of time t and frequency f which may be recognized as the uncertainty relation: $\Delta t \cdot \Delta f \geq C$. The mentioned spectral leakage also raises C. In contrast to the fixed time resolution $\Delta t$ of the STFT, the time resolution varies (inversely) with the number of samples spanned in the WT. Another difference is that the STFT frequency resolution $\Delta f$ varies (directly) with L, but is fixed by the sampling rate in the WT. This explains the findings of a study of hand written character recognition (analogous to IEGM event recognition) which found that Fourier based features had larger intra-class variance $\Delta t$, and weaker inter-class separation $\Delta f$ than the same number of wavelet coefficients (Theodoridis and Koutroumbas, 2003, p. 257).

However, the STFT assumes stationarity over at least the window length. Therefore, features that are distinguished from each other and occur in time shifts smaller than the size of the STFT window are lost. For example, if two P waves (atrial depolarizations) in the IEGM are differentiated by a change in signal shape at a sample offset shorter than the time resolution fixed by the window size, the STFT is not helpful. Sequencing the $|STFT|^2$ for display will produce a three-dimensional surface (magnitude spectrogram) whose axes are frequency, time, and energy. Fourier analysis will not be considered further, because with less processing, the wavelet transform has both good time resolution for high frequency events, and good frequency resolution for low frequency events.

Interesting biological waveforms are non-stationary signals; in fact, the features of interest are often sudden changes, discontinuities, or edges. In addition, interesting features, some of which are small, occur at specific time offsets within the data. Historically, the development of filter banks was an attempt to design filters that corresponded to the long and short time scales on which features can be seen (Mallat, 1999, p. 8). The resolution of the filter should match the scale of the feature of interest. The property of a transform that is able to reveal features simultaneously at large and small scales is called multiresolution, and is an important property of the WT.

In the case of a depolarization event, a specific time window of samples is taken, because that is where the interesting information is located, and the signal outside this time window is generally considered interference. This time limited window is called 'compact support.' The wavelet itself is a basis function that is localized in time and frequency. Because calculation of wavelet coefficients requires adjacent samples on either side of the time sample, the samples at the window edge must be dealt with by extension, such as, zero, linear, reflection, or periodic. The wavelet transform splits the finite sample time sequence into smooth and detail coefficients. Though ideal ('brick-wall') low pass (LP) and high pass (HP) filters are capable of generating the hierarchy of smooth and detail values from the original sequence (Theodoridis and Koutroumbas, 2003, p. 239), these filters are not feasible and the processing cost to approximate them would be inappropriate for this work.

Figure 25:
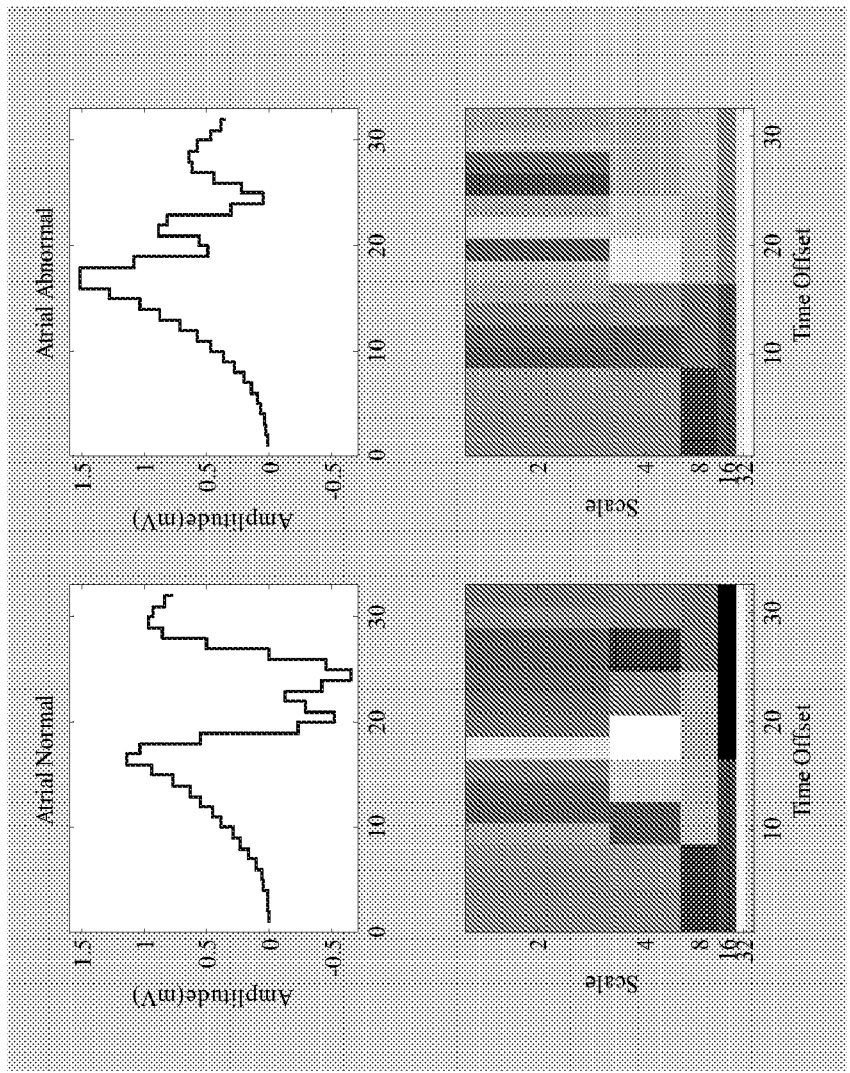
FIG. 25 shows the wavelet scalogram shows two examples of the hierarchal generation of the wavelet coefficients from a single data window.

The Wavelet Transform (WT) itself generates a series of time-shifted spectra, but when the energies are arranged on axes of time offset versus scale (number of samples spanned by the scaling of the wavelet); the resulting spectra can be viewed from above as a surface. Like the STFT, the WT of a finite sample one-dimensional signal also results in a three-dimensional surface (scalogram) whose axes are correspondingly scale, time offset, and average energy (van den Berg, 2004, p. 83). FIG. 25 shows this. The figure is organized as follows. In the upper subplots the two windows of data are atrial normal event (left) and atrial abnormal event (right). The horizontal axes are time offset from the beginning of the event. The vertical axes are the amplitude. The lower subplots are the corresponding scalograms for each event where the vertical axis is scale, and the energy surface is normalized to an 8 bit grayscale (black=–128, and white=+127). Notice that the scalogram from top to bottom is organized into horizontal 'sub-bands.' All the values within a sub-band are at the same scaling of the wavelet at different time offsets. The scalogram appears coarse because unlike a continuous wavelet transform, the discrete wavelet transform is limited to the time resolution ($f_s$=512 Hz) of the input signal. All rectangles in the scalogram have equal area, where the time resolution is proportional to rectangle height and frequency resolution is proportional to its width. The first sub-band at Scale=2 spans the frequencies from 128 Hz to 256 Hz. Scale=4 spans the frequencies from 64 Hz to 128 Hz, and continues down to the penultimate coefficient spanning 16 Hz to 8 Hz, and the last coefficient that spans 8 Hz to 0 Hz. The WT scalogram differs from the STFT in two ways: (1) this scalogram is not a sequence of windows but a single data window, and (2) the resolution of this scalogram is not limited to the window width but down to the time difference between each sample. If a time windowed signal has a feature of interest, such as, a slope or a peak, it is reflected by a concentration of the energy in the coefficients corresponding to that time offset in the waveform. The example atrial depolarization events in the figure shows the scalogram tracking the salient features of the time domain signal by the greatest contrast in gray. This figure introduces the energy surface produced by the wavelet transform algorithm. A cursory examination shows the two scalograms are indeed different.

The WT is dependent on the sampling rate $f_s$, in that the upper frequency limit of the most detailed WTC is the Nyquist rate ($f_s/2$=256 Hz). 99.99% of the spectral content of the IEGM is $f_c \leq 175$ Hz (Schreier, Kastner, Hutten, 1999, p. 400). Previously (in §Pre-processing of the IEGM), a sampling rate of $f_s$=512 Hz was justified by clock jitter and the transition band of a realizable filter. One may ask, 'Why not increase $f_s$ and get more time resolution?' First, because the higher Nyquist limit would then produce a detailed sub-band $[f_s/4 \ldots f_s/2]$ of pseudo-content $\geq 175$ Hz requiring unnecessary processing to reject it at the feature selection stage and possible degradation of classifier accuracy.

The WT provides compact support, therefore, a limited time window $T_L$ is selected, such that, $T_L=L/f_s$. Here, L is an integer power of two chosen just large enough to assure that expected IEGM event durations $T_d \leq T_L$. Therefore, the second reason not to increase $f_s$ is that the number of samples to process will increase proportionally without benefit.

Processing the first sub-band is now wasted (because $f_c \leq 175$ Hz), but must be performed anyway to generate discriminating features in later sub-bands. Neither can the WT, unlike the STFT, improve its time resolution $\Delta t$ by increasing L alone without also increasing $f_s$. Thus, a sampling rate of $f_s=512$ Hz with correct estimate of $T_L$ is appropriate for this work.

Time Scale Correlation of the Wavelet Transform

The fundamental operation that produces a smooth wavelet value is correlation with the wavelet filter function. The detail coefficient is the residual from this correlation. The wavelet transform is completed by repeating the correlation only on the remaining smooth coefficients. To preserve the convolutional wavelet transform property of orthogonality between even shifts, the pyramidal version of the transform applies decomposition recursively only to values with even parity (Rioul & Vetterli, 1991, p. 29). There is a wide variety of wavelets, but beyond the Harr, Line, and Daubechies 4, the rest have poorer time localization because of longer filter length. Additionally, processing increases by the power of the filter order, therefore these other wavelets are not suitable for the intended purpose of this work (Goswami & Chan, 1999, p. 118).

'Analysis' is the forward transform decomposition of time samples into coefficients. Synthesis is the reverse transform, that is, it restores the original time domain samples without loss. In that case, the synthesis filters are the time reverse of the analysis filter. Wavelets transforms with this perfect reconstruction property are also orthogonal (Theodoridis and Koutroumbas, 2003, p. 244). This disclosure limits the discussion of synthesis to explaining certain properties of the line wavelet transform.

Generating Wavelet Transform Coefficients

The generation of wavelet transform coefficients in this work is non-adaptive, since (1) the same pair of operations are repeated to decompose each pair of smooth and detail values, and (2) the transform does not vary the pyramidal tree structure or the basis (other than by scaling) to achieve decomposition (as is done in 'wavelet packets,' a compression oriented scheme). A group of wavelet coefficients produced by one scaling of the wavelet filter is called a 'sub-band.' The initially computed sub-bands locate details in time with finer resolution. The later computed sub-bands provide scaled replicas of the smooth features with less absolute error.

When the WT is performed on the time samples from an event, the smooth and detail features are separated for each scaling of the wavelet kernel. The transform is repeated only on the smooth features in the sub-band producing the values to be operated on in the next sub-band. Eventually, there is a single smooth coefficient and the recursion stops. This smoothest value approaches the arithmetic mean of the event. The last smooth value should be rejected as a feature, because 0 Hz . . . 8 Hz includes a value representing the mean value of the event (refer to FIG. 15 and §Time Localization Property of the Wavelet Transform). The wavelet transform produces N coefficients from N original time samples.

Dimension Reduction Property

The purpose of this section is to describe the dimension reducing property of the wavelet transform using linear estimation as an example. Non-adaptive methods can represent a signal as a linear combination of basis functions (Cherkassky, 1998, p. 235). An example of this is the standard regression model whose formula is: $y=X \cdot \beta + \epsilon$. The n×1 response vector y has limited energy, and n is the number of observations. The n×p design matrix X has columns $x_k$ (k=1, 2, . . . , p) of explanatory 'factors,' 'variables,' 'covariates,' or 'regressors'. Elements of the p×1 parameter vector $\beta$, are regression coefficients (slopes) weighting the model vector to producing a fixed effect. The n×1 error vector $\epsilon$, are the residuals, assumed to be independent of X and y, and normally distributed or $\epsilon \sim N(0, \sigma^2)$. Thus, $y_i = x_{i,1} \cdot \beta_1 + \ldots + x_{i,p} \cdot \beta_p + \epsilon_i$, for i=1, 2, . . . , n. The deterministic variance of the model is controlled by $X \cdot \beta$, and $\epsilon$ is the stochastic variance in the model. The coefficients $\beta$ can be uniquely estimated by a minimization method, such as, linear least squares giving $\hat{\beta} = (X^T \cdot X)^{-1} \cdot X^T \cdot y$, where T is the transpose operator. The response can now be estimated $\hat{y} = X \cdot \hat{\beta}$, and the residuals are $\epsilon = y - \hat{y}$.

Because the standard solution to the linear model does not decrease the number of predictors $\hat{\beta}$, an overfitted model often results (Militký, Karel Kupta, & Meloun, 1998, p. 882). Consider simplifying the previous standard regression model example by disregarding the error, and the linear system becomes: $y = X \cdot \beta$. To solve for $\beta$, one can solve for $X^{-1}$, or perform Gaussian elimination. A solution for this is the Hotelling (Karhunen-Loéve) transform, which can also solve for $\beta_\perp$, by projecting $\beta$ the most important directions (eigenvectors) in decreasing order. Smaller vector elements of $\beta_\perp$ can be discarded leading to a parsimonious model that minimizes generalization error on a validation data set.

However, not an Eigen decomposition, the wavelet transform also projects the linear system so that it is oriented in the most important direction with respect to the wavelet basis. The design matrix X must be square, and full rank. The matrix form of the one dimensional wavelet transform W is unitary ($W^{-1} = W^T$) and orthogonal because all its elements are real. X can be transformed to a similar matrix $\tilde{X}$ by applying the wavelet transform: $\tilde{X} = W^T \cdot X \cdot W$. The trace (diagonal) of $\tilde{X}$ contains linearly independent elements approximating eigenvalues. Proceeding, y is also transformed similarly: $\tilde{y} = W^T \cdot y$. $\tilde{\beta}$ can be defined by $\tilde{y} = \tilde{X} \cdot \tilde{\beta}$. Small matrix elements of $\tilde{X}$ are now set to zero, and may reduce the size of $\tilde{X}$ and $\tilde{y}$ both allowing easier solution of $\tilde{\beta}$ (Bultheel, 1995, p. 35). The original parameter vector can be recovered as: $\beta = W \cdot \tilde{\beta}$.

Having shown the dimension reduction properties of the wavelet transform in the simple case, the error is restored to the standard regression model example for the following reason: Noise in biological signals often has a 1/f power spectrum that is temporally autocorrelated, therefore exhibiting some memory or self-similarity. Hence, the error vector is actually $\epsilon \sim N(0, \Sigma)$, here the covariance matrix $\Sigma = \sigma(X^T X)^{-1}$ is symmetric, now with non-zero off diagonals that confound the estimation of linear regression model parameters and their standard errors. By wavelet transforming the linear model: $y_w = X_w \cdot \beta + \epsilon_w$, the error vector is whitened. Here w indicates the application of the wavelet transform W, in the case of X transforming column-wise. With the new error vector, the parameters are now estimated by: $\hat{\beta} = (X_w^T \cdot \hat{\Sigma}_J^{-1} \cdot X_w)^{-1} \cdot X_w^T \cdot \hat{\Sigma}_J^{-1} \cdot y$, where $\hat{\Sigma}_J^{-1}$ is the inverse of the diagonalized covariance matrix, and J indicates the sub-band of the wavelet transform (Fadili & Bullmore, 2002, p. 222). The off-diagonal matrix elements of $\Sigma$ are set to zero simplifying its inversion. In the online case, $\Sigma$ does not have to be solved and inverted, rather $\hat{\Sigma}_J^{-1}$ can be solved in place sequentially (Kay, 1993, pp. 242-250). Thus, like principal components analysis, the wavelet transform also has the ability to represent the signal in a non-redundant subspace and whiten the noise, but at a much lower cost (see §Feature Selection for the Purpose of Classification).

Properties of the Line Wavelet Transform

The Daubechies wavelets, for example Daubechies 1 (Haar) and Daubechies 4, are orthogonal, produce non-redundant data, and have compact support (Cherkassky, 1998, p. 248). Although the line wavelet transform is not an orthogonal transform (scaling function is orthogonal to any even valued shifts of itself), it is a biorthogonal transform (nearly orthogonal) because it splits the scaling function into smooth and detail filters that are orthogonal with each other. Additionally, the biorthogonal wavelet is symmetric (unlike orthogonal transforms), non-redundant (like orthogonal transforms), still allows perfect reconstruction, and has compact support (Hubbard, 1998, pp. 242-243). Unlike orthogonal wavelets (except the Haar), the biorthogonal transforms can be implemented as symmetric FIR filters. The line wavelet is a wavelet whose basis function is a straight line, and satisfies the following requirements of a proper wavelet: (1) it is bounded in frequency response, that is, it is a band pass filter (Cherkassky, 1998, p. 247), and (2) it has zero mean (Valens, 2004). Each transform step is an interpolation between two adjacent points, and the basis effectively translates so that one of the basis points is the origin. The difference value tracks the offset between the predicted point and the actual value. If the original time samples are of finite energy, that is, they have a finite L-2 or Euclidean norm, then so will the resulting WT coefficients. Lastly, the line wavelet functions as a band pass by performing low pass filtering repeatedly on smoothed data points, and as an effective high pass filtering function due to the differences separated out into coefficients (HP).

Reducing Processing in the Wavelet Transform

Figure 26:
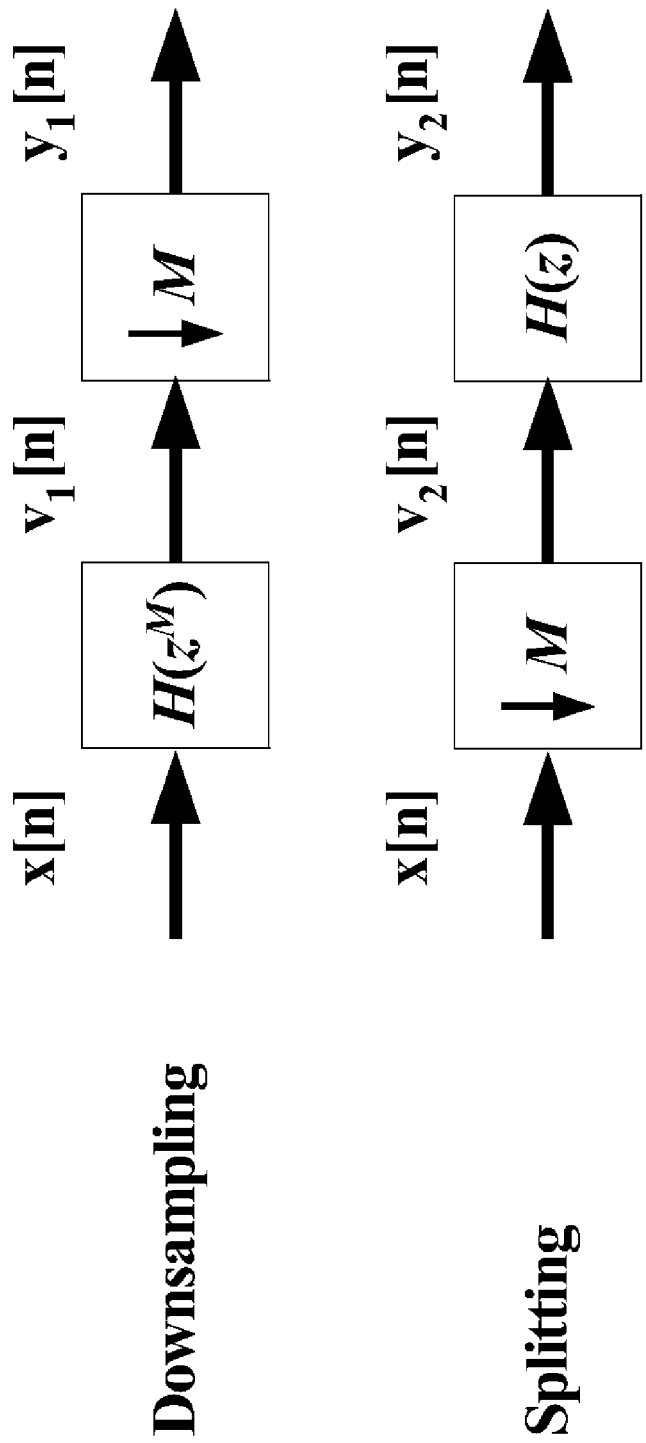
FIG. 26 shows the processing efficiency can be improved through a cascade equivalency.

The implementation of the WT has evolved as mathematical insights rendered more efficient methods, as occurred also in the history of the FFT. Originally, WT were implemented as matrices, then as FIR filters. For example, when the coefficients of a low pass filter $h_1$ are known for the WT, its corresponding coefficients for the high pass filter $h_0$ can be directly calculated by: $h_0(n) = -1^n \cdot h_1(-n+2 \cdot L-1)$, where L is length of filter (Theodoridis and Koutroumbas, 2003, p. 244). For the input samples at any step of the transform, the 'dyadic' result is a pair of smooth-detail coefficients. When the WT is implemented as a convolution, it yields a count of detail plus smooth coefficients equal to twice the number of values found in the original sample. Downsampling by two for each sub-band controls the scale relationship between the data and the wavelet with the additional benefit of conserving the number of samples. The downsampling operation can be placed prior to a linear operation by means of a cascade equivalency (Mix and Olejniczak, 2003, p. 11). In FIG. 26, x[n], v[n], and y[n] are the discrete time input, intermediary signal, and output, respectively. The upper portion of the figure shows the method of 'Downsampling' after filtering used by the filter bank implementation of the wavelet transform. The lower portion of the figure shows the method of downsampling before filtering, which leaves fewer samples to be processed by the filter, but has an identical transfer function.

Let $W_M^{kn} = e^{-j2\pi kn/M}$ and $z = e^{j\omega}$ given that the Discrete Fourier Transform (DFT) of the factor M downsampler is:

$$H(z) = \frac{1}{M} \sum_{k=0}^{M-1} G(z^{1/M} W_M^k),$$

for input g[n] and output h[n]. The DFT for the first intermediary signal is: $V_1(z) = H(z^M) \cdot X(z)$, and the first output is:

$$Y_1(z) = \frac{1}{M} \sum_{k=0}^{M-1} H(zW_M^{kM}) X(z^{1/M} W_M^k) = \frac{1}{M} \sum_{k=0}^{M-1} H(z) X(z^{1/M} W_M^k).$$

The second intermediary is:

$$V_2(z) = \frac{1}{M} \sum_{k=0}^{M-1} X(z^{1/M} W_M^k);$$

and $$Y_2(z) = \frac{1}{M} \sum_{k=0}^{M-1} H(z) X(z^{1/M} W_M^k).$$

So $Y_1(z) = Y_2(z)$ (Mitra, 2001, pp. 667-671). (Note: There is also a cascade equivalency for upsampling that applies only to wavelet synthesis, where the aliasing caused by downsampling is cancelled.)

See:

Relocating the downsample operation is one improvement of the lifting version of the wavelet transform over the convolution version called 'splitting' which makes each step more efficient as it is done on half the samples. Overall, the Lifting Transform (LT) has O(n) complexity (Daubechies & Sweldens, 1998, p. 264). Though convolution method wavelet transforms using iterated FIR filters have computational complexity $O(n^2)$, a lifting equivalent is possible for all of them (Rockmore and Healy, 2004, p. 194). Additional explanation of the implementation of the modified lifting line wavelet transform, not found elsewhere, is given in the Chapter 7.

Alternate Methods Considered

The scalogram (FIG. 25) is not limited to the WT. Radial Basis Functions (RBF from neural networks) have center and width parameters that are reminiscent of the time and scale parameters of the Gabor WT (Cherkassky, 1998, p. 236). A variation on this theme uses an RBF wavelet transform kernel for classifying IEGMs (Strauss & Steidl, 2002, p. 12). However, neural network methods pose an unacceptable risk in an implanted device, because there is no guarantee that any particular learning instance will not lead to a dangerously inadequate outcome (Lendaris, 1991, p. 2). Neural networks yet remain an effective tool for proof of concept. Although neural network methods are analogous to statistical methods and pursue the same objectives, statistical methods guarantee more reliable outcomes (Sarle 1994).

Suitability of Gaussian Assumption

The purpose of this section is to consider the appropriateness of the assumption of Gaussianity on wavelet-generated features. Wavelet coefficients are compactly supported; that is, the basis function, and therefore the resulting coefficients, are zero outside the analysis window. Additionally, the line wavelet transform preserves only the first (mean) and second moment (variance), therefore in keeping with the Gaussian model all cumulants of order three and higher vanish (Weisstein, 2004). As discussed in §Dimension Reduction Property, the wavelet transform renders the signal into a sparse representation of a majority of small valued coefficients, and a few large valued coefficients. This occurs because coefficients become smaller farther away from edges, and larger near them. Though the wavelet transform may have a whitening effect on other variables (§Dimension Reduction Property), the wavelet transform coefficients themselves are found to be poorly Gaussian on natural signals. That is to say, they have kurtotic distributions with statistical inter-dependence between values and their variances (Wainwright & Simoncelli, 2000, p. 855). However, the ROC meets the need for a distribution-free method of assessing the discrimination power of the WTC.

Selecting the Best Basis

From a library of wavelet bases, a particular basis can be selected for each sub-band or separate decompositions within a band (van den Berg, 2004, p. 17). The purpose of decomposition by a customized set of wavelet bases, 'wavelet packets,' is to optimize some objective, such as, interference reduction, compression, or both. The discussion in the literature about a custom wavelet basis for the classification criterion appears to equate optimization for compression with optimization for classification. A little consideration can dispel the correctness of this assumption. Compression and feature reduction for classification are both lossy, but compression may retain features that cross-correlate between event classes and discard the very features that allow discrimination between them. A set of wavelet packets for classification of IEGMs will not be addressed in this paper, particularly because of the computational infeasibility of implementing a library of transforms in a processing limited device. Table 3 shows that the three simplest wavelet transforms (Haar, Line, and Daubechies 4) have rapidly progressing complexity. A pair of analysis filters is shown for each transform: (1) the detail (wavelet) filter produces the coefficients $c_n$, and (2) the smoothing (scaling) filter produces averages $a_n$. There are several reasons to choose the line wavelet transform over the others. The Haar wavelet transform can miss a feature occurring on the boundary between an odd and the following even data value. All other wavelets after D4 are more complex to implement in length, and have irrational coefficients. The factor of three in the smooth Line wavelet filter disappears in the Lifting form of the transform. An additional insight was that the energy conserving scaling factor $1/\sqrt{2}$ could also be dropped from the implementation since the feature distributions between categories are unchanged with or without it.

The Goal of Feature Reduction

Applying the wavelet transform (WT) to a window of N IEGM signal samples results in N WT coefficients (WTC). Due to finite battery capacity, it is desirable to process the least number of WTC sufficient to perform event discrimination correctly with 95% accuracy. In the statistical learning model, relative weighting (Cherkassky, 1998, p. 128) should penalize poorly performing features (WTC with lower discrimination). After ranking, a method of relative weighting by, for instance, the signum function would penalize poorly performing features and provide a smooth transition from used to unused WTC. However, a definite cutoff that leaves a small number of WTC is preferred, to reduce the processing load that scales with the feature count.

The bi-orthogonality of the line wavelet transform provides orthogonality between sub-bands, but not between WTC within a sub-band. Thus, any WTC retained after ranking and pruning that are also members of the same sub-band, are redundant to the extent that they co-vary.

Next, the widely used ranking of WTC based on a coefficient magnitude method will be described. Then the alternate method used in this study, ranking by discrimination, will be presented.

Coarse Scale Selection of Coefficients

It is desirable to employ a method that compactly, yet accurately, represents some arbitrary finite energy differentiable function. The wavelet transform accomplishes this goal and allows a tradeoff of accuracy versus compactness of representation. To accomplish dimension reduction, some wavelet coefficients must be de-emphasized or discarded. In the existing literature, the typical approach is to set any wavelet coefficients below a fixed threshold to zero (Cherkassky, 1998, p. 249), removing them from future calculations and classification decisions. An additional step is to rank the coefficients by magnitude from greatest to least and only the first m number of coefficients is used to define the classifier (Cherkassky, 1998, p. 250). This ascendancy of coarser features over finer features is the method of 'greedy learning' in pattern recognition systems (Cherkassky, 1998, p. 251). When the goal is merely compression of the waveform, this method is a simple, effective solution. The problem with this approach is that wavelet coefficients are discarded with respect to amplitude, and not by ability to classify the event. An improvement over magnitude-based feature selection is ranking according to reduction of classification error (Cherkassky, 1998, p. 250). The Receiver Operating Characteristic curve is a means to evaluate features against this latter criterion.

The Receiver Operating Characteristic Curve

Refer to Table 4 for the definition of parameters used in generating the Receiver Operating Characteristic (ROC) Curve, where T=true, F=false, P=positive, and N=negative. The following axioms also apply, where the a priori probability Actual$_{Class2}$ is the annotation in the IEGM test file:

$$TP = P(\text{Test}_{Class2} | \text{Actual}_{Class2}), 1 = TP + FN, \text{ and } 1 = TN + FP$$

The ROC curve is a plot (right hand column of FIG. 27) of recall versus false alarm rate characterizing the discrimination of a single feature. Each point on the plot is determined by the resulting sensitivity versus (1−specificity) as the threshold that separates two categories is varied. ROC space lies within the bounds x=[0 . . . 1] and y=[0 . . . 1]. Increasing values of the threshold in the left hand subplots corresponds to tracing the ROC curve in the right hand subplots from the point (1, 1) through the curve to the point (0, 0). The ROC curve is concave (decreasing slope as false alarm rate increases). If the curve goes below the no-discrimination line y=x, it means the two category labels are on the wrong side of the threshold. A curve approximating the line y=x indicates that, regardless of the threshold value, the categories are inseparable with this feature; that is, one can do no better than flipping a coin.

Figure 27:
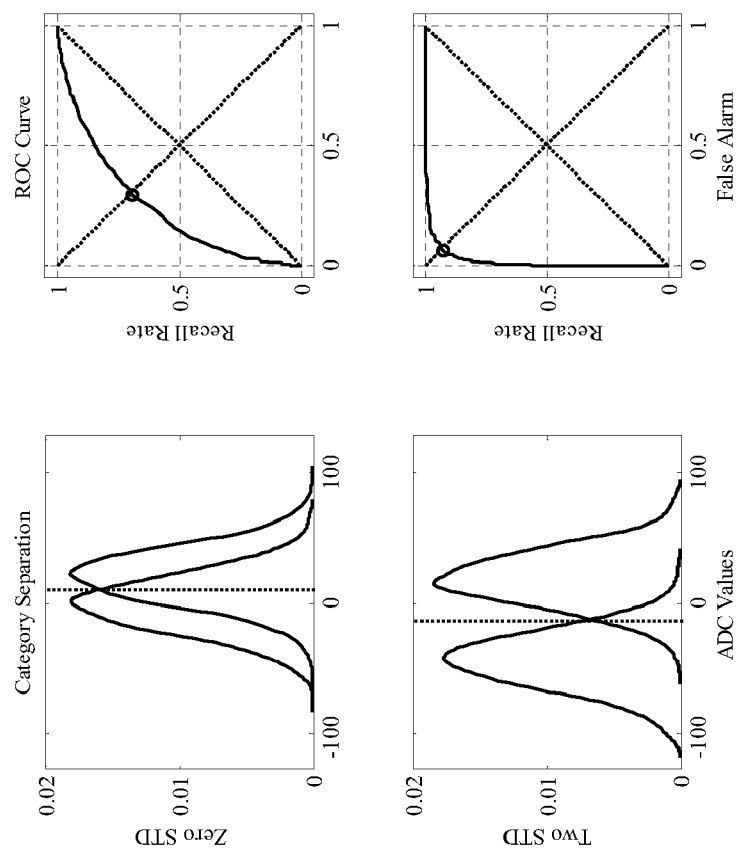
FIG. 27 shows the separability of two conceptual distributions corresponds to the ROC AUC, whose most discriminating threshold corresponds to the ROC vertex.

FIG. 27 shows two examples of pairs of feature distributions for two categories in the left hand column. The separation between category means is seen to increase as the plots go from top to bottom. The corresponding increase in area under the ROC curve (AUC) can be seen in the plot to the right. The feature distributions shown in this example have the same variance. Increasing the variance of the feature around a category mean would correspondingly reduce the AUC.

As the separability of the features improves, the vertex of the curve approaches (FP=x=0, TP=y=1). The line y=−x+1, which is ⊥ to the no-discrimination line y=x, will intersect the ROC curve at the vertex marked with a circle ○ for a normally distributed feature with equal class variances, and is the most discriminating threshold achievable in this case. The closer the vertex is to the point (0, 1), the better performance of the selected threshold. In practice, the ROC curve will not reach this perfect condition (FP=x=0, TP=y=1), because the feature distributions of interesting problems have a non-zero overlap. There are two main non-parametric measures that summarize the ROC curve in a scalar value: (1) the area under the ROC curve (AUC) or 'discrimination' within ROC space, and (2) the Euclidean distance $d_v$ between the point (0, 1) and the vertex of the curve (marked with a circle ○ in FIG. 27). A number of asymmetries between the classes may shift this vertex off the line y=−x+1, such as, unequal variance, unequal sample size, or unequal costs. Note: In the case of unequal costs, the best threshold corresponds to the point on the ROC curve where the slope is: $dROC/dFP = P_N \cdot (C_{FP} - C_{TN})/P_P \cdot (C_{FN} - C_{TP})$, P is the a priori probability of an event class and C is a relative cost (van Schalkwyk, 2003). Because these parameters are unquantified in the literature, equal prior probabilities and costs will be assumed for this work. Although unequal prior probabilities of arrhythmias, unequal costs of mortality and discomfort are apparent, there is a preference for treatment built in to medical decision making and devices (refer to §Justification of Work).

This disclosure proposes ranking coefficients by two criteria. First, coefficients will be ranked by, AUC and those below certain discrimination ability are discarded. Second, the best threshold achievable to separate to categories will be indicated by the vertex of the ROC curve where $d_v$ is minimum. The ROC analysis is a classifier-free method to test the separability of the features without instantiating a classifier, such as, a kernel discriminant. It is not within the scope of this work to develop an implantable version of the ROC ranking method and measure its device processing cost. Demonstration of this method on a workstation is sufficient. ROC analysis can be performed on the external programmer (computer) at no processing cost to the implant other than transmitting raw data and receiving the pruned WTC.

Combining Features

The nominal ROC AUC method analyzes features one at a time, where a single threshold separates a feature into regions corresponding to two event classes. This method can be extended to include combinations of the available features, where the number of AUCs to be determined for one subset is: $\Pi f_1, f_2, \ldots, f_r$, where f is the number of threshold steps to be evaluated for AUC for one feature and r is the number of features in the subset. The number of combinations generated for comparison is:

$$\sum_{r=m}^{n} \frac{n!}{r!(n-r)!},$$

where m and n are the least and greatest number of features in a subset respectively. Subsets containing more than one feature may or may not have a higher joint likelihood of more discrimination. If categories overlap less in the joint feature space, then features ranked highly as individuals would have greater discrimination in a subset than alone. In general, the best thresholds for a feature evaluated singly and in a subset will not be equal unless all cases not wholly above or below the joint thresholds are placed in a rejection class. Highly performing features must degrade when they are in a subset with a poor performer. A smaller subset or single feature would be preferred as it would be easier to evaluate and the risk of overfitting is lower. If upper and lower limits around a class mean of a feature are to be explored as an alternative to a single discriminating threshold, each independent limit value must be treated as a separate $f_r$. Combining features is not within the scope of this disclosure, it will be sufficient to show that the AUC ranking method can find at least one WTC in a sub-band capable of sufficient discrimination.

Chapter 4

Design

Problem Statement

Wavelet based feature selection addresses the problem of extracting features from a time domain signal (IEGM depolarization events) and retaining the most salient of these features. The line wavelet transform (LWT), which is free of multiplications involving float and integer values other than 2 and 4, was selected to minimize processing in the implant. The choice of the LWT provides the simplest wavelet capable of resolving all time domain features regardless of sample parity. The ROC will serve as a proxy for a 2-category (normal versus abnormal events) classifier, where events belonging to rhythm classes are categorized, not the rhythms themselves. The 1-out-of-C classifier, where the number of categories C>2, can be implemented by the repeated application of a 2-category classifier, though this is outside the scope of this work. This chapter will explain the lifting version of the LWT. Methods necessary to process the IEGM and wavelet feature extraction, will also be introduced in this disclosure.

Alignment of Event on the Peak

This disclosure proposes a method to gather several events and align them in time on a fiducial point; that is, samples are aligned so that the peak magnitude for all events of a class has sample index N/2, where N is an integer power of two.

The bipolar lead is a point of observation in the heart analogous to the volumetric derivative. Therefore, it has less sensitivity to the wavefront when it is distant ('far field') from the lead, and more sensitivity as it passes through the local observation area ('near field'). The signal to noise ratio then is the highest when the peak is being generated. An IEGM peak is an effect created when the electrical wavefront causes a net charge difference on one of the contact elements with respect to the other (refer to FIG. 12). There are usually at least two major peaks of opposite polarity, each one for the voltage differential created by the wave passing past each electrode. The wavefront is halfway between the two electrodes when the IEGM passes through zero in between the two peaks. The electrical field leaves the contact elements temporarily slightly polarized, which places the actual zero crossing location in doubt. Therefore, the first and second peaks are notifications of the beginning and ending edges of the passing wavefront.

Peaks are easily identifiable features in the IEGM, generating the apparent non-linear change in amplitude and a sharp discontinuity when reversing the second derivative of the amplitude (often within the time of a single sample (see FIG. 60). As described in §Time Localization Property of the Wavelet Transform, features that change quickly (peaks) have higher time resolution than those that change slowly. To summarize, the near-field SNR and time resolution of the peak make it a preferred feature on which to synchronize events. The peak alignment method is shown in Table 5.

1. Discrete time IEGM samples continually enter a length N FIFO buffer.
2. If the blanking period is over and an amplitude threshold crossing is detected:
    a. Start a blanking period.
    b. The peak alignment counter is set to N/2 counter.
    c. The absolute value of the present sample is stored as maxValue.
3. While 0 < N/2 for each new sample:
    a. If the absolute value of any subsequent sample exceeds maxValue,
        i. The absolute value of the present sample is stored as maxValue.
        ii. The N/2 counter is reset (slip).
    b. Else, decrement the N/2 counter.
        i. maxValued sample moves toward the center of the buffer.
4. If the N/2 counter reaches 0:
    a. Store the present length N FIFO buffer into a memory location.
    b. Event will be aligned on electrical field maximum.

After these steps, it is still reasonable to ask if the true peak is now accurately centered in the memory location. If the actual peak amplitude value comes after a previous maxVal and does not differ by more than the ADC resolution, the true peak will not be centered. The sampling times of the ADC are not synchronized with the IEGM; therefore, the value latched may be only near a peak. Noise increases the uncertainty because of summation with the peak and other nearby samples. Lastly, the group delay of the signal path disperses the true energy peak seen at the evaluation point inside the implant.

Collection of samples for the event classes is performed during the definition phase. During the reference phase, peak centered events of each category are collected and wavelet transformed. Data collection requires storage of 2×m×n values, for two classes, of window size m, for n reference events. Transformation generates the same number of WTC values as data values. During the evaluation phase, yet unseen events are also peak centered and wavelet transformed. In this latter phase, new WTC are evaluated by thresholds found earlier by ROC analysis to best separate the reference WTC based features.

The definition phase is based on the assumption that within a stable rhythm, such as Normal Sinus Rhythm, reference events will be consistent. For the noise process contaminating amplitude values in these events, there is no self-correcting process implicit in collecting additional events for averaging (Tversky & Kahneman, 1971, p. 106). As the number of samples taken for averaging increases, initial variances are diluted by subsequent measurements and initial mean values regress toward the distribution means (Arnott, 1998, p. 17). To be sure, there are other noise sources outside the body that are periodic, but these are attenuated by the near-field view of the bipolar lead, and by encapsulation of the entire sensing system in the electromagnetic shroud of the human body. Additionally, the input stages of modern IPG and ICD sensing systems have EMI protection and decoupling capacitors to minimize DC offset effects.

Figure 28:
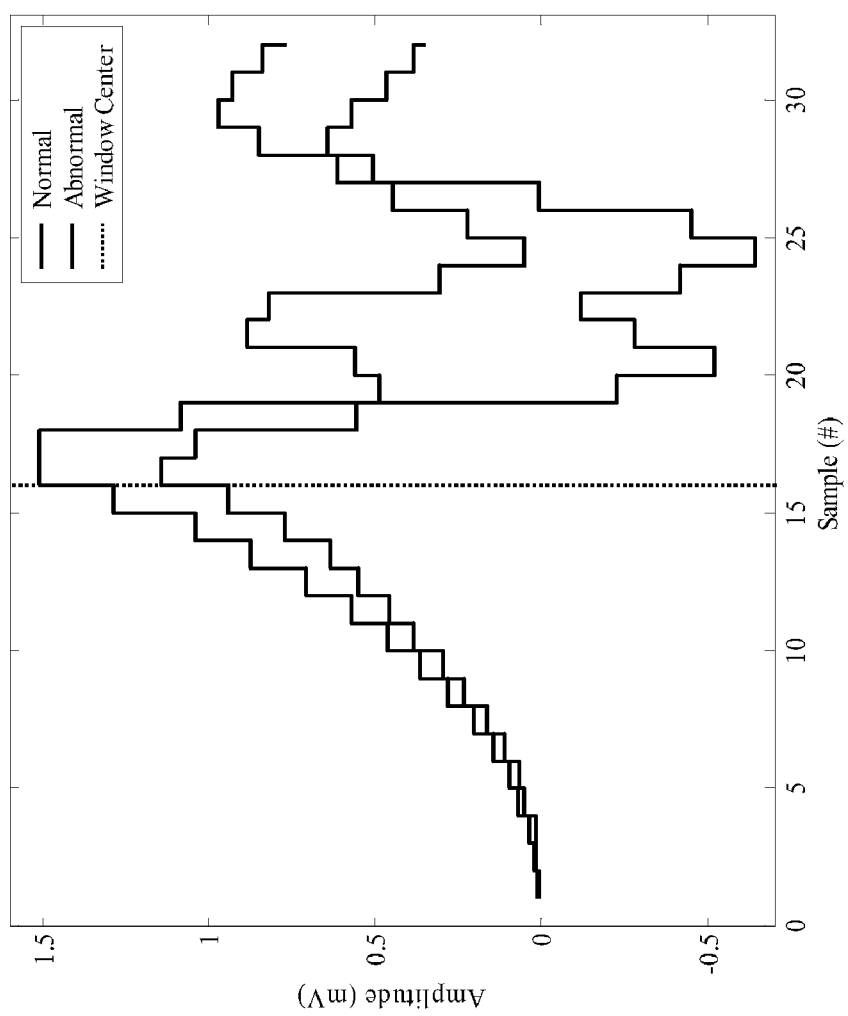
FIG. 28 shows the peak alignment of events from two different categories.

FIG. 28 shows that the normal and abnormal events referred to earlier peak aligned in the 32-sample buffer (62.5 ms at 512 Hz). Both events are aligned by centering the peak magnitude sample on the $16^{th}$ sample of the sampling window.

Errors in Event Detection and Peak Alignment

For the event detector, the input signal is sampled at uniform time interval. The sampled data are quantized with a uniform step size (§Pre-processing of the IEGM). Signal data spanning the event of interest is buffered prior to LWT decomposition. Errors associated with LWT decomposition include all the errors of the sampling and quantization system, and the synchronization of the event with its marker. The Wavelet Transform operates on the post-ADC representation of the signal data and therefore inherits those limitations of quantization, finite precision, round-off, overflow, and scaling. Additionally, the Wavelet Transform is not shift invariant so it is important to align depolarization events accurately on the peak fiducial point. The 'slip' method (§Alignment of Event on the Peak) disambiguates the situation of more than one peak by selecting the one with maximum amplitude. If multiple peaks are exactly equal, the first peak will be selected (preferred because slew rate is highest).

The traditional threshold crossing to provide for the relative timing of events has built-in inaccuracies. Even after DC removal, there remains a variance in the point on the slope of the initial upstroke of depolarization where it crosses the comparator trip point (variance is also proportional to slope). For the purpose of this work, the event detection marker generated by the threshold crossing indicates only that the event retrieval system should start collecting samples of interest for the LWT. The 'slip' method (Table, step 3.a.ii) causes all events of a given class to be peak aligned on the same central sample number in the buffer.

The error in event alignment can be reduced but not eliminated. For example, the depolarization peak is independent of the sample time of the quantizer. Therefore, the resulting variance in time from baseline to peak in the post-quantizer-sampled waveform may vary from beat to beat more than in the actual waveform. This can be reduced by increasing the sampling rate, with tradeoffs (§Pre-processing of the IEGM). Two mitigations, not investigated here, would be the signal averaging of several exemplars from the same class, or making multiple time offset definitions for an event of the same class (Schomburg 2002).

Compression-Oriented Best Basis Approach

One may ask, 'Why not design a wavelet customized for the depolarization event?' The 'best basis' method has a custom filter for each sub-band, with the following tradeoffs: (1) each basis in the library must have a uniquely designed filter pair (there is no general method to design a wavelet filter), (2) each filter will take up its own space (code or hardware), (3) the application of the various bases therefore cannot be rolled up into a compact recursive routine, and (4) all other wavelet transforms than the three introduced earlier are higher in filter order, increasing processing while reducing time resolution in proportion to their increased length. Best basis is a compression-oriented approach, and its goal is to optimize the choice of wavelet filters so that the signal energy is concentrated in the smallest number of last computed WTC. Recall that the value of a coefficient is the residual from correlation with the wavelet basis. A measure of 'accuracy,' in this sense, is inversely related to the amount of energy is in the earliest computed sub-bands. However, because of the earlier points in this section, best basis is not suitable for this work. In contrast, the line wavelet transform (LWT) uses the same operation throughout the recursive process of the WT, down to the last computed smoothed WTC, simplifying the implementation. In addition, with a 'less accurate' transform, more energy associated with discriminating features is concentrated in earlier computed WTC. The 'decreased accuracy' of the LWT, thus may be exploited by stopping the wavelet transform operation after only those WTC necessary for classification have been generated.

The wavelet transform chosen for this work (the lifting version of the LWT) involves only the use of multiplier values of two and four (besides the Haar wavelet transform, all other wavelet transforms include multiplication by floating point values). The advantage of such an integer-based transform is that the input, intermediate, and WTC all are integer valued. Integer operations are faster and less costly to process than float values. For LWT integer calculations involving multiplies by two and four that do not cause overflow, there is no round off or truncation. To eliminate all float calculations in this work, the integer version of transform is not normalized, that is each sub-band is not scaled by $1/\sqrt{2}$. The purpose of the normalization constant is to conserve energy so that the squared energy of the original time domain data and the WTC are equaled (good for comparing scalograms but not useful for the implementation). A side effect of omitting the normalization is that the last computed coefficient is a scaled version, not the actual mean. Reconstructability is still preserved in the case of the inverse transform by omitting the $\sqrt{2}$ multiplier factor. The scale of the mean or any other WTC itself is not important, only their ability to discriminate between categories of events. There do exist methods for preserving the correct scale in the integer version of the transform (Calderbank, Daubechies, Sweldens, & Yeo, 1998, p. 25), but they are not necessary because the same transform scales WTC for all event categories by the same amount preserving their distributions and relative separability.

Advantages of the Integer-Based Lifting Line Wavelet

Implementing a wavelet transform in a processing-limited device, and maintaining time resolution for the analysis of IEGMs, are important design objectives. The LWT implemented in this work accepts discrete-time integer-valued data and generates integer-valued WTC. The property of perfect reconstruction still holds for the integer version of the LWT, thus the transform is lossless up to the point of ranking and pruning the WTC for reference definition. Reconstruction is not within the scope of this work and will not be discussed further. Due to properties given at §Properties of the Line Wavelet Transform, the comparison of the three discrete wavelet transforms (Haar, Line, and Daubechies 4) analytically in §Selecting the Best Basis, and the discussion in §Errors in Event Detection and Peak Alignment, the LWT was selected as the preferred basis for this work.

Prior literature on wavelet decomposition of the IEGM refers only to the Daubechies orthogonal transforms, and usually only the Haar transform (Murray, 1993; Batista, 1995; Zaffram, 1996; Anant, 1997; McClure, 1997; Azzam, 1998). Neither does there appear in this literature discussions about the advantages of the line wavelet over other wavelet bases, the advantages of biorthogonal transforms in a processing limited device, discarding the sub-band normalization factor, using integer values in transform, nor implementing the lifting version of the transform.

The predominant choice of wavelet basis in prior works, the Haar wavelet, has several nice properties. It is easy to understand and compact to implement. It is the prototypical wavelet providing the major features of all other WT from the simplest possible basis. However, the Haar transform has several shortcomings. Recall that, in the Haar transform, each odd value in the data is predicted by the even value immediately preceding it. Therefore, if a step change occurs in the IEGM between an odd sample and the even sample immediately following it, the time domain feature does not appear in the WTC until the next sub-band, at which point the time resolution has expanded by two. In other words, the Haar transform poorly resolves details depending on the parity of the sample. This presents an unacceptable deficiency since the upstroke of a depolarization event has a 50% chance of being located in the WTC of one sub-band or the WTC of another with twice the uncertainty in time. (Note: All other wavelet bases predict the odd sample with at least one sample preceding and following it, and do not have this parity drawback.) Additionally, the nominal Haar transform normalizes each computed coefficient by $1/\sqrt{2}$, which requires floating point or at least fixed-point computation. When normalization is applied, values in successive sub-bands are cumulatively re-scaled by factors of $1/\sqrt{2}$, $\frac{1}{2}$, $1/(2\sqrt{2})$, ..., causing a corresponding shrinking of feature class differences in those sub-bands to below the computational resolution limit. This could cause the false rejection of discriminating features in lower sub-bands. For reasons given in this section and not noted by others, the normalization constant is omitted from the LWT in this work.

Finally, all finite sample transforms must have a window boundary method and a prediction or assumption about what the signal behavior just beyond the window. Nominally, the Haar wavelet uses flat extension of the edge sample, which generates boundary discontinuities. The IEGM analysis-oriented works cited address none of these shortcomings of the Haar. This disclosure proposes solutions to those deficiencies.

When sources so far cited have not employed the Haar, those solutions used other Daubechies wavelets, always fourth or higher order. These bases require floating point computations for each filter coefficient above the requirement of the normalization constant. The higher order wavelets also have poorer time resolution proportional to their increased filter length. The longer filter length of these higher order wavelet bases were in fact developed for image processing where the data is sectioned into blocks the same size as the filter to achieve a processing time reduction. These methods are essentially smoothing or compression tools for quantities of data several orders of magnitude greater than the size of the data window used in this work. However, none of these drawbacks and benefits is addressed in sources whose topic is the analysis of IEGMs.

Figure 29:
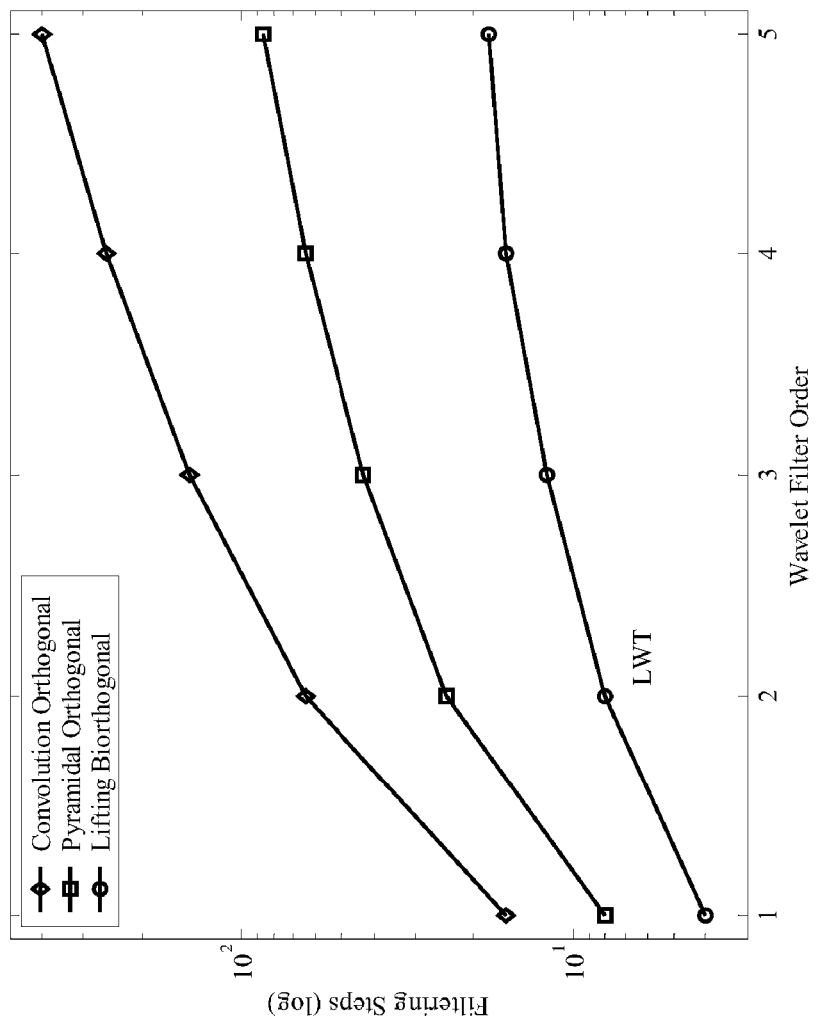
FIG. 29 shows three different methods to compute the wavelet transform of one IEGM event, the number of multiply add operations varies by wavelet filter order.

In addition to these differences between wavelet families, there are three main processing methods for decomposition. These are convolution, pyramidal, and lifting, which are $O(n^2)$, $O(n \log_2 n)$, and $O(n)$ in computational complexity, respectively. FIG. 29 shows the three processing methods and the corresponding expansion of filtering steps as wavelet order increases. The values are a minimal number of steps to perform the particular transform, as determined by the number of filter coefficients defined for that wavelet order.

However, the WT in this work is only over a short segment (32 samples), even at order=2, the figure shows an order of magnitude difference between the pyramidal orthogonal method (24 filter steps) and the LWT (biorthogonal method 8 filter steps). The Haar WT is order=1, and the Daubechies 4 WT is a fourth order transform. The relative performance of the LWT is indicated in the figure. Not included in the values is the additional overhead that would be required for floating point computation (in the orthogonal cases, and most biorthogonal cases) over integer only computations (biorthogonal order=1, or 2 only with omission of the normalization constant). Implementing the wavelet transform using a non-lifting method or a higher order transform would present an unacceptable service life cost.

Even with the benefits of the LWT discussed so far, Table 6 shows that the estimated cost of operating the LWT in an implanted device for every IEGM depolarization event for the lifetime of the device.

The actual count of operations (move, increment, compare, add/subtract, shift) to execute the LWT on a 32 sample time window over all sub-bands is 2,222 instructions. On the implanted device using a custom microprocessor operating at 475 kHz, would reduce device lifetime by 3.14 months. The DSP, on the other hand, shows an order of magnitude improvement in battery depletion for the LWT because the x12 code efficiency and better power-off capability.

The Boundary Handling Method

In addition, a novel method of boundary handling is implemented that mitigates the introduction of artifacts into the coefficients, using problem domain knowledge of the IEGM. The LWT uses flat ('Haar') extension and linear interpolation on the left and right boundaries. This work has addressed the drawbacks of other methods discussed here, and proposes a novel solution for these design objectives in the form of the integer valued lifting version of the line wavelet transform.

The Customized Classifier

Historical recordings of IEGMs are disjoint from those seen in actual implanted devices, because they do not limit the variation in future morphologies. With a library of recordings, a classification system could be developed that would perform with high accuracy on the library. However, that particular classification system would be accurate on unseen true physiologic input only to the extent that the library contained data representative of all IEGM waveforms the implant might ever see. Implantation into a patient produces new data because of: (1) the individual patient anatomy and condition, (2) the precision of lead placement on the inside surface of the heart, and (3) the time varying properties of the lead-to-living-tissue interface. Generally, such a library is recorded using a consistent input filter function. Such a 'universal' classifier trained on this signal library would still be limited to implementations that matched the input stage filtering of the library.

A classifier that is defined online, however, need only generate reference definitions based on the IEGM unique to a particular patient, filtered through a device input stage, which is unique due to component design tolerances. Therefore, the in-situ customizable classifier can be expected to generalize better than one designed for a library. Even the online method carries a caveat, that is, a very good feature generator would create independent features. When independence of features is difficult to determine (let alone achieve), orthogonal features will have to suffice. For the purpose of this disclosure, these features will be biorthogonal (orthogonal between sub-bands) and non-redundant. Ultimately, the question is: 'Can the wavelet transform generate features that are separable, that is, that generate a discriminating function that divides two classes (normal and abnormal) of IEGM events. Chapter 5 will answer this efficacy question by presenting the results of decomposing IEGMs with the LWT and evaluating the features with the ROC.

Instantiating the Classifier

This section presents the synthesis of the definition phase. Nearby reference events from beat to beat should be consistent (low intra-class variance). The measurable outcome criterion that will demonstrate successful discrimination of classes is ≧95% accuracy with 95% confidence. Traditional hypothesis testing can reject correct models simply because the power of the test is low due to small sample size (Jensen 2002). Classifiers based on only a few reference events have been demonstrated, achieving ≧95% accuracy for classifying IEGMs, for as little as 10 s (Strauss, Jung, & Rieder, 2000, p. 545) or just 10 events (De Voir, Schomburg, Ramachandran, & Lessard, 2002, pp. 176-177). Consider the likelihood that the next depolarization event will be just like the previous one. This is true in most rhythms and arrhythmias of interest. In the arrhythmia types where this does not hold, the rate is so high that effective contractions are not occurring even if there was a mechanical event for each depolarization event. At such high rates, the physician prefers that defibrillation therapy be provided regardless of the morphology of the event. Still higher rate periodic waveforms obscure the ability of the device to distinguish depolarizations from electromagnetic interference, and the safe mode involves pacing until the 'noise' subsides. Therefore, the implementation will follow the simple rule of definition during sustained periods of normal heart rate variance, with the expectation they will consistent. For sustained periods of elevated heart rate with low variance in interbeat times, another training period should be initiated for a reference definition of a new class. The implanted device can also be purposely configured to induce a benign rhythm of abnormally conducted events, during which yet another reference definition should be generated.

Feature Selection for the Purpose of Classification

Information loss occurs through sensors because they are communication channels of limited capacity. Any additional intentional loss should be chosen for some benefit. The real depolarization event is four-dimensional and cannot be observed in the entirety. The IEGM available for evaluation by a human or machine intelligence has limited spatial and time resolution. It is critical that the evaluated signal contains features that allow differentiation of pathways through the tissue to separate events into categories. Humans do well at classifying IEGMs with visual inspection, while the device has the possibility of classification using features that humans cannot perceive. Though classification performed by these two systems can be compared, it is performed on different representations that should correspond to the same original event. Thus, the human expert and wavelet-based methods of classification can only serve as abstractions for each other. Quantifying the accuracy of human expert IEGM classification is not within the scope of this work, though human expertise will establish the benchmark for evaluating the performance of a WT based classifier.

For minimizing processing in the implant, the best transform would be the one that provides the benefit of concentrating the time samples of the depolarization event into the least number of values. Further loss of information results from compression methods, such as best basis or PCA. For example, PCA (§The Basis of Morphological Differences), is an $O(n^3)$ transform of the data that maximizes the variance, extracting pre-ranked features without regard to class membership (Fradkin & Madigan, 2003, p. 518). Nevertheless, if the resulting low magnitude features are discarded, there is no guarantee that remaining ones are any more capable of differentiating event types. Compression methods are also optimized for signal content that is stationary. Because it is non-stationary content that discriminates between events, at best there can only be a tradeoff between reducing processing load and maintaining classifier accuracy. Although compression oriented methods were applied to IEGM analysis in other works (previously cited), the drawbacks of those methods (highlighted in this section) were not presented in those sources. While this represents a general problem in the use of WTC for classifying other signals, the scope here will be limited to the IEGM and the novel contributions of this work.

On the other hand, the general goal of classifier oriented feature generation is to find a transformation of the original signal that achieves the best possible class separation. Since, PCA only de-correlates data when it is non-Gaussian, an orthogonal WT can do no worse. In fact, the LWT is an O(n) biorthogonal transform that approximates the PCA (§Dimension Reduction Property). Regardless, it is a requirement of this work to demonstrate the feasibility of the WT as a generator of features capable of class separation of IEGM events.

The Wavelet Transform Dimension Reduction Method

Having opted not to use a compression method, the dimension reduction task is now de-coupled from the transform. Therefore, the ROC is chosen to reduce the feature set because it is a distribution-free dichotomizer, and feature selection can now be directly coupled to class separability. Each point on the ROC curve corresponds to a confusion matrix (a contingency table for classifier accuracy) that results from varying a class threshold across the data values of a single feature. The goal function of the ROC is to reveal the best threshold for discrimination as indicated by the contingency matrix with the least off-diagonal sum (error), corresponding to minimum $d_v$ for that curve.

Features will be ranked relative to each other according to their discrimination, that is, the area between the ROC curve and x=[0 . . . 1], or AUC. Features that have high intra-class variance, and low between-class separation, will have lower AUCs. Below some acceptance criterion, features yielding small AUCs will be discarded. The benefit for information loss here is: (1) features are selected that discriminate better instead of features that are merely larger in magnitude, and (2) the processing load on the device is still reduced, because the number of WTC has been reduced.

[Practically speaking, the ROC is used for one-at-a-time feature ranking and priming the kernel discriminant with most meaningful coefficients. Threshold based classification using one feature at a time was proved to be highly accurate (>95%). However, if it desired to use multiple features simultaneously for classification, the modified Kernel Discriminant (KD) is feasible in the implant for the following reason. The modification of the KD assumes independence of the features, which is justified in this work. Independence allows reduction of the Mahalanobis matrix to the main diagonal values only. Since the WT generates independent coefficients, off diagonal cross-variances can be ignored. Inverting this diagonal matrix is the much easier operation of inverting the few non-zero main diagonal elements only. The resulting hyperplane discriminant in n-dimensional feature space is analogous to the discrimination line (threshold) in 1-dimensional ROC space.]

Benefits of an Implantable Wavelet-Based Classifier

When a morphology-based classifier can be implemented in an implanted device, the expertise of the physician is extended there also. Fewer false alarms for pseudo-arrhythmias result in reduced battery depletion and extend the lifetime of the device. Correct identification of normal versus abnormal events, also categorizes effectively versus ineffectively perfusing heartbeats (Fogoros, 1999, p. 244). Therefore, correct identification also reduces pacemaker syndrome by reducing the side effect of unnecessary pacing (Hayes, Lloyd, & Friedman, 2000, p. 56). Presently such a solution does not exist (Stroobandt, 2002, p. 443). The only implantable 'morphological' classifier commercially available is still timing-based (QRS width metric) with an accuracy of 67% (Duru, Schönbeck, Lüscher, & Candinas, 1999, p. 1046; Gillberg and Koyrakh, 2002). Though discrimination as a basis for wavelet-based feature generation and selection for the classification of IEGM events in an implantable device is presented in this work, it does not appear in the cited sources.

Additional benefits are available because of the reduced WTC feature set. WTC selected by classifier performance can be stored for later retrieval, and still provide a compression benefit. The implanted device has limited memory to store IEGMs for follow-up retrieval and off-line analysis, therefore, IEGMs are often compressed to such a degree that reconstruction yields only iconic waveforms. Physicians have already accepted this abstracted waveform introduced into the display at the correct time of the event. WTC features selected based on classification can be used to reconstruct waveforms enhanced with details specific to that event class. Thus, the event presented to the human expert still may be iconic, but contains class discriminating information at a small cost in storage and communication time.

Because only selected WTC are being stored and transmitted, communications time is reduced for off-loading stored IEGM data in home or clinical monitoring application. This benefit can be taken as: (1) a reduced energy usage from the battery, or (2) reduced transmit time, allowing the communication of more data from other services in the implant. Demonstrating the benefits of enhanced off-line reconstruction and reduced communications time are outside the scope of this work.

Comparing Wavelet Transform Coefficients

Figure 30:
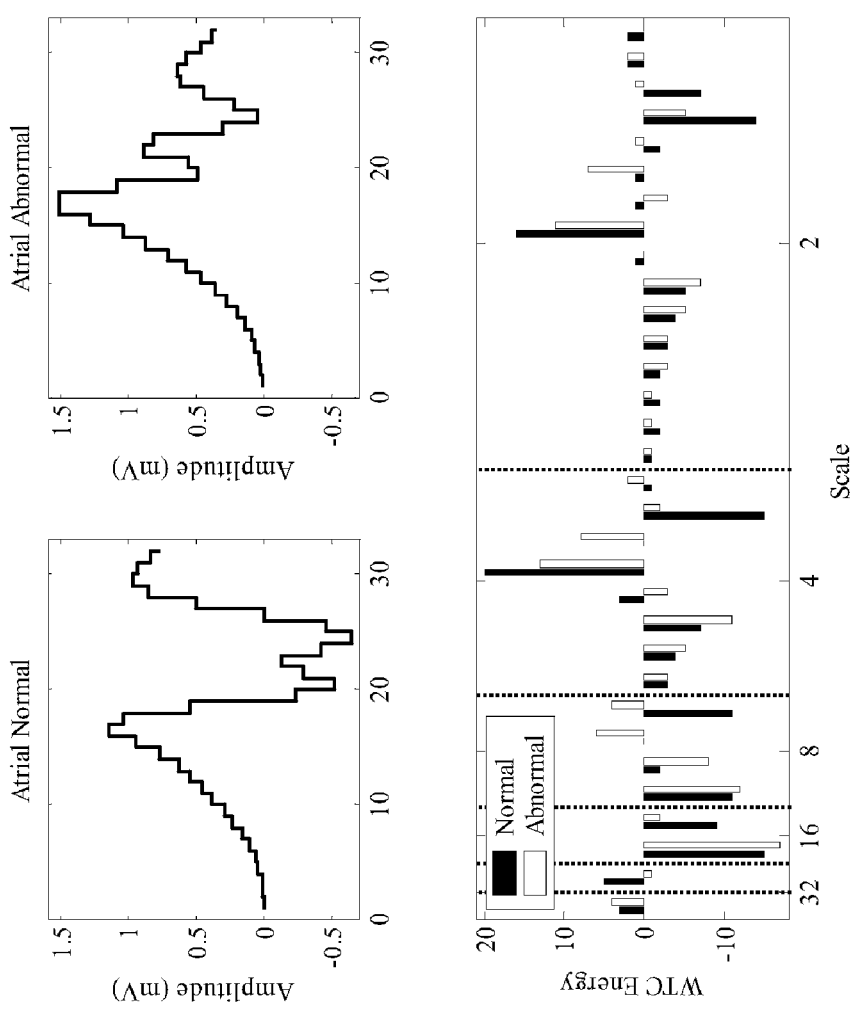
FIG. 30 shows the wavelet transforms coefficients of two IEGM events.

FIG. 30 shows the previous two IEGM events from FIG. 25 in the upper subplots, and a side-by-side comparison of WTC energy values resulting from their decomposition, where normal is a filled bar ■, and abnormal is a bar with no filling □ (lower subplot). The wavelet scalogram surface from FIG. 25 is displayed edge-on in FIG. 30, so the energy values can be seen as bars extending up and down from zero. So all the sub-bands can be seen, they are rearranged side by side across the figure with each scale separated by a vertical dashed line ¦. Time resolution improves to the right along the x-axis (as explained in §Time Localization Property of the Wavelet Transform). The decomposition generates detail WTC first on the right (Scale=2) and smooth WTC last on the left (Scale=32). The WTC that are discriminating features are those whose values diverge for normal (■) and abnormal (□) event classes.

Temporal correlation causes smaller differences between adjacent time samples to generate, in general, smaller initial WTC values in the first sub-band (Scale=2). At Scale=4, the wavelet spans a larger non-correlating regions of the event, resulting in increased WTC values. The pair of values (■ and □) to the left of ¦ at Scale=32 correspond to the means of the IEGM events in the upper subplots.

In works cited, the method of reducing computational load is to abort WTC generation beyond a sub-band when further WT will produce no additional coefficients above some magnitude threshold. For example, execution of the WT could be stopped before calculating all coefficients to the left of Scale=16. Again, this is a compression-oriented method.

Here, it is proposed that all WTC initially be computed for reference definition and stored at a cost of one full WT. After ROC analysis, a sub-band computation limit indicating further WT will produce no additional coefficients having discrimination (AUC) above an acceptance criterion is stored. In classification phase, the WT is truncated beyond the sub-band limit, saving processing. This method of conditional processing of WT sub-bands based on feature discrimination of IEGM event classes is unique, and was not discussed in works found.

Chapter 5

Assessment

This chapter is organized as follows. First, some background concepts related to the assessment are explained. Second, the basis of the assessment design is described. Lastly, the assessment results are presented.

Definition of Discriminator

It is required in this work that IEGM events be correctly discriminated between categories with 95% accuracy. The discriminator is an input-output module that accepts a limited number of definitions (exemplars) corresponding to output categories during a definition phase, giving it the capability to dichotomize future unseen data. Its discriminatory power are diminished by feature distribution overlap, which is inversely related to the separation of the class means and directly related to their variances. The discriminator ambiguity between class distributions is maximal where the probabilistic value of two classes is equal.

The wavelet based feature extractor described in this disclosure accepts time domain inputs limited in duration and amplitude and provides input variables for an IEGM event discriminator system (DeVoir and Schomburg, 2004), though it is not within the scope of this work to describe that system. Instead, wavelet transform coefficients (WTC) selected by a classifier-free method, the ROC AUC, will be evaluated for their discrimination.

Feature Reduction

It is a requirement for the disclosed solution that features be reduced in number prior to presentation to the discriminator. Feature reduction (through selection) of many WTC to one or a few is necessary for several reasons.

(1) The processing load to the implanted device must be limited (§Advantages of the Integer-Based Lifting Line Wavelet).
(2) The number of feature subsets is a combinatorial function of the feature count (§The Receiver Operating Characteristic Curve).
(3) The number of observations must exceed the number of free parameters, where a rule of thumb from the general linear model (§Dimension Reduction Property) is 10 observations for every one parameter (Costello & Osborne, 2005, p. 7). (Note: This 10:1 ratio can be accomplished through either increased observations, or the reduction of features.)
(4) Outside of this work, exceeding a structurally dependent limit on feature count makes statistical classifier design less tractable, incorporates more noise, and overfits the model to the reference data (Schürmann, 1996, p. 255).

Single Feature Evaluation

To meet the requirement of feature reduction one may ask, 'Why not try the minimum feature count?' Therefore, the single best WTC will be selected and its performance as measured by accuracy of discrimination will then be assessed. When the LWT is performed, all resulting WTC are considered candidates for discrimination. For any given WTC, the ROC curve is a characterization of a simple threshold based one-dimensional classifier. Rightly or wrongly, feature data at or below the threshold will be categorized as 'negative,' or a normal event. Likewise, feature data above the threshold will be categorized as 'positive,' or one of the counter-events, for example, T-wave or abnormal depolarization. The area under the ROC curve AUC is generated as described in §The Receiver Operating Characteristic Curve. If AUC<0.5, it means that the normal event corresponds to feature values above the threshold, and vice versa for the counter-event. In this case, the classes are exchanged on either side of the threshold, and the AUC is re-evaluated. The WTC are rank ordered according to decreasing AUC. The single feature discriminator serves as a performance benchmark for later work that would seek increased robustness at a potential cost of increased processing.

Assessment Design

Figure 31:
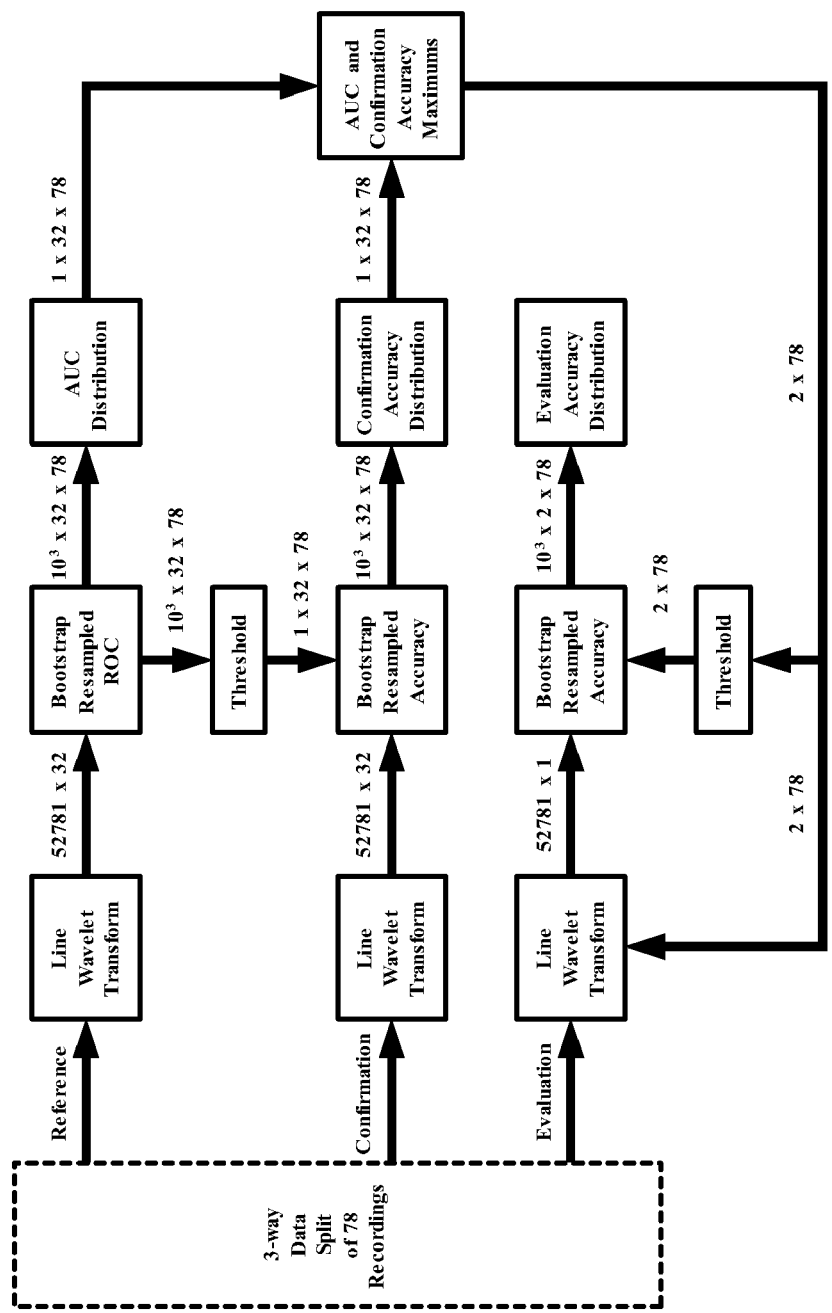
FIG. 31 shows the IEGM observations are transformed into wavelet coefficients and reduced to a single discriminating WTC using true class data.

The assessment design has the following overall structure, which can be followed in FIG. 31. From left to right in the figure, a single IEGM recording is divided into three non-overlapping time spans of equal length. The events found in each dataset are transformed by the LWT yielding some number of WTC. Inside the dashed box, the events will be bootstrapped (resampled with replacement), and the true class labels will be used to generate AUCs, thresholds, and accuracies. From top to bottom in the box, results generation for each of the three phases will be the following. In the reference phase (top), AUCs and thresholds will be bootstrapped for each of the 32 WTC. In the confirmation phase (middle), accuracies will be bootstrapped for each of the 32 WTC using thresholds found in the reference phase. At this point a decision rule selects the WTC with either the maximum reference AUC or the maximum confirmation accuracy. If there are two WTC with the same maximum, the earliest computed WTC is selected. In the evaluation phase (lower), the final accuracies will be bootstrapped for the single WTC selected by the rule.

FIG. 31 shows one experimental instance of a model for offline computation of preferred coefficients and thresholds. 78 was the number of patients in the study. 52781 was the number of events analyzed. If generalized by abstracting these specifics, this is a model for offline computation of meaningful coefficients and their thresholds, such as, at the HMS.

Bias Correction and Confidence Interval Estimation

Bootstrap resampling uses a limited number of observations to make estimates of population parameters (§Assessment Design) and thus may miss the true value of a parameter by some offset error (bias). Because the true parameter is unknown, estimates are accompanied by an expression of the limited certainty that the true value lies within some range (confidence interval). The bias of an estimator is defined as: $b = \hat{\theta}_o - \theta$, where $\hat{\theta}_o$ is an estimator, for example, a sample mean, and $\theta$ is the parameter, such as, the population mean. Because $\theta$ is not available, in bootstrap statistics $\hat{\theta}_o$ is used as its surrogate. The estimator of the bias in the surrogate $\hat{\theta}_o$ is defined similarly as: $\hat{b} = \hat{\theta}_B - \theta_o$, where $\hat{\theta}_B = \text{mean}(\hat{\theta}_i)$, and $\hat{\theta}_i$ is the set of i iterates of the bootstrap estimate (Efron & Tibshirani, 1994, pp. 124-126). The biased corrected bootstrap estimator becomes: $\hat{\theta}_o - \hat{b} = 2 \cdot \hat{\theta}_o - \hat{\theta}_B$. The acceptance criterion in this work is $0.95 \leq \text{accuracy} \leq 1.00$. Therefore, only a one-sided lower confidence limit (LCL) is required for performance evaluation. The LCL exact solution $p_L$ can be obtained by solving $$\sum_{k=0}^{N_d-1} \binom{N}{K} p_L^k (1-p_L)^{N-k} = 1 - \alpha,$$

for $p_L$ ("Confidence Intervals," 2005). Because N>>30, the LCL is computed as: $(\hat{\theta}_o - \hat{b}) - z_\alpha \cdot \text{std}(\hat{\theta}_i)$, where $z_\alpha$ is the critical value chosen for some $\alpha$, such as $\alpha = 0.05$. This later calculation of LCL assumes that the mean of the estimator has a normal distribution.

Statistical Evaluation of the Discriminator

The ranking of areas under the receiver operating characteristic curves can only rank the relative statistical powers ($\beta$) of the features, it cannot quantify them (Elkan 2003). Therefore, the accuracy (tp+tn)/(fn+tp+tn+fp) of the best threshold (as defined in §The Receiver Operating Characteristic Curve) will be evaluated on unseen data by bootstrap to generate a quantifiable outcome. In contrast to the stated 95% acceptance criterion, state of the art devices discriminate supraventricular tachycardia from ventricular tachycardia with ~50% accuracy according to a recent study of rate-based methods for single-chamber devices. A sufficient number of records to evaluate the method according to this disclosure against the stated acceptance criterion with a margin of error of E=0.05 for repeatability are ≧73 (Elkan, 2001, p. 429). The number of IEGM records in this work is 78.

Effective Independence of Data Splits

This section discusses the effective temporal independence of event classifications of intra-patient depolarization events across data splits (§Assessment Design) from two points of view. One may ask, 'How much time must elapse so that discriminator accuracy is not affected by temporal correlation?' The first way to answer this is to consider that the prediction of onset or continuation of any instance of a particular rhythm has not been demonstrated in the literature. Rather, the communication between working myocardial cells is a stochastic electrochemical process (Spach & Heidlage, 1995) through a microscopically inhomogeneous medium. The rapid dissemination of the stimulus via the conduction system and coupling provides the appearance of a macroscopically homogeneous wavefront and stability in the normal rhythm (Bieberle, Hensel, & Schaldach, 2001). In general, the physical structure (substrate) and the position of arrhythmia generators are slowly changing over months or years, and can be considered spatially fixed. However, beat-to-beat variation in the action potential is a genuine random process yielding a net unpredictability of any particular arrhythmia trigger (Zaniboni, Pollard, Yang, & Spitzer, 2000). Such a trigger event occurring spontaneously at just the right time for the existing physical relationship to vulnerable tissue triggers an arrhythmia (Kraetschmer, 2002, pp. 22-25). Thus, to paraphrase Heisenberg, normal depolarization events have a "tendency to occur," while ectopic depolarization events have a "probability of occurring" (Heisenberg, 1958, p. 70). This underlying stochastic variation between IEGM events is no less for events that occur back to back, than those that occur one month apart (Stafford et al., 1997, p. 412).

Although correlation is not causation, a second way to establish temporal independence is establish an time span by which the IEGM data, and therefore the processes from which features are generated, can be considered temporally uncorrelated (refer to §The Customized Classifier). The autocovariance of white noise is the variance of the process at lag=0, and zero everywhere else (Hayes, 1996, p. 93). The limited sample white noise autocovariance has asymptote $-1/N \pm 2/\sqrt{N}$ with 95% confidence (Ifeachor & Jervis, 2002, p. 255). Therefore, the time offset producing effective temporal independence for the IEGM will be defined as the lag producing >18 out of 20 autocovariance values within that confidence interval. The maximum time required for the autocovariance to diminish to the white noise level for any patient recording in this study was 31 s. All data splits are an order of magnitude longer than this maximum time. Therefore, the assessment design in this work provides an adequate separation between reference, confirmation, and evaluation datasets in either case. The autocovariance provides a quantifiable duration of the possible corruption of the accuracy by temporal correlation.

Data Description

A proprietary collection of pre-annotated IEGMs is the standard to which the classification accuracy is being compared. The event annotations accompanying these recordings are defined as 'true' or 'actual' for the scope of this work. With respect to the receiver operating characteristic curve, such a classifier would have 100% true positives and no false positives. In the latter case, it is apparent that the rate-based classifier has no discriminatory ability for atrial rates equal to ventricular rates (1:1 AV conduction SVT cannot be distinguished from 1:1 VA conduction VT). Therefore the rate based classifier is as least as poor as flipping a fair coin when morphology would be required to correctly discriminate rhythms. Arguably its accuracy might be as low as zero in the case of a poorly adjusted IPG that detected far-field or T-wave as events and classified the presence of an arrhythmia on the basis of rate alone.

Proprietary IEGMs from 78 anonymized patient recordings were made during IPG implantation in Alessandria, Italy in 2004. These recordings are the most challenging kind because the leads are not mechanically stable, subject to motion artifact, accidental disconnection, electromagnetic interference, and numerous device adjustments over span of the recording. Permanently implanted leads would provide a much more 'clean' signal morphology. Although the recordings average twice as long, the record lengths are truncated at 39 minutes due to a Matlab memory limitation. Sampling frequency was 512 Hz, and all data was band pass filtered between 2 Hz and 189 Hz (according to §Pre-processing of the IEGM). Amplitude resolution was 10 bits within a full range of ±32 mV. Originally recorded amplitudes are used without normalization to the full ADC range. The IEGM signal is windowed 32 samples long (62.5 ms at 512 Hz) centered on the peak of the event as shown in the upper subplots of FIG. 30.

Table 7 gives an overview of the IEGM recordings. The first column shows which event pairs are being discriminated for the data in that row, for example, the second row of data applies to the recordings for spontaneous atrial events versus paced evoked response events. The second column shows the total duration of recording time and number of patients. In the example, 40782 s of recordings are spread over 19 patient recordings. The third column contains the total numbers of events for each class. The ratio between classes in general does not approach 1:1 because of natural processes, device settings, and the non-ideal conditions just mentioned. Continuing the example, there were 16784 spontaneous atrial events to 6231 paced evoked response events. In the last column, the maximum autocovariance for any recording in that class is listed. Although this value is measured for all recordings, only the maximum time is reported here as a worst case for the required time separation between data splits. Finishing the example row of data, the worst-case time until the autocovariance diminishes to the noise level is 31 s. As noted in §Effective Independence of Data Splits, this is the worst case for the entire cohort.

Assessment Methodology

Table 8 provides additional details of the assessment methodology process and flow of information through and between phases of the assessment design presented in FIG. 4. The Matlab prototype models part of a larger system that pre-processes the IEGM to make a buffer of samples available to the LWT and the discriminator. In essence, the signal is prepared for extraction of the windowed depolarization events (steps 1 through 5) by band pass (includes anti-aliasing) filtering and quantization. (Note: Here, the band pass is for morphological discrimination as opposed to event detection in §Pre-processing of the IEGM). The events are then transformed by the LWT and split for the three phases of assessment (step 6). Mean and 95% lower confidence limits are calculated for all parameters (steps 7 and 8). The WTC is chosen (step 9). Evaluation accuracy is calculated (step 10). Lastly, a calculation is performed on the energy saved by halting the transform in the evaluation phase after the chosen WTC has been generated (step 11).

TABLE 8

The assessment methodology.

1. Band pass filter IEGM 2 Hz to 189 Hz.
2. Quantize amplitude data to 10 bits.
3. Calculate time to autocovariance diminished to noise level.
4. Identify event time stamps.
5. Identify event peak time stamps.
6. LWT 32 samples centered on peak time stamps.
7. Calculate reference ROC AUC and thresholds for 32 WTC on first 1/3 IEGM data.
    a. Bootstrap resample 1000 times each parameter mean and 95% lower confidence level.
8. Calculate confirmation Accuracies for 32 WTC on second 1/3 IEGM data.
    a. Bootstrap resample 1000 times each parameter mean and 95% lower confidence level.
9. Select the highest numbered WTC equal to max(confirmation accuracy).
10. Calculate evaluation accuracies for best single WTC on last 1/3 IEGM data.
    a. Bootstrap resample 1000 times each parameter mean and 95% lower confidence level.
11. Analyze energy savings from resulting sub-band distribution of evaluation accuracies.

WT Energy Consumption by Sub-Band

Figure 32:
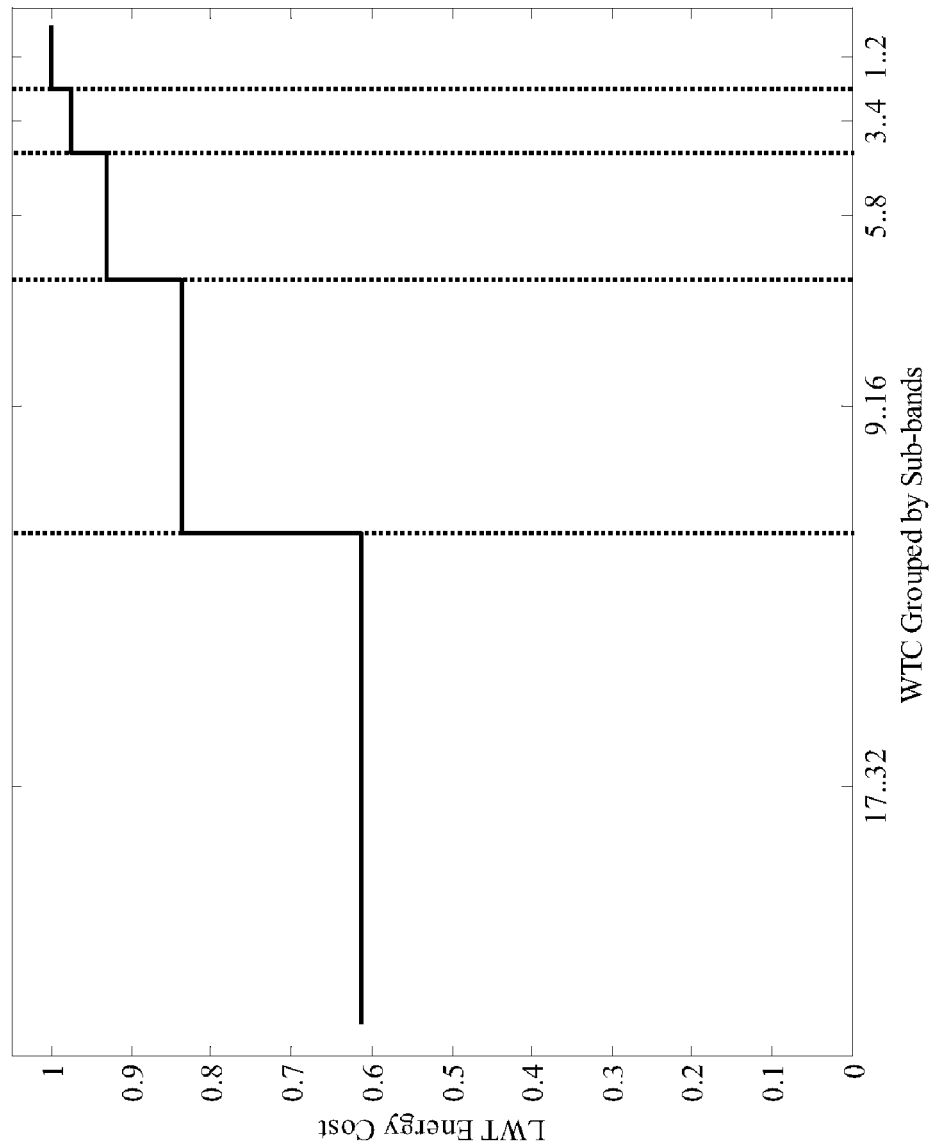
FIG. 32 shows the LWT energy costs can be reduced by not processing all the sub bands.

Step 11 in Table 8 uses the values at plateaus of the energy accumulated by sub-bands shown in FIG. 32.

As the LWT progresses through the sub-bands, the proportion of energy used by the LWT accumulates toward unity. The distribution WTC in the sub-bands for evaluation accuracy reveals the energy savings possible for the discriminator. This energy cost plot can also predict the relative service life reduction for performing the LWT within an implanted device on data sampled at 512 Hz, 256 Hz, and 128 Hz. These sampling rates correspond to starting the LWT on the sub-bands $17 \ldots 32$, $9 \ldots 16$ and $5 \ldots 8$, respectively. Though, as will be seen, there is morphological information up to 175 Hz, there is also successfully discriminating information at lower frequencies. Such a sampling rate reduction would allow additional service life savings, because proportionally 1/2 fewer samples require processing for each halving of the sampling rate. The upper attenuation corner of the pass band of Step 1 in Table 8 would be reduced proportionally to prevent aliasing.

Assessment Results

Figure 33:
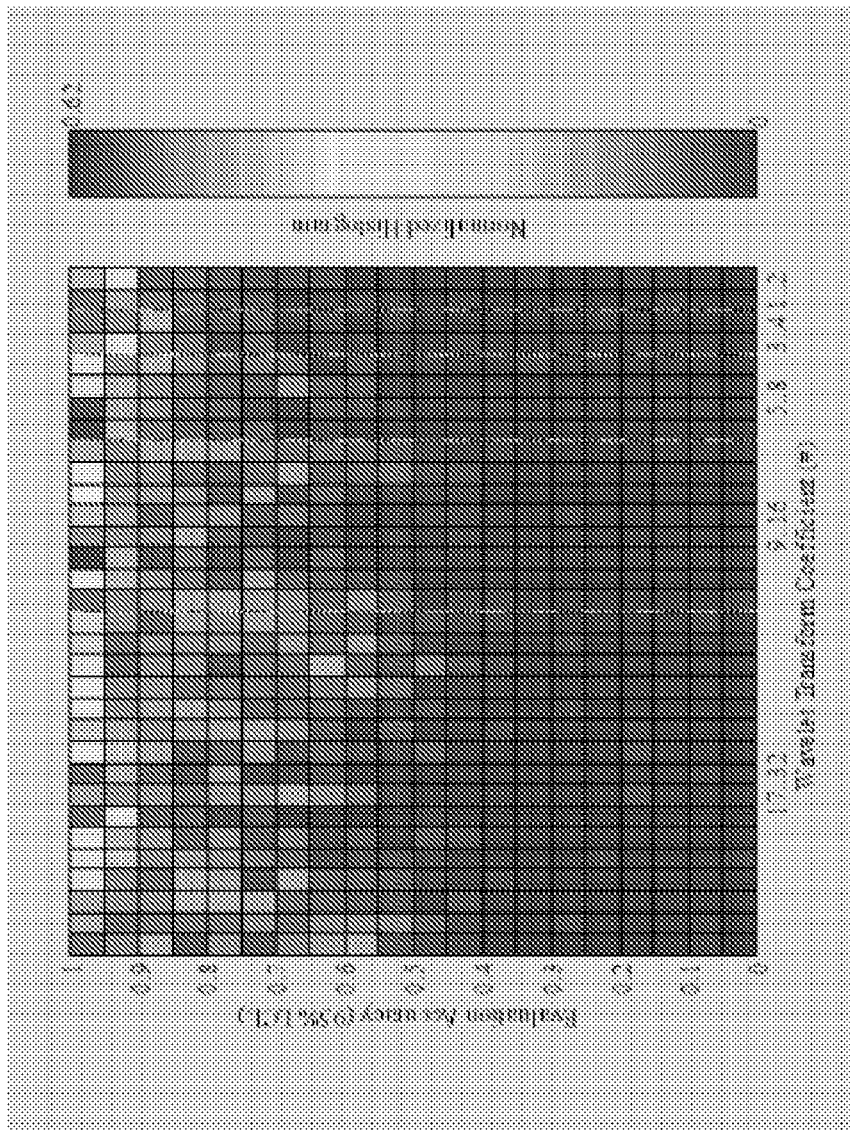
FIG. 33 shows the normalized evaluation accuracy means (95% LCL) organized by sub band shows concentration of accuracy within the acceptance criterion.
Figure 34:
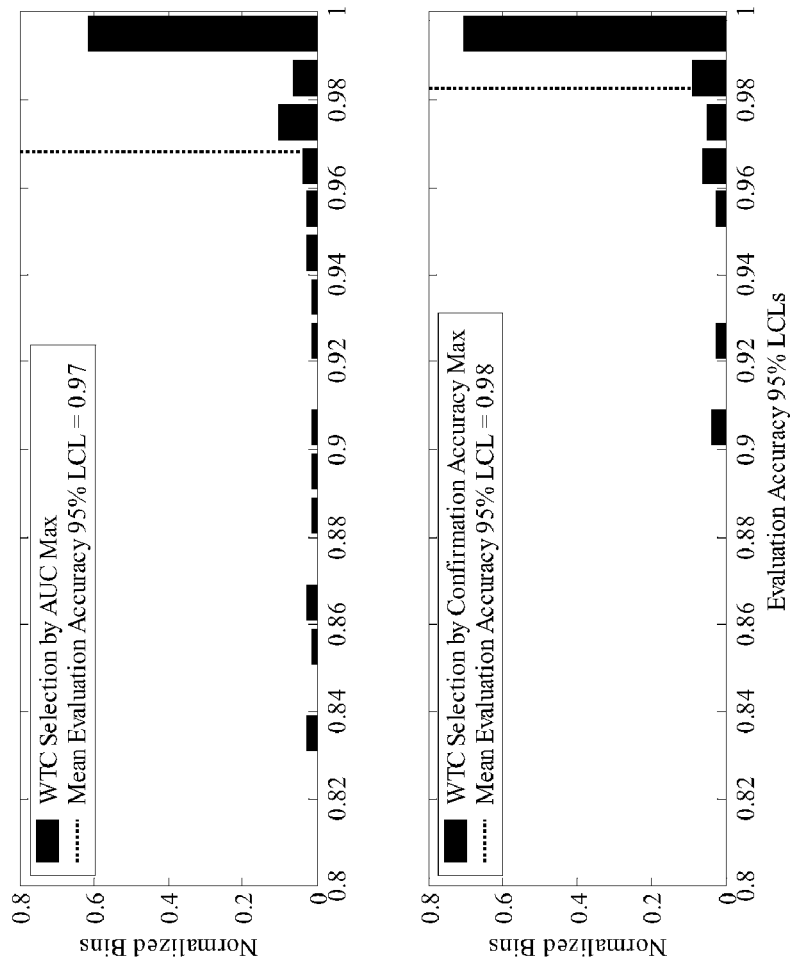
FIG. 34 shows the selection of most significant LWT coefficients by either AUC maximum or confirmation accuracy maximum resulted in mean evaluation accuracies $\geq 95\%$.
Figure 35:
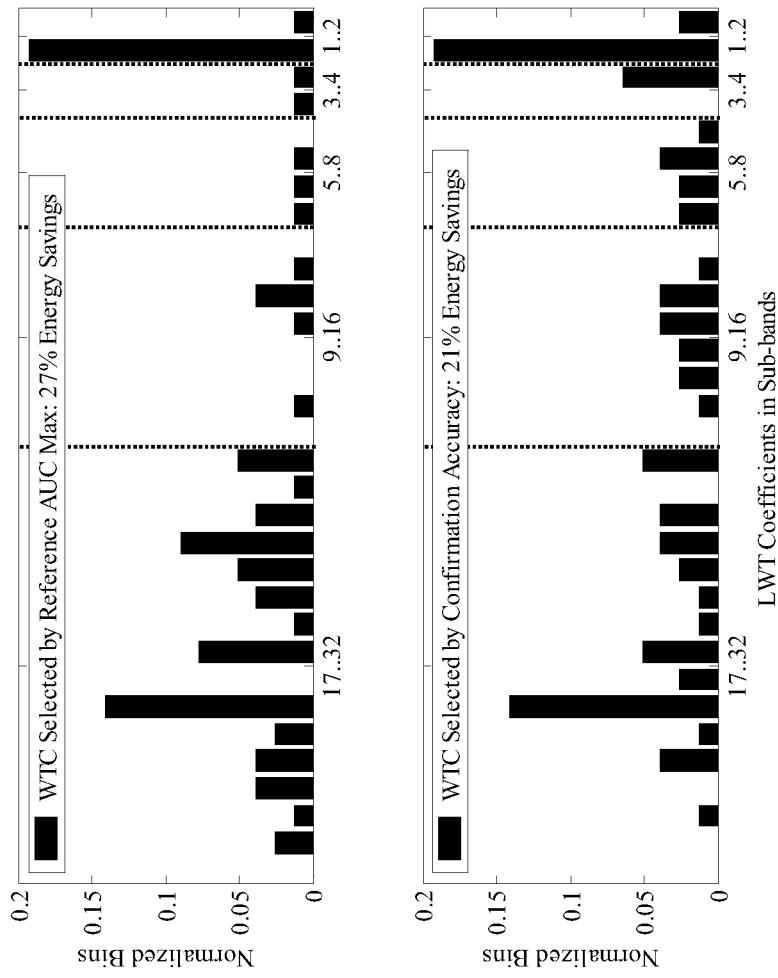
FIG. 35 shows the distribution of selected LWT coefficients by AUC and confirmation accuracy maximums resulted in energy savings of 27% and 21%.
Figure 36:
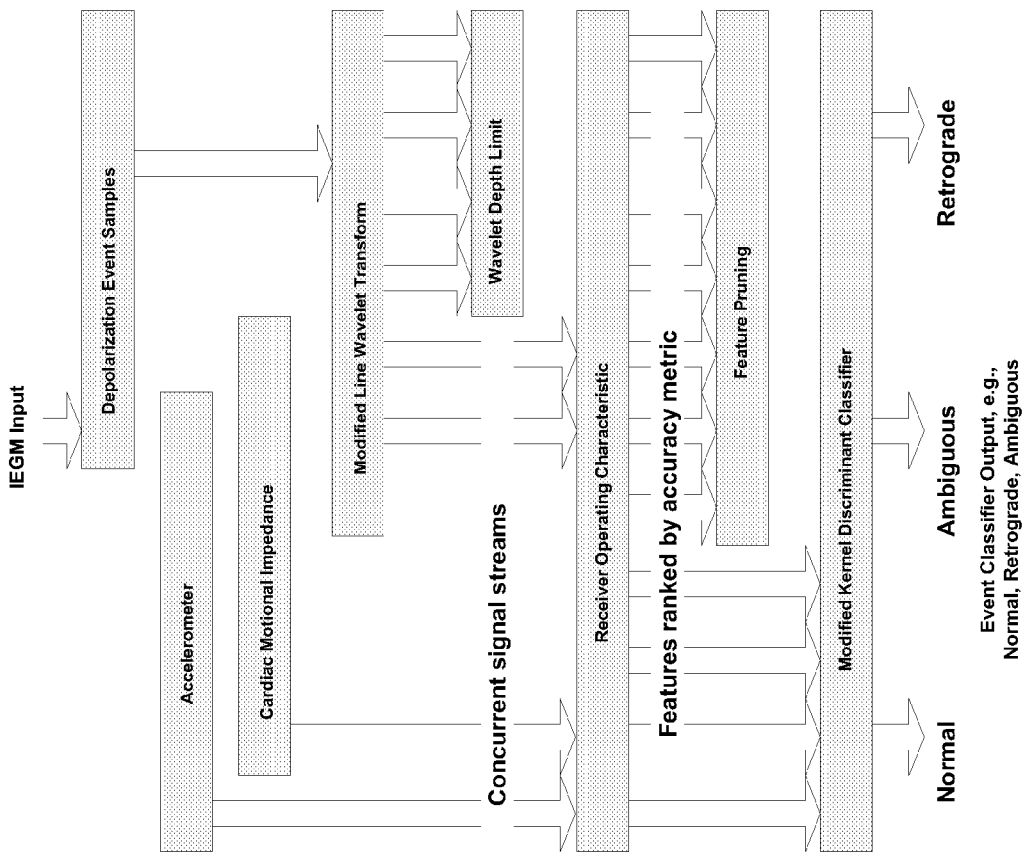
FIG. 36 shows an event processing diagram.

FIGS. 33-35 and Table 9 show the results of selecting the best WTC for event discrimination of evaluation data from one of two alternatives (§Assessment Design). The first figure shows the distribution of accuracy on evaluation data divided into WTC and pooling all recordings without regard to the selection rule. The second figure shows the accuracy distribution on evaluation data comparing the two decision rules pooling all recordings and all selected WTC. The third figure shows the distribution WTC selected by both decision rules divided into sub-bands in order of calcuation. Table 9 summarizes mean accuracies found on the evaluation data sorted by event discrimination task (category pair).

FIG. 33 is organized as follows. The gray-level plot in the figure is arranged left to right by WTC (grouped by sub-band) in order of their calculation. White lines indicate divisions of the sub-bands corresponding to the cumulative energy function shown in FIG. 32. From top to bottom are decreasing 95% lower confidence limits of accuracy means in divisions of 0.05. The gray-level in the plot provides an axis rising out of the page indicating the normalized bin count. In other words, a single column in the plot is an accuracy histogram for one WTC viewed from above. The gray-level on the right gives the scale of the normalized bin count.

To reveal the most contrast, the gray-level in the plot was scaled between zero and the maximum bin value (WTC #11, $0.95 \leq \text{accuracy} \leq 1.00$). All recordings were pooled for this figure, therefore for any particular column, the sum of all bin counts before normalization was 78. The top row of data ($0.95 \leq \text{accuracy} \leq 1.00$) shows the accuracy more diffuse in earlier than in later calculated sub-bands. Within sub-bands WTC corresponding to peaks or leading edges of events have higher accuracies. When the last computed sub-band is evaluated (WTC #1 and #2), event discrimination is comparing differences between mean energies of the events, not morphology.

FIG. 34 displays the evaluation accuracy for a WTC selected by either the reference AUC maximum (upper subplot) or the confirmation accuracy maximum (lower subplot). The figure is the marginal distribution of FIG. 33 over all WTC filtered by the decision rule. FIG. 34 is organized as follows. The x-axis for both subplots is the 95% LCL of mean evaluation accuracies for WTC selected by the rule. There are no accuracies generated by the rule <0.80 so the x-axis ends there to show detail. The y-axes are normalized histogram bins of accuracies. All 78 recordings are represented in both the upper and lower subplots. The 95% LCL of the mean of each accuracy distribution is indicated by the vertical bar | in the subplots. It can be seen that WTC selected by the AUC maximum will result in evaluation accuracies that meet the acceptance criterion at least 97% of the time with a 5% error on repeatability. With the AUC max rule, there is some skew in the distribution toward 0.80. In contrast, WTC selected by the confirmation accuracy maximum will result in evaluation accuracies that meet the acceptance criterion at least 98% of the time, where the tail of the distribution ends at 0.90. The threshold to discriminate events in either case is determined in the reference phase.

FIG. 35 displays the distribution of WTC selected by either the reference AUC maximum (upper subplot) or the confirmation accuracy maximum (lower subplot). The figure is the marginal distribution of FIG. 33 over all accuracies filtered by the decision rule. FIG. 35 is organized as follows. The x-axis for both subplots is the WTC selected by the rule separated into sub-bands by the vertical bar |. The y-axes are normalized histogram bin counts of the time a particular WTC was selected by the rule. All 78 recordings are represented in both the upper and lower subplots. The distributions the AUC max and confirmation accuracy max WTC selections show that the AUC max rule favors earlier computed WTC. This is confirmed by summing the scalar product of the energy consumption curve (FIG. 32) and the normalized bin count of each distribution.

The energy savings by stopping the LWT after the AUC max selected WTC has been generated is 27%. For the tighter accuracy distribution in the lower subplot of FIG. 6, the confirmation accuracy max rule shifts the selection WTC to those in later computed sub-bands. In the latter case, the energy savings is of early exit of the LWT is only 21%.

Lastly, Table 9 summarizes the evaluation accuracies for each event discrimination task pair resulting either from the AUC max or confirmation accuracy max selection WTC. The table is organized as follows. The first column shows which event types are being discriminated for the evaluation data in that row, for example, the last row of data applies to the recordings for ventricular 'normal' (antegrade) events versus ventricular 'abnormal' (retrograde) events. All other columns give the 95% LCL of the mean evaluation accuracy for a WTC in that sub-band chosen by the rule. In each cell, the upper value is the AUC max result, and the lower value is the confirmation accuracy max result. An entry of Not Used' designates that no WTC was chosen by the rule in that sub-band for that discrimination task. Some values are 1.00 due to rounding. Overall, the 95% LCL of the mean evaluation accuracy was $\geq 0.95$.

Chapter 7

Derivation and Elucidations of the Algorithm

In this chapter an intuitive derivation and elucidations of the algorithm to perform the line wavelet transform (LWT). This solution is designed to exist within an implantable pacemaker or defibrillator, and within this environment, there is a pre-existing sense detection system that detects intracardiac signals including depolarization events. The depolarization event can be time windowed to separate it from the whole signal. By operating the LWT on the depolarization event, the time duration, and therefore battery drain, is further minimized. An introduction to the LWT will be provided through explanation, derivation, and demonstration.

The Line Basis Function

Figure 37:
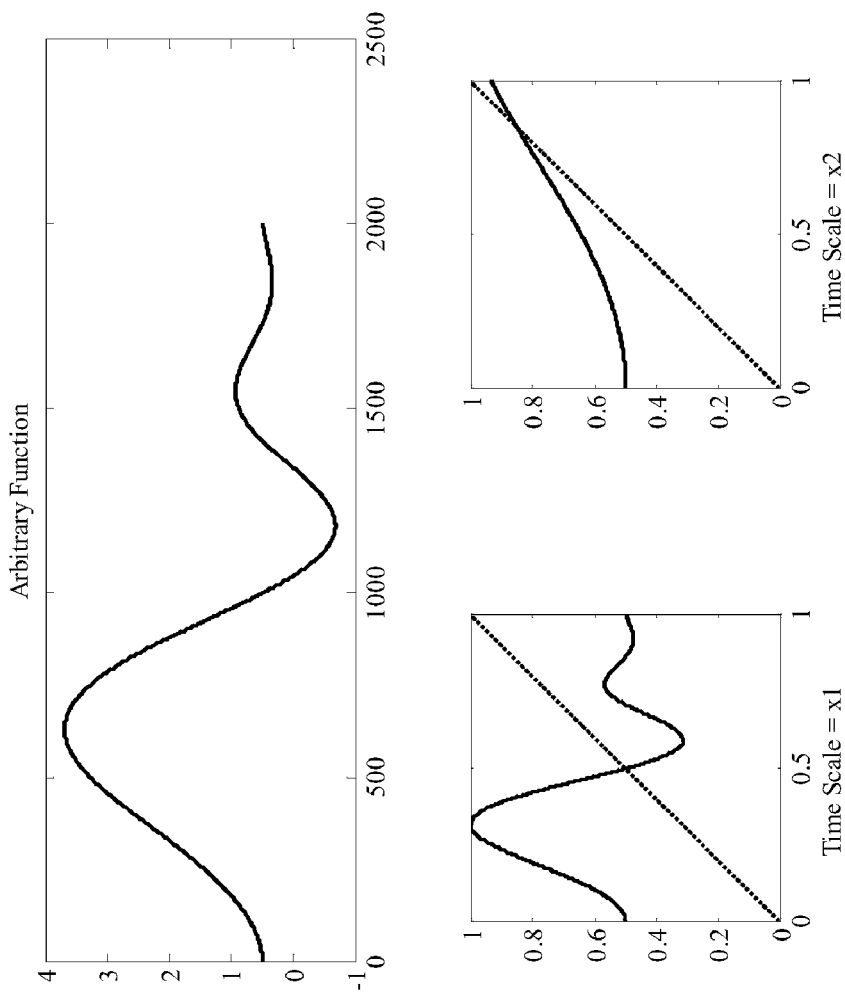

Before the derivation is presented, it is helpful to understand that by translation and scaling any smooth function can be decomposed by a line basis function. It is assumed that when an IEGM is sampled adequately, that its points approximate a smooth function $f$. Allow this function to be scaled for mapping to the unit straight line along y=x, that is, the segment from the point (0, 0) to the point (1,1). FIG. 37 shows three progressively magnified views (top to bottom, right to left) of some arbitrary function. The purpose of the figure is to show that by increasing resolution; eventually a unit diagonal line segment can be scaled and shifted to approximate any finite differentiable function. That is, as $f$ is expanded, the unit line segment is able to approximate smaller segments.

The unit line can be composed of arbitrarily smaller sized sub-intervals (limited by the resolution and sampling rate of the ADC), then there will be a sub-interval of y=x that brackets (from above and below along the diagonal) the fixed point on $f$ that intersects y=x (Casti, 1996, pp. 73-74). Still further, by scaling and sliding, it is possible to arrange this for all the resolvable points of $f$. At small scales, the geometry of $f$ will be locally consistent (Casti, 1996, p. 93), therefore, two cases will occur in the analysis process of the wavelet transform. First, when a line is a good approximation for the three adjacent points (the two bracketing and the fixed point of $f$, the local information content of the signal will be subsumed in the basis function (a line). Second, for a discontinuity, the information content yields a non-zero residual (detail coefficient) from the linear prediction. Subsequently, for the next pass at the next larger scale, only the resulting smooth linear values are operated on in the next stage of the wavelet transform so that the function appears piece-wise linear punctuated by discontinuities. Residuals to the line fit are increasingly winnowed at each step of the transform.

The method for approximating with line segments and removing residuals with the LWT is described in the following sections. Though the discontinuities that persist to the later passes of the transform give the overall shape of the event, the earlier calculated small-scale details may yet be significant in terms of a dichotomizing classifier.

Transfer Function of the Line Wavelet

Figure 38:
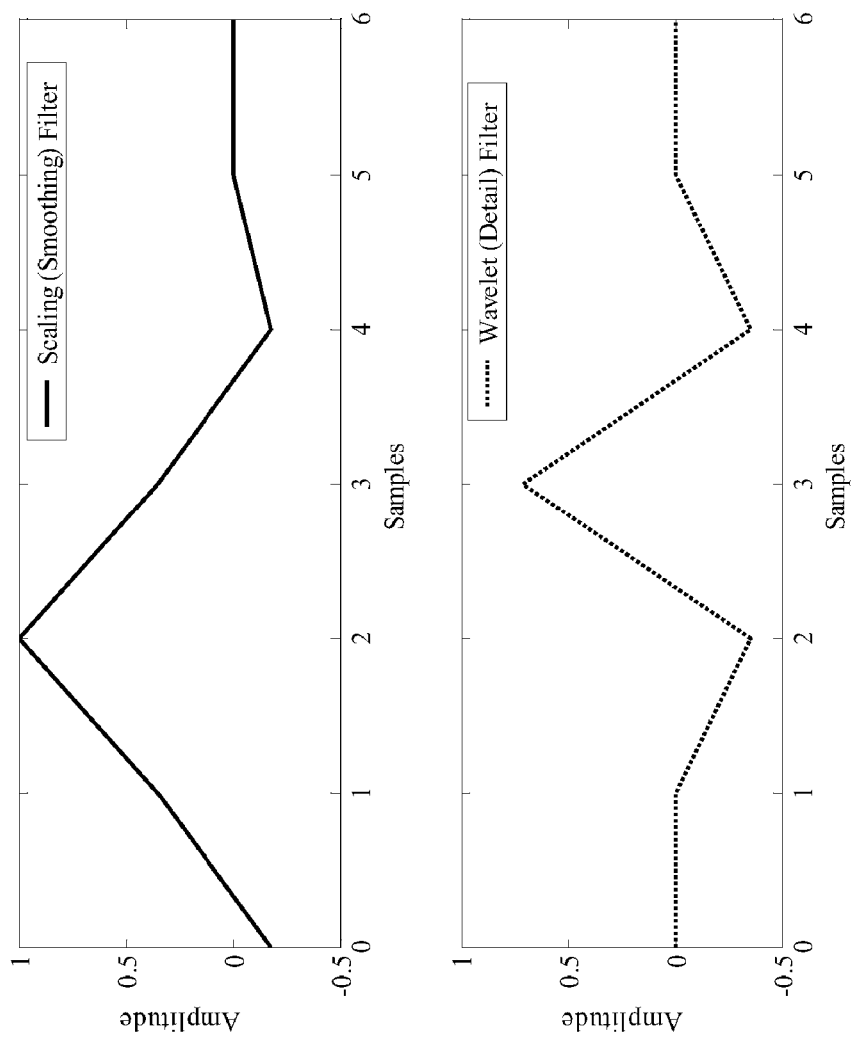
FIG. 38 shows the impulse response of discrete time lifting line wavelet transform filters.

The Line Wavelet decomposition of a signal is accomplished through two filters (Cohen, Daubechies, & Feauveau, 1992, p. 542). The lifting line wavelet transform is not causal (Table 3), therefore, there is a delay of samples. The impulse response of the filter is shown in FIG. 38.

Figure 39:
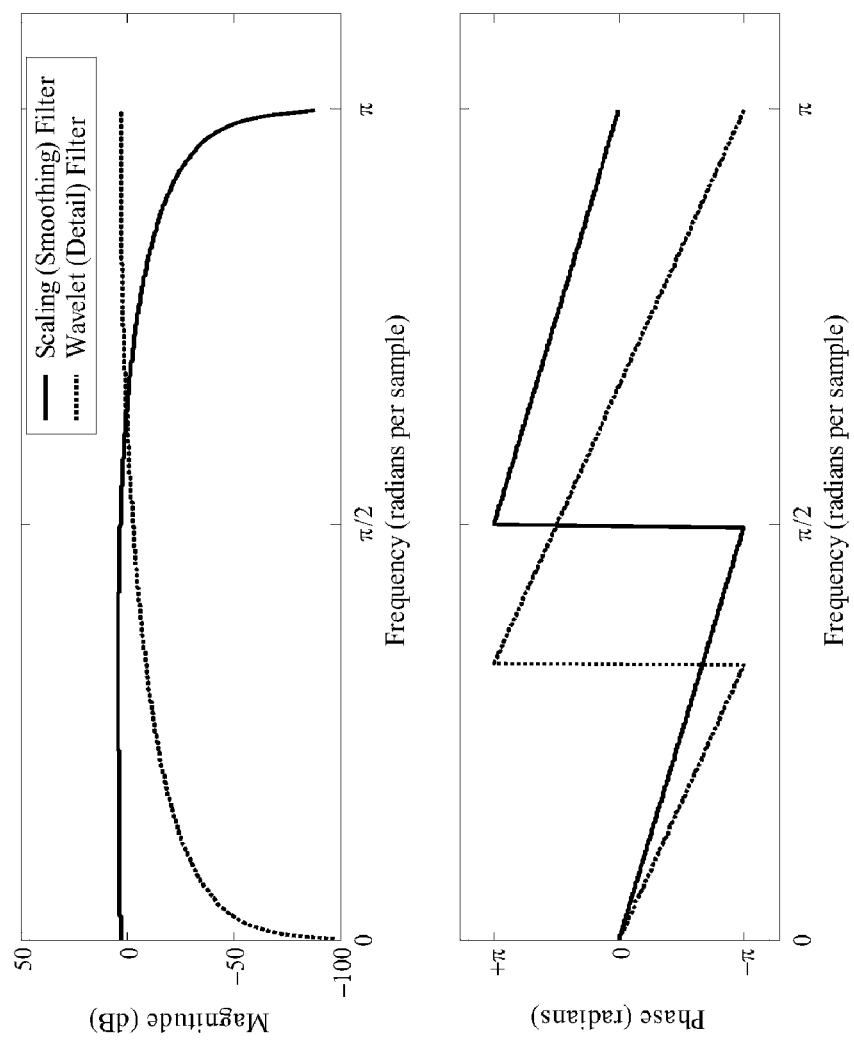
FIG. 39 shows the magnitude and phase response of low and high pass WT blocks.

The magnitude and phase of the transfer functions of these two blocks are shown in FIG. 39.

By splitting the output recursively using these two building blocks, and applying subsequent decomposition to the resulting low pass output stream only, multiresolution analysis can be performed O(n) with the applicable delays or storage to synchronize the outputs of the analysis levels.

Figure 40:
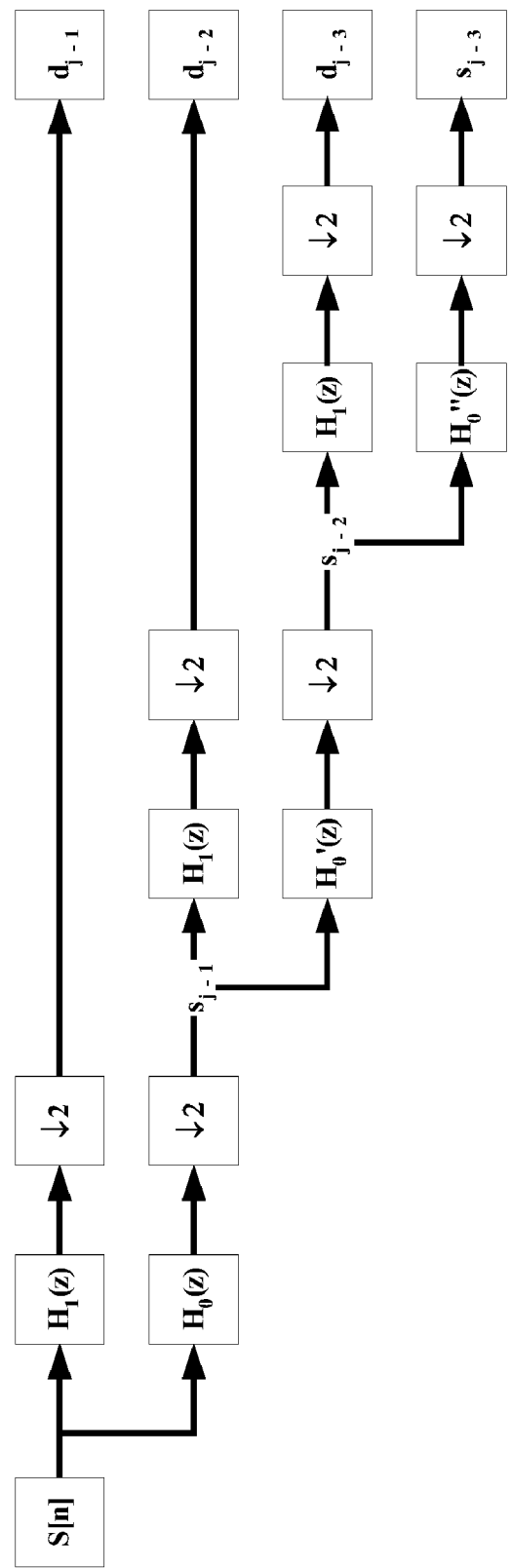
FIG. 40 shows a dataflow diagram of analysis levels.

In FIG. 40, the left most block is the discrete signal. Once a sample passes through the wavelet function $H_1(z)$ it becomes a detail $d_{j\text{-}level}$ and is not processed further. The samples passing through the scaling function $H_0(z)$ become smoothed values $(s_{j\text{-}level})$ which are treated like the original signal. Note that each filter step is a different band pass with its own cutoff frequency. Therefore, each filter is followed by a downsampling by 2 to undo the duplication of samples that results from the same sample passing through both the high and low pass data paths (Daubechies, 1996, p. 512). Additionally, with each level, the filter must be expanded to span double the time scale of the previous level by being applied only to the output of the downsampler, hence, the time scaled versions $H'_0(z)$ and $H''_0(z)$.

The method described so far is of complexity $O(n^2)$. Fortunately, all finite impulse response wavelet transforms, (for example, §Transfer Function of the Line Wavelet) have a Lifting equivalent method, which is presented next.

The Indexing Method Controlling Scaling

Figure 41:
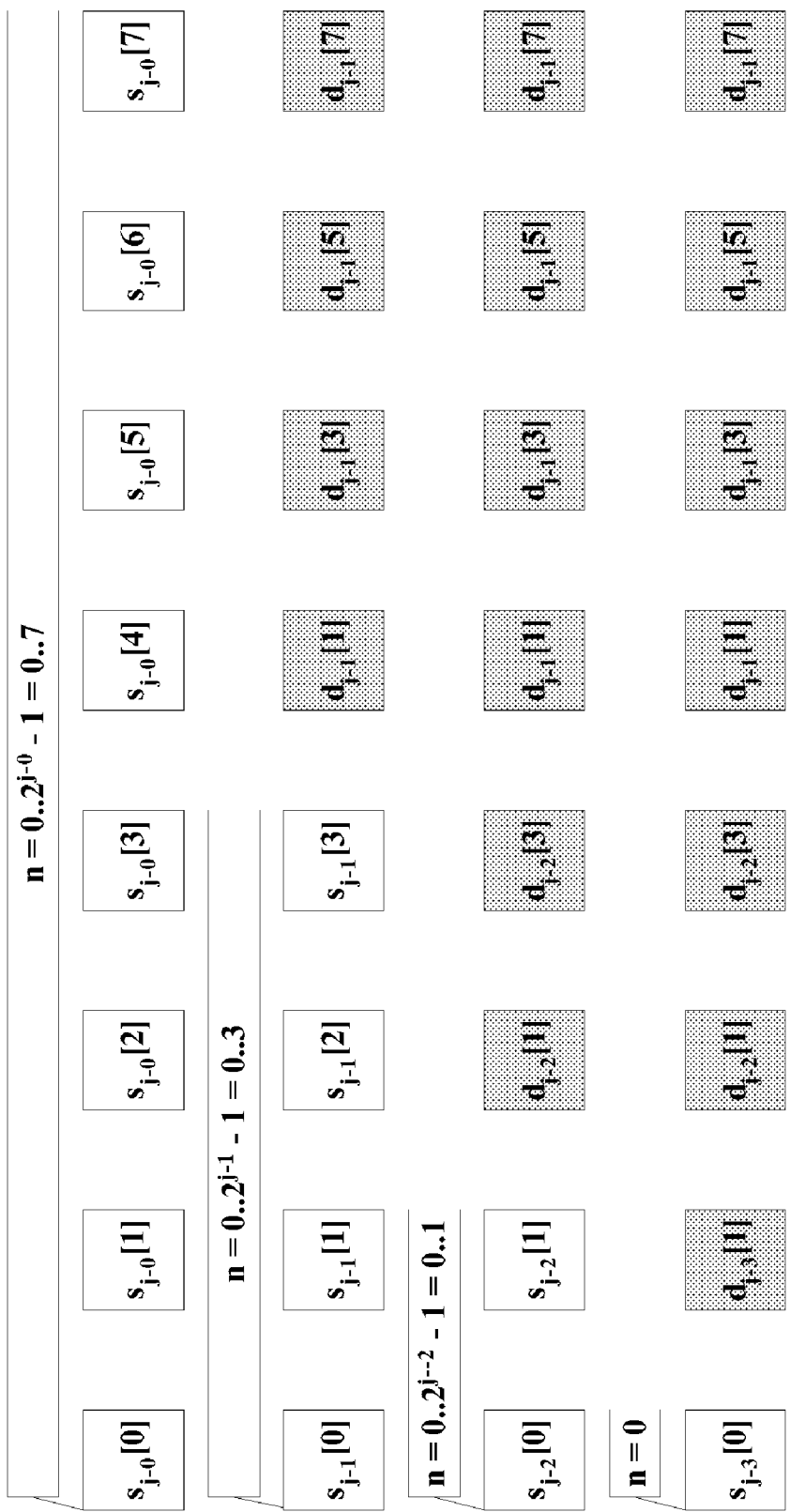
FIG. 41 shows how the scaling spans the signal values.

As described in §Time Scale Correlation of the Wavelet Transform, the line basis function is re-scaled recursively to cover the large and small features of the time domain data. The small example in FIG. 41 demonstrates this relationship. The scaling of the Line Wavelet Transform (LWT) is defined as follows: The discrete time IEGM signal is windowed so that it is a limited sequence of length N equal to an integer power of two. Let $j=\log_2 N$ where j is the number of sub-bands resulting from the transform ranging from $\log_2(N)$ to zero in steps of −1.

When j=0, the last detail value (d) and most smoothed value (s) is calculated, all other values have been reduced to detail coefficients, and the transform has ended. The range of the index (n) indicates the scope of the values on which to perform the transform and is controlled by $n=0 \ldots 2^j-1$ for each sub-band. As the range of values shrinks by half, the scale of the wavelet function is expanding by two. The transform starts (top row of FIG. 41) with N=8 arbitrary signal values, clear boxes, (no WTC, gray boxes, have been calculated yet and j−0=3). Iteration of the transform proceeds from the top row of the figure to the bottom. The number of sub-bands or transform levels to complete is $j=\log_2(N)=3$. For the first pass of the transform, the scope of values is all eight values indexed $n=0 \ldots 7$. Note that as the scope of n appears to be shrinking on values, the representation of the wavelet basis is expanding by two with each pass until it spans the entire length of the original signal (Refer again to FIG. 25). This converse effect of expanding the scope of the representation as the number of values is shrinking occurs because the present smoothed values, labeled by n, are combined to generate half as many smoothed samples for the next pass. In other words, the piece-wise linear representation of the signal is reconstructed for the next step with half the pieces from the previous step. Therefore, the remaining smooth values now represent longer time spans within each band. When only one smooth value is left, it represents the mean of the entire time span of the original data.

Linear Prediction

Now the constraint has been implied that the transform preserves the mean in the smoothed values. This would be necessary since the only way to convey that mean to the final single smooth value is through the smoothed values of the predecessor steps. For a sequence of length $2^j$, the mean of the sequence (s) is:

$$\bar{S} = 2^{-j} \cdot \sum_{n=0}^{2^j-1} s_j[n]$$

(This is the familiar arithmetic mean). Let the predictor of any particular value in the sequence be a line segment between the two adjacent even indexed samples on either side of it, that is, $$s_{j-1}[n] = \frac{1}{2}(s_j[2 \cdot n] + s_j[2 \cdot n + 2]),$$

where $s_{j-1}[n]$ is an estimator $\hat{s}_j[2 \cdot n + 1]$.

Note the subscripts j show that the right hand side values generate the left hand side j−1, that is, the resulting smooth value for the next pass of the transform. In addition, using this notation, the predecessor odd entries are indexed as: $s_j[2 \cdot n+1]$.

The Detail Value

Figure 42:
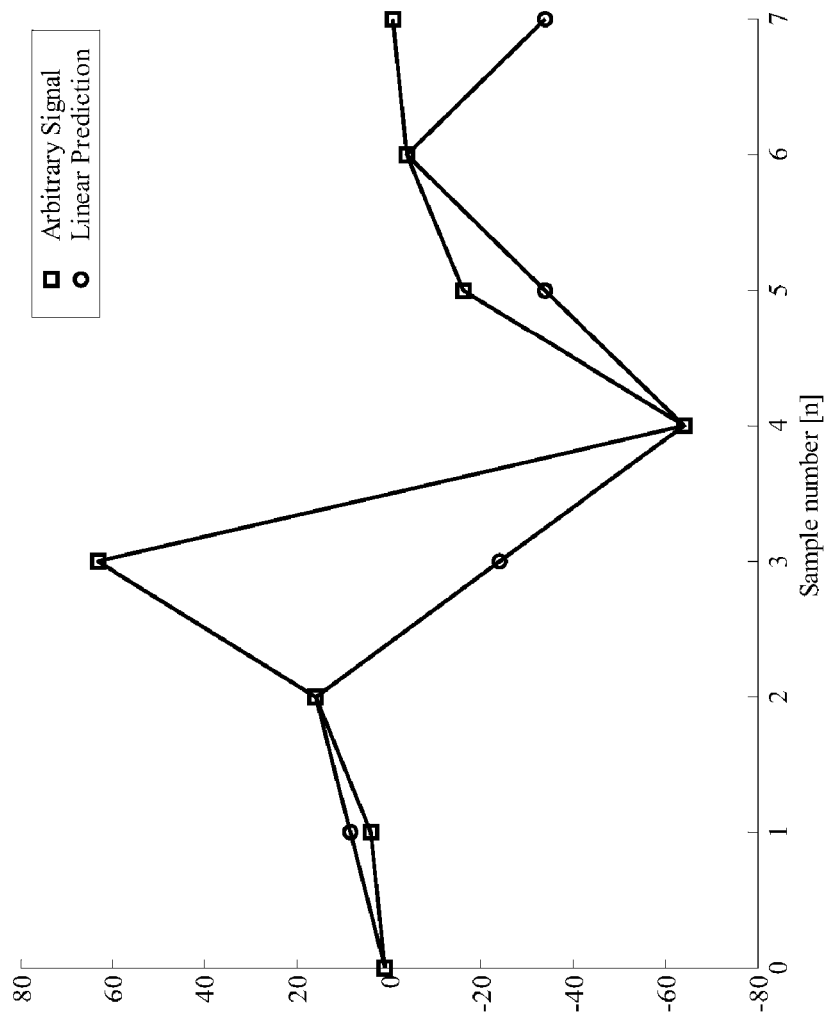
FIG. 42 shows how even samples predicting odd samples.

FIG. 42 illustrates this. The line showing the arbitrary signal is marked by the □ symbol. For every odd sample (squares at 1, 3, 5 . . . ), the line showing the linear prediction of the arbitrary function (○ symbol) is synthesized from the two adjacent even samples ((0, 2), (2, 4), (4, 6) . . . ). It is the difference between this predicted value and the actual signal value that is stored as a detail or wavelet coefficient. This difference is:

$$d_{j-1}[n] = s_j[2 \cdot n + 1] - \frac{1}{2}(s_j[2 \cdot n] + s_j[2 \cdot n + 2]).$$

The right hand side reads: the odd sample minus the arithmetic mean of the two adjacent even samples. Note that for sample number 7 in the next figure, it has no even value that comes after it (the sample window is finite and support is compact).

The boundary handling method shown in FIG. 42 is the nominal linear interpolation method using the mean of the two prior even samples to predict the last odd sample. In the figure, the boundary value (□ at x=7) is predicted by linear interpolation of the prior two even values (□ at x=4 and x=6) resulting in the prediction value (○ at x=7). In the following §The Predict Function, several alternative boundary handling methods, including the method proposed by this work, will be presented.

The Smoothed Value

It is required that the mean be preserved over the smoothed values between bands, that is, $$\sum_{n=0}^{2^{j-1}-1} s_{j-1}[n] = \frac{1}{2} \cdot \sum_{k=0}^{2^j-1} s_j[k]$$

(Jensen & la Cour-Harbo, 2001). The right hand side (predecessor band) has twice as many smoothed samples as the left hand side (successor band). As the detail $d_{j-1}[n]$ was generated by the odd sample and the two adjacent even samples, the smoothed value for the next sub-band $s_{j-1}[n]$ is updated by the even sample and the two new detail values on either side of it. The relationship for this is expressed by:

$$s_{j-1}[n] = s_j[2 \cdot n] + A \cdot (d_{j-1}[n-1] + d_{j-1}[n]).$$

This reads: the smoothed value for the next sub-band is generated by the even value on the predecessor level plus a scaled sum of the detail coefficients. The scale factor A is derived as follows:

Distributing A:

$$s_{j-1}[n] = s_j[2 \cdot n] + A \cdot (d_{j-1}[n-1]) + A \cdot (d_{j-1}[n])$$

Recall that the detail just generated is:

$$d_{j-1}[n] = s_j[2 \cdot n + 1] - \frac{1}{2}(s_j[2 \cdot n] + s_j[2 \cdot n + 2])$$

If n=1, for instance, then 2·n=2 and the two samples being predicted are 1 and 3, therefore, the earlier detail generated from sample 1 is:

$$d_{j-1}[n-1] = s_j[2 \cdot n - 1] - \frac{1}{2}(s_j[2 \cdot n - 2] + s_j[2 \cdot n])$$

Replacing the detail terms with their even value equivalents:

$$s_{j-1}[n] = s_j[2 \cdot n] + A \cdot \left(s_j[2 \cdot n - 1] - \frac{1}{2}(s_j[2 \cdot n - 2] + s_j[2 \cdot n])\right) + A \cdot \left(s_j[2 \cdot n + 1] - \frac{1}{2}(s_j[2 \cdot n] + s_j[2 \cdot n + 2])\right)$$

Distributing:

$$s_{j-1}[n] = s_j[2 \cdot n] + A \cdot s_j[2 \cdot n - 1] - \frac{A}{2} \cdot s_j[2 \cdot n - 2] - \frac{A}{2} \cdot s_j[2 \cdot n] + A \cdot s_j[2 \cdot n + 1] - \frac{A}{2} \cdot s_j[2 \cdot n] - \frac{A}{2} \cdot s_j[2 \cdot n + 2]$$

The constraint to be satisfied can be expanded into even and odd terms:

$$\sum_n s_{j-1}[n] = \frac{1}{2} \cdot \sum_n s_j[n] = \frac{1}{2} \cdot \sum_n s_j[2 \cdot n] + \frac{1}{2} \cdot \sum_n s_j[2 \cdot n + 1]$$

Gathering the even and odd terms:

$$\sum_n s_{j-1}[n] = \left(1 - \frac{A}{2} - \frac{A}{2} - \frac{A}{2} - \frac{A}{2}\right) \cdot \sum_n s_j[2 \cdot n] + (A + A) \cdot \sum_n s_j[2 \cdot n + 1]$$

This gives simultaneous equations for A and the solution:

$$1 - 2 \cdot A = \frac{1}{2}$$

$$2 \cdot A = \frac{1}{2}$$

$$A = \frac{1}{4}$$

The generation of the smoothed successor value is:

$$s_{j-1}[n] = s_j[2 \cdot n] + \frac{1}{4} \cdot (d_{j-1}[n-1] + d_{j-1}[n]).$$

The Splitting Function

Figure 43:
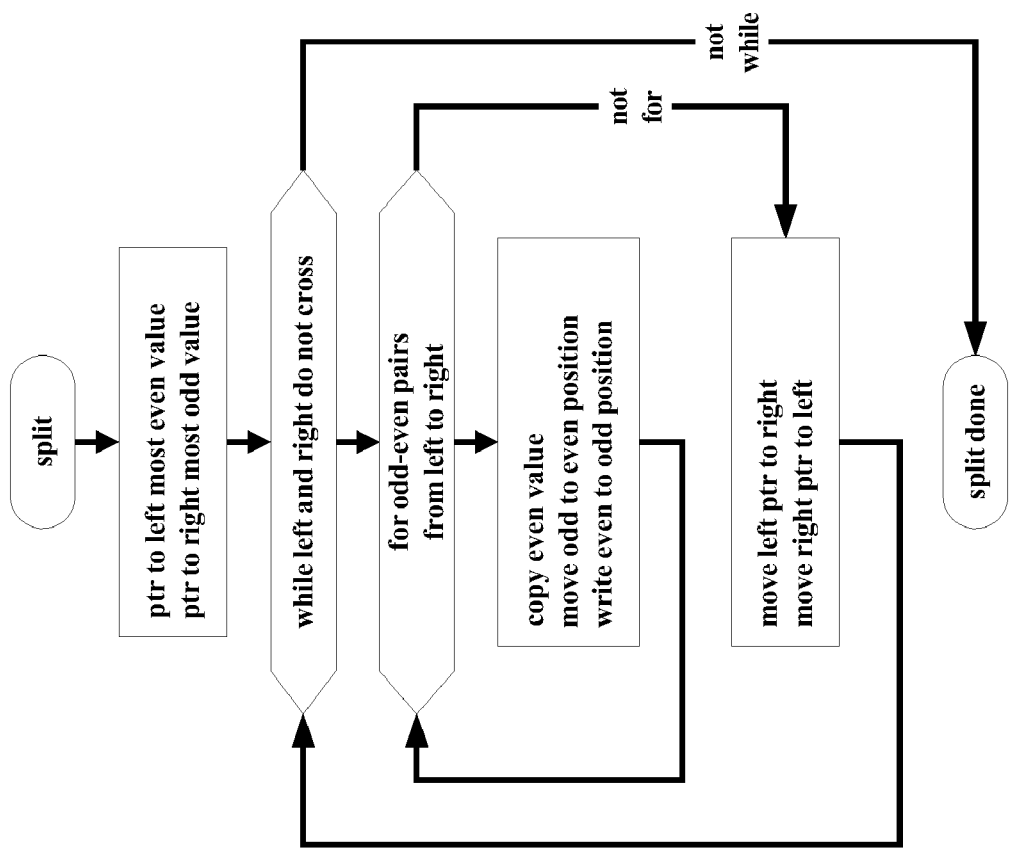
FIG. 43 shows a flow diagram of the splitting function.

In the Lifting wavelet transform, downsampling by two is accomplished by separating even and odd samples before filtering. FIG. 43 is the flow diagram. Note that, although the pseudocode diagram involves a 'copy', the in-place transform can be accomplished entirely with pointers without moving any values.

An example on a small sample of arbitrary integer values should demonstrate how the splitting function works. The values are chosen purposely as a numerical sequence to show that they have been redistributed into even values in the first half and odd values in the last half.

Figure 44:
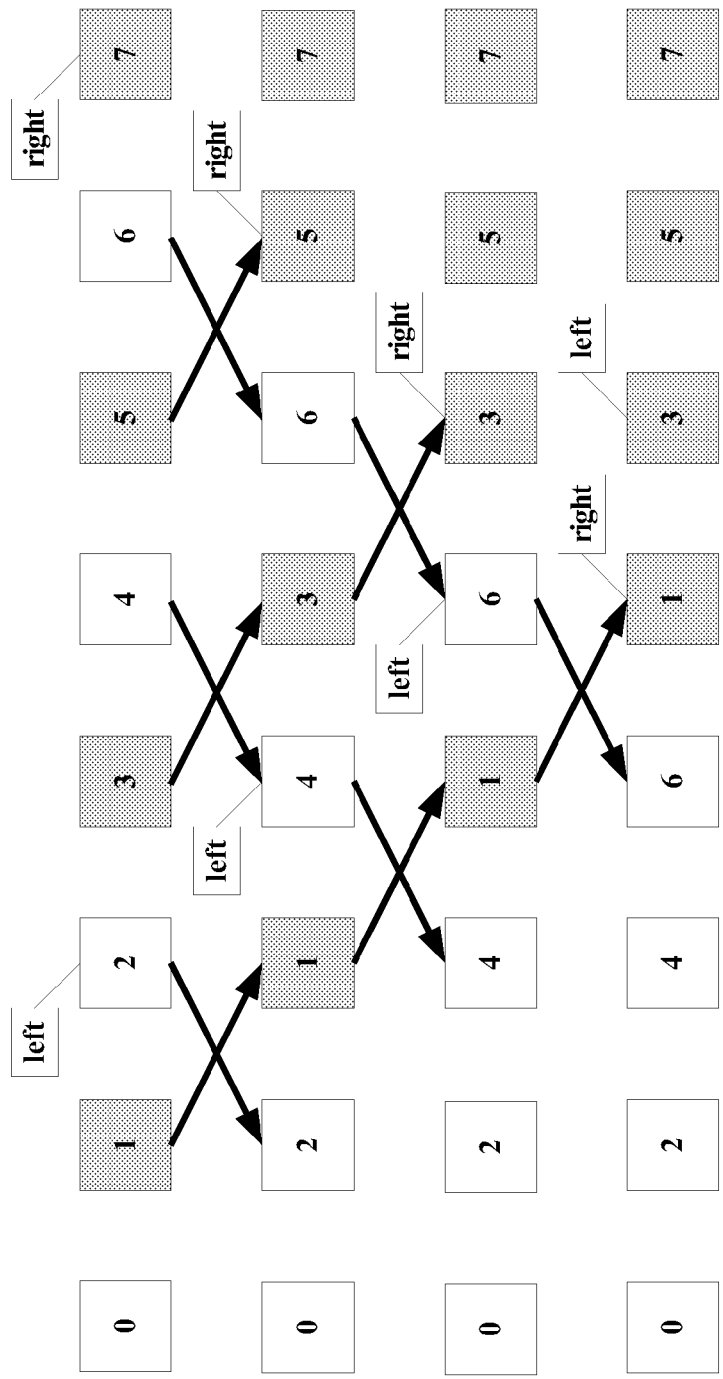
FIG. 44 shows how splitting redistributes even and odd values, for operations on 'smooth' (clear box) and 'detail' (gray box) values, respectively.

'Left' and 'Right' from FIG. 43 are pointed to the first 'even' and last 'odd' values to process in FIG. 44. Note that in the final pass of Split, right and left have crossed causing the function to exit. Not seen elsewhere in the literature, it can be seen that element '0' and element '7' are already in the correct position for 'even' and 'odd,' respectively. Therefore, by judicious initial placement of the pointers 'Left' and 'Right' at the start of each sub-band calculation, a small but cumulative reduction in processing is achieved. Iteration of the transform proceeds from the top row of the figure to the bottom.

Signal elements are redistributed, evens (clear boxes) to first half, odds (gray boxes) to the second half of the N element region. Note that first even element index 0 and last odd element N−1 are already in the correct position, and so never move. Since evens and odds have lost their original parity, they are now the new 'smooth' and 'detail' values, respectively. With each pass of the transform, even and odd values are split producing the new smooth and detail values for the next application of the predict and update iterations of the transform. Note that, only the new smooth values are operated on by each successive pass of the transform. The result is an integer power of two scaling of the original wavelet basis function (the line). The result scaling is that the ratio of the scaled filter bandwidth to the center frequency is constant through the sub-bands and the Q of these filters is constant (Theodoridis and Koutroumbas, 2003, p. 247).

The Predict Function

Figure 45:
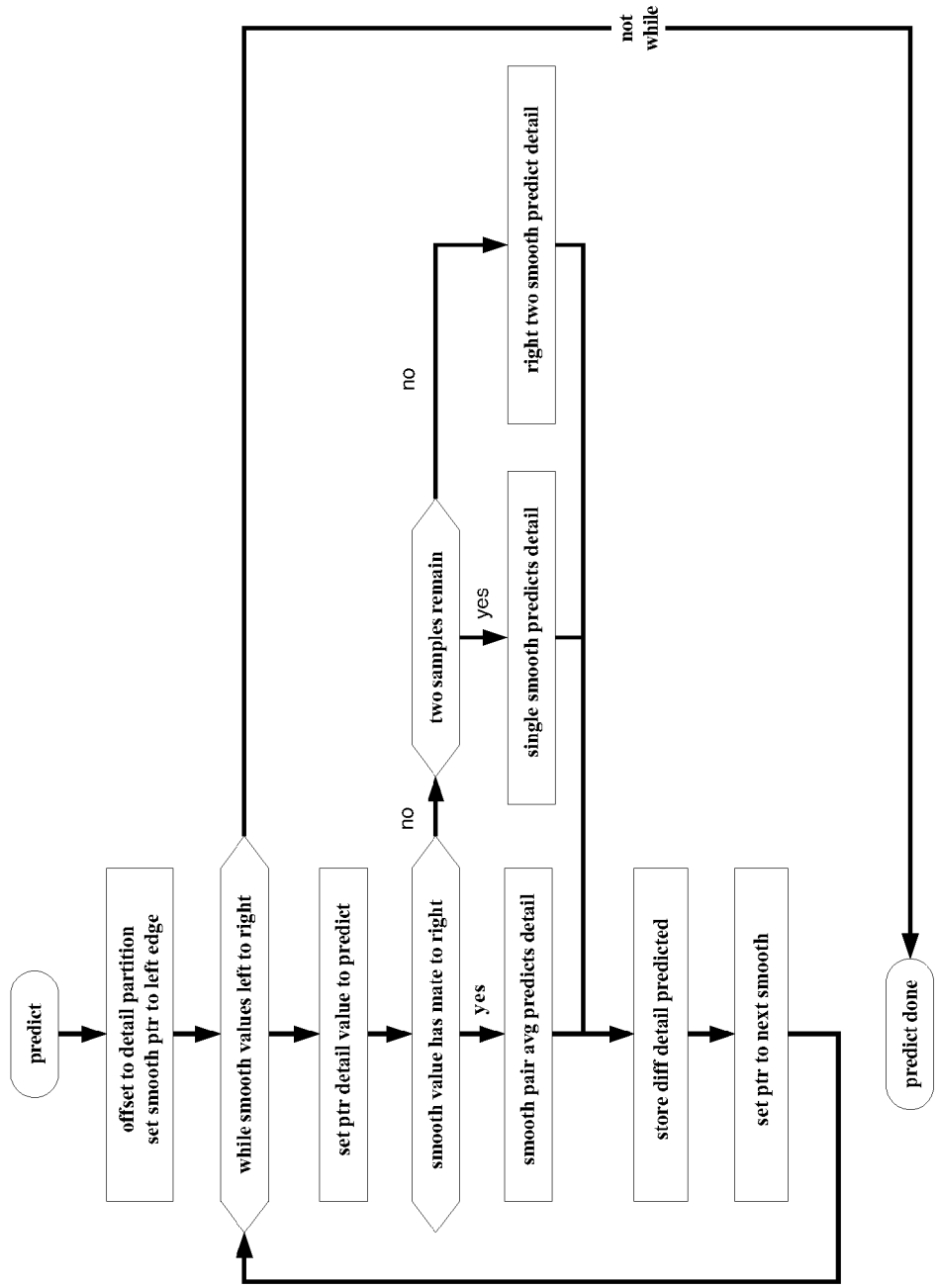
FIG. 45 shows the predict function.

The flow chart in FIG. 45 delineates the flow of the operation that follows splitting of the signal data in the forward wavelet transform, that is, the predict function.

The purpose of Predict is to generate the new detail value, which is the residual from the prediction. Predict proceeds from left to right taking pairs of new smooth values (generated the split operation) and computing arithmetic mean as a prediction. The predicted value is subtracted from target detail value leaving a signed difference. This remainder stored in place of the old detail value.

Figure 46:
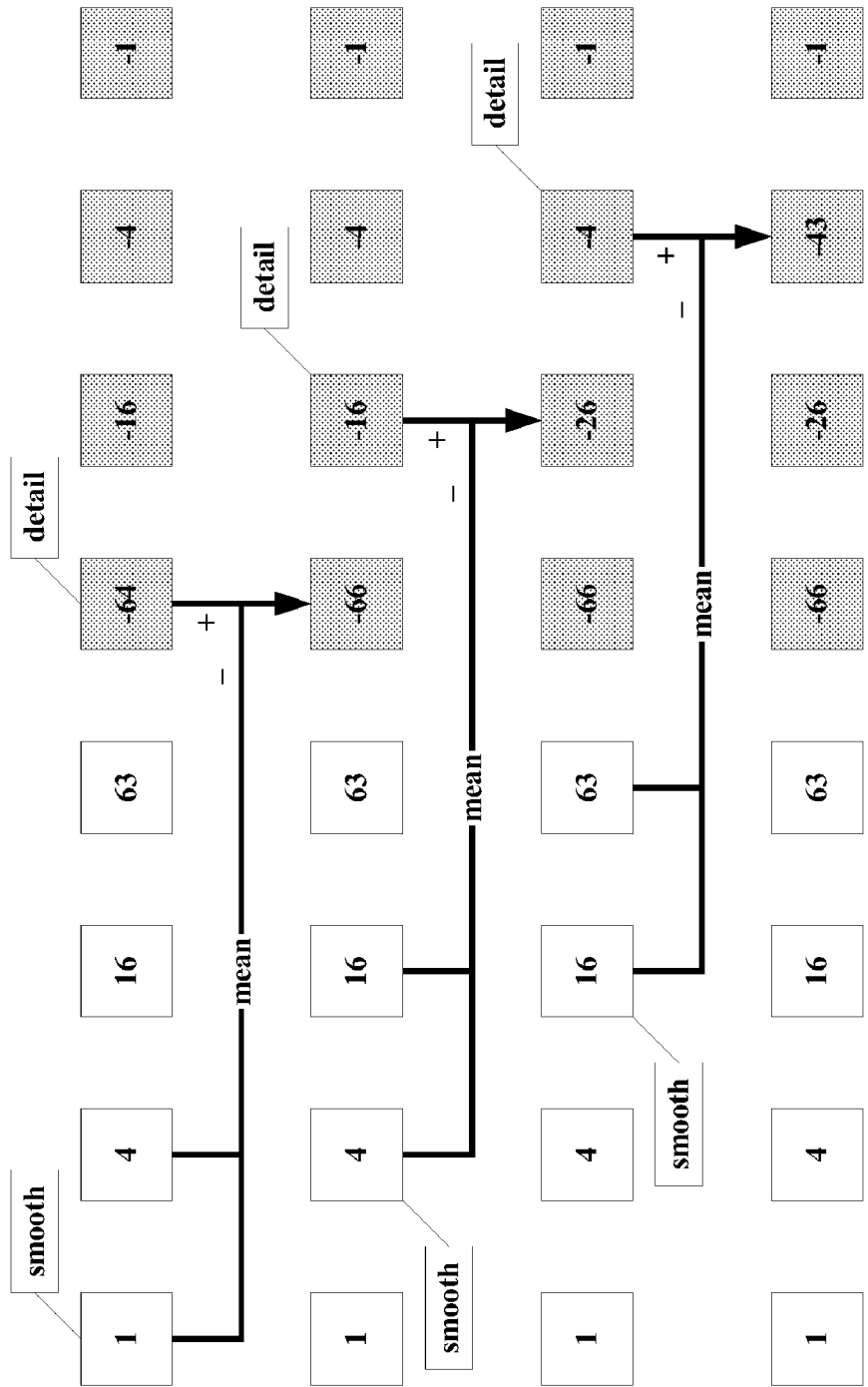
FIG. 46 shows that predict leaves the residual in place of the detail.

The following example in FIG. 46 demonstrates the flow diagram for predict function. Iteration of the transform proceeds from the top row of the figure to the bottom. In the example, integer values are used and rounding is by truncation.

For non-boundary values, the Line wavelet predict function linearly interpolates the expected value of the detail element $d_j[n]$ formerly between two adjacent smooth elements $s_j[2 \cdot n]$ and $s_j[2 \cdot n+2]$ giving the detail value estimator:

$$\hat{s}_j[2 \cdot n + 1] = \frac{s_j[2 \cdot n] + s_j[2 \cdot n + 2]}{2}.$$

This is the point slope formula for a line and simplifies because $s_j[2 \cdot n]$ is translated back to the origin and the sampling interval is fixed so $\Delta x$ can be normalized to one. Division by two can be accomplished by right shifting (truncation), and the prediction value $\hat{s}_j[2 \cdot n+1]$ is subsequently subtracted from the detail value. The difference is the wavelet coefficient (WTC) and can be thought of as a residual or prediction error. The new detail value is stored in the location of the old one.

Exception cases exist for the time sample and iteration limits of the transform. The first exception case occurs when the right edge detail value is predicted; the right most two smooth values are used. For the detail value at the right hand edge of the data, there is no corresponding value $s_j[2 \cdot n+2]$. There are two common alternatives to the nominal right edge boundary handling method (§The Detail Value and FIG. 46) and a third new method proposed by this work. The first and most simple method is called the 'Haar approximation', which assumes that values past the window boundary become zero:

$$\hat{s}_j[2 \cdot n + 1] = \frac{s_j[2 \cdot n] + 0}{2} = \frac{s_j[2 \cdot n]}{2}.$$

Another method uses the point slope formula for a line but double weights the right most of the two even values:

$$\hat{s}_j[2 \cdot n + 3] = \frac{2 \cdot s_j[2 \cdot n + 2] - s_j[2 \cdot n]}{2}$$ (Kaplan, 2003).

The two previous methods are linear interpolation and generate edge effects. The edge effects can be minimized by using the problem domain knowledge that the tail end of the depolarization waveform is often a decaying ramp. Barring the processing cost of the exponential function, a line approximates such a ramp at minimal cost. Again, the point slope formula for a line simplifies because $s_j[2 \cdot n]$ is translated back to the origin and the sampling interval is fixed so $\Delta x$ can be normalized to one. Therefore, this work proposes the linear extrapolation:

$$\hat{s}_j[2 \cdot n + 3] = \frac{3 \cdot s_j[2 \cdot n + 2] - s_j[2 \cdot n]}{2}.$$

The second exception case occurs when the recursion of the transform leaves two values (a single smooth and a single detail). In this second case, the single smooth value is the predictor. This single smooth value has accumulated the average of all other smooth values through the transform levels. The prediction value in this case is $\hat{s}_j[2 \cdot n+1]=s_j[2 \cdot n]$.

The Update Function

Figure 47:
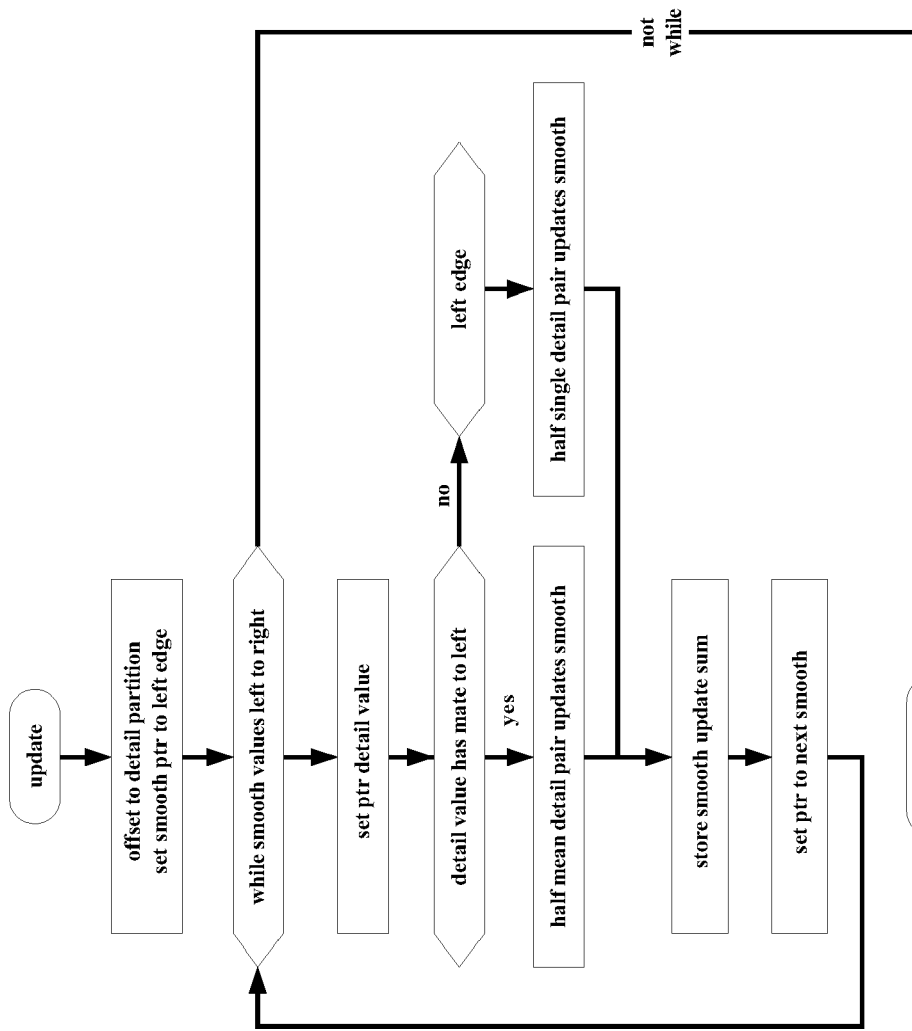
FIG. 47 shows the update function.

The purpose of the Update function shown in FIG. 47 is to generate a new smoothed value that preserves some moment of the original data through the sub-bands. A requirement on the update function (§The Smoothed Value) for the LWT is to preserve the mean. This mean is accumulated through the scales. The detail information is incorporated into the smoothed value in the update operation. The flow chart (FIG. 47) shows the operations performed.

Figure 48:
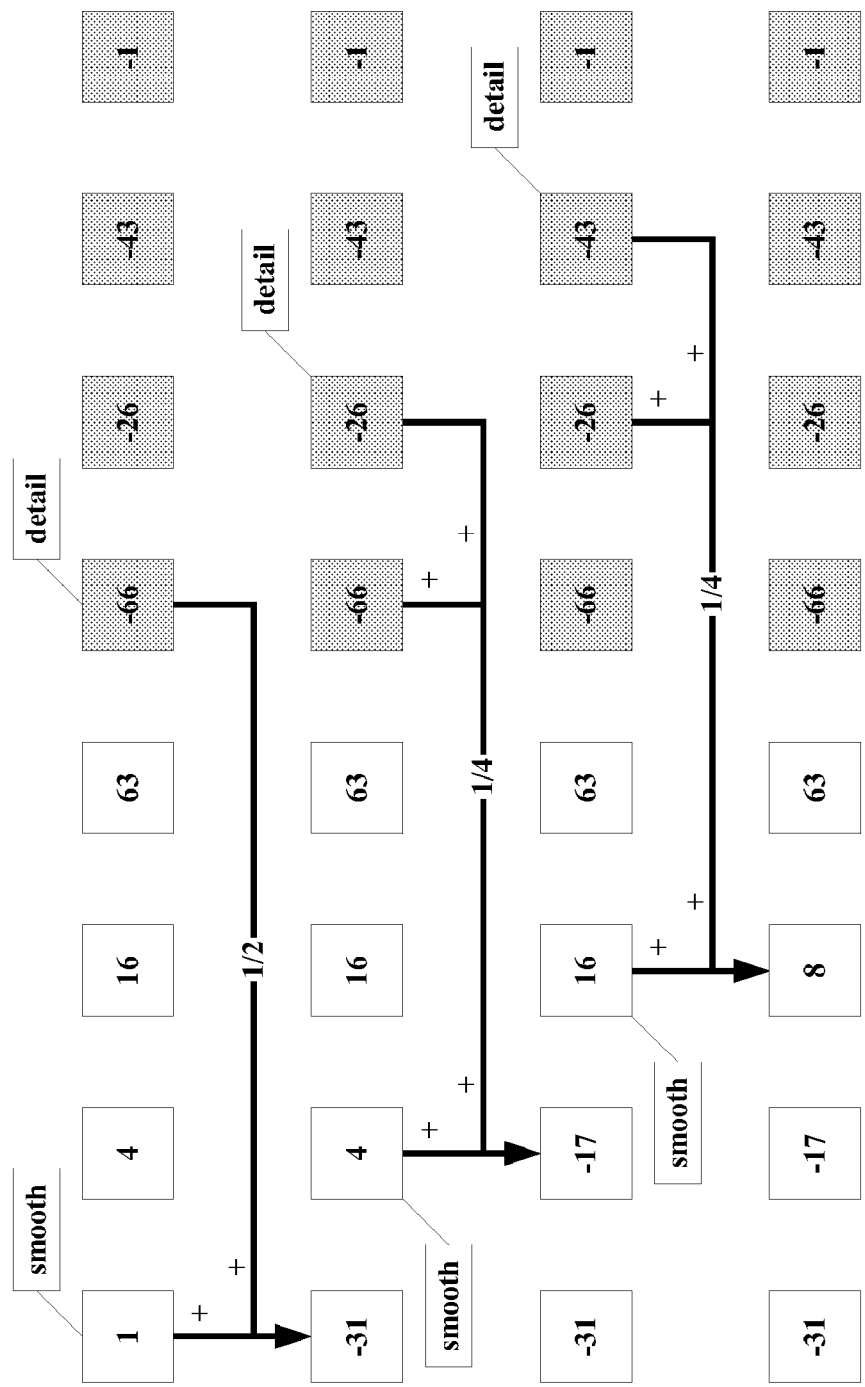
FIG. 48 shows that update preserves the mean by adjusting smooth values.

The worked example in FIG. 48 shows the left edge handling for the case of a single detail value to update a smoothed value. Iteration of the transform proceeds from the top row of the figure to the bottom. The next two steps show the nominal case of the two corresponding detail values updating the smooth value. Only a few steps are shown for brevity.

The Forward Line Wavelet Transform

The LWT produces WTC by recursively scaling the span of operations Split, Predict, and Update data values until a single smooth value remains. FIG. 49 shows the flow diagram of the forward transform. Here 'forward' mean analysis or decomposition as opposed to synthesis or reconstruction. The recursive signal separation of the LWT then orthogonalizes not only the information content of the signal but also noise components (§Dimension Reduction Property). An integer only version of the LWT is preferred for several reasons. First, floating-point values are not uniformly spaced in a finite resolution system and can create a false distribution outline for the feature. Second, although the implant can use fixed-point it is much more complex to implement than integer representation. Third, integer valued wavelet coefficients are lossless and retain full reconstructability of the original signal (even truncation effects are reversible by the synthesis version of the transform if system requirements in §Present Pacemaker Input Stage Architecture are met). Note that, the above described transform is the 'in-place' version. Therefore, the original sample values are, by stages, completely replaced with coefficients. The classifier overwrites the values of the original waveform, and only requires the most meaningful of these. The transform is, however, completely reversible, in the case that a user wants to retrieve the original waveform, such as, for HMS.

Chapter 8

CONCLUSION

In Chapter 2, the IEGM was introduced as a signal source for generating features to classify cardiac events. In Chapter 3, the principles of acquiring that signal and the benefit of applying the wavelet transform, such as time/scale localization, to that signal was discussed. In Chapter 4, the aspects of a working system for wavelet transform for feature generation were introduced. In Chapter 5, the accuracy results of using wavelet transform coefficients as features in the separation of IEGM event classes was reported and analyzed.

Discussion

The objective of the work presented in this disclosure was to show the feasibility of categorizing IEGM events using wavelet-generated features. Using human IEGM, windowed and aligned time domain data was decomposed by an integer-only adaptation of the lifting line wavelet transform. These adaptations specifically address issues of limited computation within an implant, sampling rate, ADC resolution, and properties of the transform itself that affected feature generation. Further, a systematic method was developed to extract a subset of all features to reduce processing load while maintaining discrimination of event types.

Summary of Contributions
1. Feasibility was demonstrated in a computer simulation prototype of discriminator that has both high sensitivity and specificity for morphological information in the bipolar IEGM sampled at 512 Hz and 10 bits of amplitude resolution. The method was not blind to, but rather correctly discriminated normal from abnormal (retrograde), and pseudo-events (T-waves and far-field). This demonstrates the possibility of highly accurate online event classification, and therefore classification of the important rhythms (Table 1), in an implanted device. This was accomplished without a redesign of existing technology, such as, the requirement of a new sensor (§Use of the Intra-Cardiac Electrogram).
2. The method in this work used temporally independent datasets to choose features in the definition phases (reference and confirmation) to discriminate events in the evaluation phase with $\geq 95\%$ accuracy over 78 recordings with repeatability error of 5%, greatly exceeding the sensitivity and specificity of present devices (§Justification of Work, §Benefits of an Implantable Wavelet-based Classifier, §Statistical Evaluation of the Discriminator).
   a. A method was proposed and applied to assure the adequate size of the data splits (§Effective Independence of Data Splits) where the maximum time of possible correlation affected accuracy was 31 s.
   b. There were 78 recordings with a cumulative length of 126, 321 s and 158, 343 events classified.
3. Features used for discrimination were generated by an adaptation of the line wavelet transform developed for this work:
   a. Windowed time samples of IEGM depolarization events were peak aligned by a method developed for this work (Table 2).
   b. Employing numerous problem domain insights, an adapted version of the discrete time lifting line wavelet transform (LWT) was developed for this work, accompanied by an extensive analysis for the choice of this transform over others not found elsewhere (§Time Scale Correlation of the Wavelet Transform, §Selecting the Best Basis, §Errors in Event Detection and Peak Alignment, §Advantages of the Integer-Based Lifting Line Wavelet). Improvements to the nominal LWT included omission of the float-valued-scaling factor, integer operations only, a custom boundary handling method, partial execution of the transform, and processing improvement in the Splitting function. The adaptations did not significantly reduce the accuracy, and improved the service life reduction costs (FIG. 29 and Table 4).
   c. The postulate that detail coefficients are as important as smooth coefficients in correct discrimination is borne out by the results (See FIG. 35) contrary to the compression-oriented literature (§Limitations of Present Day Event Detection Methods, §Coarse Scale Selection of Coefficients).
4. A systematic classifier independent method of feature ranking and reduction was applied; that is, an application of the receiver operating characteristic curve area to rank wavelet transform coefficients for their IEGM discrimination power (in contrast to the prior literature §The Basis of Morphological Differences). The method reduced the feature count to one while still achieving $\geq 95\%$ accuracy over the 78 IEGM recordings.
   a. The alternate methods AUC or confirmation accuracy methods of choosing a WTC were analyzed for trade-offs of energy savings and evaluation accuracy. Energy savings was 27% and 21%, respectively, for the AUC and confirmation accuracy method, respectively. The $\geq 95\%$ accuracy acceptance criterion was met for 97% and 98% of patient records, for the AUC and confirmation accuracy method, respectively 5. Bootstrap (resampling 1000 times with replacement) was performed to give bias corrected statistics with confidence intervals for all parameters.

Limitations

The constraints on this work specifically required inferring an event category from frames of limited pre-annotated IEGM event observations. After the definition phase, further samples from the IEGM were not allowed to contribute to the reference definition, but were subject to evaluation. Thus, there is a risk of a Type I error because the alternate hypothesis (IEGM events can be discriminated by WTC) is suggested by the data, the non-favorable data having been discarded by ROC analysis. In the case of discriminating between categories, the method is exposed to many samples of normal and fewer examples of abnormal events. This disparity in relative occurrence promotes Type II errors by missing detection of the class 2 event whose a priori probability is small.

Disorganized rhythms require a different method that was not explored here. Atrial fibrillation, for example, produces so many different morphologies for the same class of arrhythmia that the exemplar method is likely untenable.

The IEGM is non-stationary, and cardiac tissue changes will cause a slow evolution of the exemplar to a new form (Swerdlow et al., 2002, p. 438). The trigger for relearning the best feature was not examined here, but it is considered that too many events falling into a rejection region between classes should trigger re-training of the classifier. However, updated reference definitions can also be made available to the algorithm during implantation testing of the device, using rate-based rules, during the clinical follow-up, and within other offline scenarios using stored IEGMs from the patient. Recordings were a maximum of 40 minutes long, and thus do not demonstrate efficacy of the method on circadian or longer-term morphological changes.

TABLE 1

Key rhythms to classify in an implantable pacemaker or defibrillator can be characterized by rate, but are more accurately discriminated by shape.

| Rhythm Class | Rhythm Rate Categories | Event Shape Categories |
|---|---|---|
| Normal sinus rhythm | Normal atrial | Normal atrial |
| | Normal ventricular | Normal ventricular |
| Sinus tachycardia | Elevated atrial | Normal atrial |
| | Elevated ventricular | Normal ventricular |
| Supra-ventricular tachycardia | Elevated atrial | Abnormal atrial |
| | Elevated ventricular | Normal ventricular |
| Ventricular tachycardia | Elevated atrial | Abnormal atrial |
| | Elevated ventricular | Abnormal ventricular |

TABLE 2

Terms regarding lead tip polarity in pacing and sensing (Dorland, 2003).

| Function | Tissue Contact | Device Contact | Contact Name |
|---|---|---|---|
| Pacing | Tip | Negative Pace Output | '−' |
| Pacing | Ring (bipolar) Case (unipolar) | Positive Pace Output | '+' |
| Sensing | Tip | Non-inverting input | 'DIFF' |
| Sensing | Ring (bipolar) Case (unipolar) | Inverting input | 'INDIFF' |

(Note: The negative lead of the pulse generator is connected to the tip for tissue stimulus. The non-inverting input of the sense amplifier is connected to the tip.)

TABLE 3

Complexities of the three most basic wavelets make clear the rapidly increasing computational complexity.

| Type | Filter | Operation |
|---|---|---|
| Haar | Detail | $c_n = \frac{1}{\sqrt{2}}[-s_{2n} + s_{2n+1}]$ |
| Haar | Smooth | $a_n = \frac{1}{\sqrt{2}}[s_{2n} + s_{2n+1}]$ |
| Line | Detail | $c_n = \frac{1}{\sqrt{2}}\left[-\frac{s_{2n}}{2} + \frac{s_{2n+1}}{1} - \frac{s_{2n+2}}{2}\right]$ |
| Line | Smooth | $a_n = \frac{1}{\sqrt{2}}\left[-\frac{s_{2n-2}}{4} + \frac{s_{2n-1}}{2} + \frac{3s_{2n}}{2} + \frac{s_{2n+1}}{2} - \frac{s_{2n+2}}{4}\right]$ |
| D4 | Detail | $c_n = \frac{1}{\sqrt{2}}\left[\frac{-[1-\sqrt{3}]s_{2n-2} + [3-\sqrt{3}]s_{2n-1} - [3+\sqrt{3}]s_{2n} + [1+\sqrt{3}]s_{2n+1}}{4}\right]$ |
| D4 | Smooth | $a_n = \frac{1}{\sqrt{2}}\left[\frac{[1+\sqrt{3}]s_{2n} + [3+\sqrt{3}]s_{2n+1} + [3-\sqrt{3}]s_{2n+2} + [1-\sqrt{3}]s_{2n+3}}{4}\right]$ |

TABLE 4

Definition of parameters used in the generation of the ROC curve.

| ROC Term | Synonym | Statistics | Equation |
|---|---|---|---|
| True Positive Rate (sensitivity) | Recall Rate | $H_1 \neq H_0$, or $1-\beta$ | $\dfrac{TP}{TP+FN}$ |
| True Negative Rate (specificity) | Rejection Rate | $H_1 = H_0$, or $1-\alpha$ | $\dfrac{TN}{TN+FP}$ |
| False Positive Rate (1 − specificity) | False Alarm Rate | Type I Error, or Significance ($\alpha$) | $\dfrac{FP}{TN+FP}$ |
| False Negative Rate (1 − sensitivity) | Miss Rate | Type II Error, or Power ($\beta$) | $\dfrac{FN}{TP+FN}$ |

TABLE 5

The peak magnitude is aligned in the buffer.

1. Discrete time IEGM samples continually enter a length N FIFO buffer.
2. If the blanking period is over and an amplitude threshold crossing is detected:
   a. Start a blanking period.
   b. The peak alignment counter is set to N/2 counter.
   c. The absolute value of the present sample is stored as maxValue.
3. While 0 < N/2 for each new sample:
   a. If the absolute value of any subsequent sample exceeds maxValue,
     i. The absolute value of the present sample is stored as maxValue.
     ii. The N/2 counter is reset (slip).
   b. Else, decrement the N/2 counter.
     i. maxValued sample moves toward the center of the buffer.
4. If the N/2 counter reaches 0:
   a. Store the present length N FIFO buffer into a memory location.
   b. Event will be aligned on electrical field maximum.

TABLE 6

LWT Processing cost is estimated on a microprocessor and a DSP.

| Platform | Code Cost | Current Cost | Reduction Factor | Service Life Reduction |
|---|---|---|---|---|
| Microprocessor (custom) | 2222 instructions 4 cycles/opcode 475 kHz μP clock | 18.7 ms/LWT 1.87% duty 100% duty = 1s | $1.67 \dfrac{\text{months}}{\%\ \text{duty}}$ | 3.14 months per channel |
| DSP (custom) | 741 lines LWT 1 cycle/line 475 kHz DSP clock | 39.9 μA/s 1.56 ms/LWT 62.2 nA/LWT | $3.8 \dfrac{\text{months}}{\mu A}$ | 0.24 months per channel |

TABLE 7

Patient data summary by event discrimination task.

| Discrimination Task | Recording time and count | Number of Events | Maximum Autocovariance |
|---|---|---|---|
| Atrial | | | |
| Normal versus far-field | 31875 s 24 records | 28753 normal 17908 far-field | 11 s |
| Spontaneous versus pace | 40782 s 19 records | 16784 spontaneous 6231 paced | 31 s |
| Normal versus abnormal | 6350 s 2 records | 531 normal 936 abnormal | 4 s |
| Ventricular | | | |
| Normal versus far-field | 8825 s 4 records | 5019 normal 1494 far-field | 1 s |
| Normal versus T-wave | 15607 s 18 records | 33661 normal 26734 T-wave | 3 s |
| Spontaneous versus pace | 18203 s 9 records | 11055 spontaneous 2664 paced | 11 s |
| Normal versus abnormal | 4679 s 2 records | 3264 normal 3309 abnormal | 2 s |
| Totals | | | |
| Record Length 126321 s | Record Count 78 | Event Count 158343 | Autcovariance Max 31 s |

TABLE 8

The assessment methodology.

1. Band pass filter IEGM 2 Hz to 189 Hz.
2. Quantize amplitude data to 1 Obits.
3. Calculate time to autocovariance diminished to noise level.
4. Identify event time stamps.
5. Identify event peak time stamps.
6. LWT 32 samples centered on peak time stamps.
7. Calculate reference ROC AUC and thresholds for 32 WTC on first ⅓ IEGM data.
   a. Bootstrap resample 1000 times each parameter mean and 95% lower confidence level.
8. Calculate confirmation Accuracies for 32 WTC on second ⅓ IEGM data.
   a. Bootstrap resample 1000 times each parameter mean and 95% lower confidence level.
9. Select the highest numbered WTC equal to max(confirmation accuracy).
10. Calculate evaluation accuracies for best single WTC on last ⅓ IEGM data.
   a. Bootstrap resample 1000 times each parameter mean and 95% lower confidence level.
11. Analyze energy savings from resulting sub-band distribution of evaluation accuracies.

TABLE 9

Mean evaluation accuracies for the event categories by WTC sub-bands.

| Discrimination Task | Selection Method | Mean Evaluation Accuracy of the Selected WTC by Sub-band | | | | |
|---|---|---|---|---|---|---|
| | | 17...32 | 9...16 | 5...8 | 3...4 | 1...2 |
| Atrial | | | | | | |
| Atrial normal versus far-field | AUC | 0.98 | Unselected | 0.96 | Unselected | Unselected |
| | Accuracy | 0.99 | 0.98 | Unselected | 1.00 | 1.00 |
| Atrial normal versus pace | AUC | 0.98 | 1.00 | Unselected | 1.00 | Unselected |
| | Accuracy | 1.00 | 1.00 | 1.00 | 1.00 | Unselected |
| Atrial normal versus abnormal | AUC | 0.96 | Unselected | Unselected | Unselected | Unselected |
| | Accuracy | 0.96 | Unselected | 1.00 | Unselected | Unselected |
| Ventricular | | | | | | |
| Ventricular normal versus far-field | AUC | 0.99 | Unselected | Unselected | Unselected | Unselected |
| | Accuracy | 0.99 | 0.96 | Unselected | Unselected | 0.99 |
| Ventricular normal versus T-wave | AUC | 0.97 | Unselected | 0.99 | Unselected | 0.98 |
| | Accuracy | 0.98 | Unselected | 1.00 | Unselected | 0.98 |
| Ventricular normal versus pace | AUC | 0.93 | 0.97 | Unselected | Unselected | 0.99 |
| | Accuracy | 0.97 | 0.98 | Unselected | 0.99 | 0.99 |
| Ventricular normal versus abnormal | AUC | Unselected | 0.96 | Unselected | 0.89 | Unselected |
| | Accuracy | Unselected | 0.91 | 0.97 | Unselected | Unselected |

TABLE 10

FIR filter equivalent of the HWT and LWT wavelet smoothing functions.

| Wavelet | Operation | Filter Equivalent |
|---|---|---|
| Haar | Smoothing | $a_n = [s_{2n} + s_{2n+1}] \cdot \frac{1}{2}$ |
| Line | Smoothing | $a_n = \left[ -\frac{s_{2n-2}}{4} + \frac{s_{2n-1}}{2} + \frac{3s_{2n}}{2} + \frac{s_{2n+1}}{2} - \frac{s_{2n+2}}{4} \right]$ |

Closing

A modified wavelet based feature extraction and new application of dimension reduction for the classification of human cardiac electrogram depolarization waveforms has been demonstrated by this work. The algorithm discriminates cardiac event types accurately within a model of a processing limited device, such as, an implantable pacemaker or cardiodefibrillator. Thus, this disclosure shows methods of implementing this feature for cardiac rhythm therapy devices.

Although an exemplary embodiment of the present invention has been shown and described, it should be apparent to those of ordinary skill that a number of changes and modifications to the invention may be made without departing from the spirit and scope of the invention. This invention can readily be adapted to a number of different kinds of physiologic monitoring devices and heart therapy devices by following the present teachings. All such changes, modifications and alterations should therefore be recognized as falling within the scope of the present invention.

What is claimed is

1. A monitoring device for monitoring and evaluation of a physiological signal including a cardiac electrogram to detect physiological events and/or categorize physiological events and discriminate them from each other by way of comparison to prototype events comprising:
    a monitoring device comprising a signal preprocessing stage having an input for a digitized physiological signal being a digital representation of a time course of a physiological signal;
    said signal preprocessing stage comprising an event-detector that is adapted to determine a fiducial point for at least one segment of said physiological signal by detecting reoccurring characteristic features within said physiological signal including R-waves or p-waves;
    said monitoring device further comprising a wavelet coefficient generation stage that is adapted to perform a modified lifting line wavelet transformation on a segment of said physiological signal relative a selected fiducial point in a signal segment to thus generate wavelet transformation coefficients as features of said digitized physiological signal;
    a feature evaluation stage that is adapted to perform a reduction of features of said digitized physiological signal by selecting those wavelet transformation coefficients that have been determined to be most characteristic of prototype events from each other by means of a receiver operation characteristics curve analysis;
    a feature threshold memory comprising a threshold value for each selected feature of a prototype event, said threshold value being determined by said receiver operation characteristics curve analysis; and,
    a comparator stage connected to said feature threshold memory and being adapted to compare said selected features of an actual digitized physiological signal to corresponding threshold values for a prototype event and to assign said actual digitized physiological signal to a prototype event category if each or a majority of said selected features of said actual digitized physiological signal is within a threshold defined by a corresponding one of said threshold values.

2. The monitoring device according to claim 1, wherein said wavelet coefficient generation stage is adapted to perform said modified lifting line wavelet transformation based on a high pass detail filter and a corresponding low path smoothing filter to thus obtain wavelet detail and scale coefficients, respectively.

3. The monitoring device according to claim 2, wherein said wavelet coefficient generation stage is adapted to perform said modified lifting line wavelet transformation recursively thus obtain further wavelet detail coefficients for a next scale based on smoothed values determined while determining detail coefficients for a previous scale.

4. The monitoring device according to claim 1, wherein said signal preprocessing stage has at least one further input for additional input signals, such as an accelerometer value or cardiac impedance values.

5. The monitoring device according to claim 1, wherein said signal preprocessing stage is adapted to generate a feature vector from the wavelet coefficients produced by said wavelet coefficient generation stage and said further input values for further processing by said feature evaluation stage.

6. The monitoring device according to claim 1, wherein said feature evaluation stage is adapted to perform feature evaluation in relation to wavelet coefficients produced from a signal segment centered on a fiducial point of each signal segment to be evaluated.

7. The monitoring device according to claim 1, wherein said monitoring device comprises a threshold determination stage comprising a receiver operation characteristics analyzer that is adapted to process features including wavelet coefficients of a regular event and another specific prototype event that are time aligned with each other based on said fiducial point to thus determine the most characteristic features and to further determine and store a threshold value for each of said most characteristic features in said threshold memory.

8. The monitoring device according to claim 1, wherein said threshold memory comprises more than one set of threshold values wherein each of said threshold values corresponds to a particular prototype event and wherein the comparator stage is adapted to compare said selected features of an actual digitized physiological signal to corresponding threshold values for each prototype event separately.

9. The monitoring device according to claim 1, wherein said comparator stage comprises a kernel discriminant analyzer adapted to perform a kernel discriminant analysis on said selected features of an actual digitized physiological signal to assign said selected features of an actual digitized physiological signal to one of a plurality of prototype events used to determine a kernel discriminant for discrimination between the prototype events.

10. A heart therapy system comprising an implantable heart stimulator and an external device comprising:
    an implantable heart stimulator comprising a signal sensing stage;
    a signal preprocessing stage having an input for a digitized physiological signal being a digital representation of a time course of a physiological signal, said input being connected to said signal sensing stage;
    said signal preprocessing stage comprising an event-detector that is adapted to determine a fiducial point for at least one segment of said physiological signal by detecting reoccurring characteristic features within said physiological signal such as R-waves or p-waves;
    an external device comprising
        a wavelet coefficient generation stage that is adapted to perform a modified lifting line wavelet transformation to thus generate wavelet transformation coefficients as features of said digitized physiological signal;
        a feature evaluation stage that is adapted to perform a reduction of features of said digitized physiological signal by selecting those wavelet transformation coefficients that have been determined to be most characteristic for discriminating a prototype event from a regular event by means of a receiver operation characteristics curve analysis;
        a feature threshold memory comprising a threshold value for each selected feature of a proto-type event, said threshold value being determined by means of said receiver operation characteristics curve analysis; and,
        a comparator stage connected to said threshold memory and being adapted to compare said selected features of an actual digitized physiological signal to corresponding threshold values for a prototype event and to assign said actual digitized physiological signal to the prototype event if each or a majority of said selected features of said actual digitized physiological signal is within the threshold defined by a corresponding one of said stored threshold values.

11. The heart therapy system according to claim 10 wherein said sensing stage comprises a band path filter having a pass band between 5 Hz and 100 Hz.

12. The heart therapy system according to claim 10 wherein said sensing stage is adapted to be connected or is connected to a bipolar electrode lead.

13. A heart therapy system comprising an implantable heart stimulator and an external device comprising:

an implantable heart stimulator comprises a signal sensing stage;

a signal preprocessing stage having an input for a digitized physiological signal being a digital representation of a time course of a physiological signal, said input being connected to said sensing stage;

said signal preprocessing stage comprising an event-detector that is adapted to determine a fiducial point for at least one segment of said physiological signal by detecting reoccurring characteristic features within said physiological signal such as R-waves or p-waves;

an event detecting stage comprising a wavelet coefficient generation stage that is adapted to perform a modified lifting line wavelet transformation to thus generate wavelet transformation coefficients as features of said digitized physiological signal;

a feature evaluation stage that is adapted to perform a reduction of features of said digitized physiological signal by selecting those wavelet transformation coefficients that have been determined to be most characteristic ones for discriminating a prototype event from a regular event by means of a receiver operation characteristics curve analysis;

a feature threshold memory comprising a threshold value for each selected feature of a prototype event, said threshold value being determined by means of said receiver operation characteristics curve analysis;

a comparator stage connected to said threshold memory and being adapted to compare said selected features of an actual digitized physiological signal to corresponding threshold values for a prototype event and to assign said actual digitized physiological signal to the prototype event if each or a majority of said selected features of said actual digitized physiological signal is within the threshold defined by a corresponding one of said stored threshold values;

an external device comprising a threshold determination stage comprising a receiver operation characteristics analyzer that is adapted to process features including wavelet coefficients of a regular event and a prototype event that are time aligned with each other based on said fiducial point to thus determine the most characteristic features and to further determine a threshold value for each of said most characteristic features to be in said threshold memory of said implantable heart stimulator.

14. The heart therapy system according to claim 13, wherein said sensing stage comprises a band path filter having a pass band between 5 Hz and 100 Hz.

15. The heart therapy system according to claim 13, wherein said sensing stage is adapted to be connected or is connected to a bipolar electrode lead.

16. A heart stimulator comprising a signal sensing stage and a monitoring device according to claim 1 wherein said input of said preprocessing stage is connected to said sensing stage.

17. The heart stimulator according to claim 16, wherein said sensing stage comprises a band path filter having a pass band between 5 Hz and 100 Hz.

18. The heart stimulator according to claim 16, wherein said sensing stage is adapted to be connected or is connected to a bipolar electrode lead.

19. The heart stimulator according to claim 16, wherein said heart stimulator is an implantable pacemaker and/or an implantable cardioverter/defibrillator.

20. A method for monitoring and evaluation of a periodic or quasi-periodic signal such as a cardiac electrogram to detect physiological events and/or discriminate physiological events from each other by way of comparison to prototype events comprising:

signal preprocessing to determine a fiducial point for at least one segment of said physiological signal by detecting reoccurring characteristic features within said physiological signal such as R-waves or p-waves;

wavelet coefficient generating via a modified lifting line wavelet transformation to thus generate wavelet transformation coefficients;

feature evaluating including reduction of features of said digitized physiological signal based on said wavelet transformation coefficients by means of receiver operation characteristics curve analysis to determine a reduced set of most characteristic wavelet coefficients; and, feature comparing to compare said reduced set of wavelet coefficients to one or more stored reduced sets of wavelet coefficients, each stored reduced set of wavelet coefficients corresponds to a prototype event.

* * * * *